United States Patent
Colice et al.

(10) Patent No.: US 12,187,788 B2
(45) Date of Patent: *Jan. 7, 2025

(54) METHODS FOR TREATING ATOPIC DERMATITIS AND RELATED DISORDERS

(71) Applicant: MedImmune Limited, Cambridge (GB)

(72) Inventors: Gene Colice, Gaithersburg, MD (US); Rene van der Merwe, Thriplow (GB); Paul Baverel, Cambridge (GB)

(73) Assignee: MedImmune Limited, Cambridge (GB)

( * ) Notice: Subject to any disclaimer, the term of this patent is extended or adjusted under 35 U.S.C. 154(b) by 758 days.

This patent is subject to a terminal disclaimer.

(21) Appl. No.: 17/084,957

(22) Filed: Oct. 30, 2020

(65) Prior Publication Data

US 2021/0301010 A1  Sep. 30, 2021

Related U.S. Application Data

(60) Provisional application No. 63/068,593, filed on Aug. 21, 2020, provisional application No. 63/061,497, filed on Aug. 5, 2020, provisional application No. 63/037,783, filed on Jun. 11, 2020, provisional application No. 62/993,443, filed on Mar. 23, 2020.

(51) Int. Cl.
| | |
|---|---|
| *C07K 16/24* | (2006.01) |
| *A61K 9/00* | (2006.01) |
| *A61K 39/395* | (2006.01) |
| *A61P 17/04* | (2006.01) |
| *A61K 31/573* | (2006.01) |
| *A61K 45/06* | (2006.01) |
| *A61P 25/20* | (2006.01) |
| *A61P 25/22* | (2006.01) |
| *A61P 25/24* | (2006.01) |
| *A61P 31/04* | (2006.01) |

(52) U.S. Cl.
CPC .......... *C07K 16/244* (2013.01); *A61K 9/0019* (2013.01); *A61K 39/3955* (2013.01); *A61P 17/04* (2018.01); *A61K 31/573* (2013.01); *A61K 45/06* (2013.01); *A61P 25/20* (2018.01); *A61P 25/22* (2018.01); *A61P 25/24* (2018.01); *A61P 31/04* (2018.01); *C07K 2317/51* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/624* (2013.01)

(58) Field of Classification Search
None
See application file for complete search history.

(56) References Cited

U.S. PATENT DOCUMENTS 9,334,331 B2 * 5/2016 Igawa .............. C07K 16/40

FOREIGN PATENT DOCUMENTS

| WO | WO 2005/007699 | | 1/2005 | |
|---|---|---|---|---|
| WO | WO 2007/036745 | | 4/2007 | |
| WO | WO-2017139290 A1 | * | 8/2017 | ............. A61K 39/00 |
| WO | WO/2017186928 | * | 11/2017 | |
| WO | WO-2017186928 A1 | * | 11/2017 | ......... A61K 48/0066 |
| WO | WO 2018/057849 | * | 3/2018 | |
| WO | WO 2018/158332 | | 9/2018 | |

OTHER PUBLICATIONS

Vattekatte, (Peer J, DOI 10.7717/peerj.8408).*
Edwards et al. (2003, JMB 334:103-118).*
Lloyd et al. (2009, Protein Engineering, Eng. Design & Selection 22(3): 159-168).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
Rabia, et al. (2018, Biochemical Engineering Journal 137:365-374).*
Simpson et al, The Journal of the American Academy of Dermatology, May 2018; vol. 78, No. 5, pp. 863-871.*
ClinicalTrials.gov Identifier: NCT03160885, Jan. 16, 2020).*
ClinicalTrials.gov Identifier: NCT03363854, (Jan. 23, 2020).*
Investigator Global Assessment Scale by the International Eczema Council, downloaded from https://www.eczemacouncil.org/investigator-global-assessment-scale on Oct. 18, 2023 (Year: 2023).*
Study Protocol for NCT03160885 (downloaded from https://clinicaltrials.gov/study/NCT03160885#study-plan under "Drug and device information, study documents, and helpful links"; published Aug. 14, 2018) (Year: 2018).*
"International Nonproprietary Names for Pharmaceutical Substances (INN)" Proposed INN list 102 (WHO Drug Information (2009) 23(4): pp. 348.
Blauvelt et al., "Long-term management of moderate-to-severe atopic dermatitis with dupilumab and concomitant topical corticosteroids (Liberty Ad Chronos): a 1-year, randomised, double-blinded, placebo-controlled, phase 3 trial." Lancet 2017; 389: 2287-2303.
Charman et al. "The patient-oriented eczema measure: development and initial validation of a new tool for measuring atopic eczema severity from the patients' perspective." Arch Dermatol. Dec. 2004;140(12):1513-9.
ClinicalTrials.gov Identifier: NCT00638989, A Study to Assess Bioavailability and Pharmacokinetics of CAT-354, Mar. 19, 2008.
ClinicalTrials.gov Identifier: NCT00640016, A Study to Assess the Efficacy, Safety, and Tolerability of CAT-354 in Subjects With Asthma, Mar. 20, 2008.

(Continued)

*Primary Examiner* — Brian Gangle
*Assistant Examiner* — Andrea K McCollum
(74) *Attorney, Agent, or Firm* — Lisa Mueller; Casimir Jones SC

(57) ABSTRACT

The present invention relates to methods for treating atopic dermatitis and related disorders in a subject using an interleukin-13 (IL-13) binding protein, such as an anti-IL-13 antibody or an IL-13-binding fragment thereof.

37 Claims, 16 Drawing Sheets

Specification includes a Sequence Listing.

(56) References Cited

OTHER PUBLICATIONS

ClinicalTrials.gov Identifier: NCT00873860, Study to Evaluate the Safety and Efficacy of CAT-354, Apr. 2, 2009.
ClinicalTrials.gov Identifier: NCT00974675, A Study to Assess Pharmacokinetics, Safety and Tolerability of Multiple Doses of CAT-354 in Subjects With Moderate Asthma, Sep. 10, 2009.
ClinicalTrials.gov Identifier: NCT01402986, "A Safety and Efficacy Study of Tralokinumab in Adults With Asthma", Jul. 27, 2011.
ClinicalTrials.gov Identifier: NCT01482884, "Evaluation of Efficacy and Safety of Tralokinumab in Patients With Active, Moderate-to-severe Ulcerative Colitis" Dec. 1, 2011.
ClinicalTrials.gov Identifier: NCT01592396, "A Phase 1, Open-label Study to Investigate the Pharmacokinetics of Tralokinumab (CAT-354) in Adolescents With Asthma" May 7, 2012.
ClinicalTrials.gov Identifier: NCT01629667, A Phase 2, Randomized Dose-ranging Study to Evaluate the Efficacy of Tralokinumab in Adults With Idiopathic Pulmonary Fibrosis, Jun. 27, 2012.
ClinicalTrials.gov Identifier: NCT02036580, D2212C00002 J-Phase II Study, Jan. 15, 2014.
ClinicalTrials.gov Identifier: NCT02085473, A Study of Tralokinumab When Delivered Subcutaneously at Different Flow Rates to Healthy Volunteers, Mar. 12, 2014.
ClinicalTrials.gov Identifier: NCT02161757, A Phase 3 Study to Evaluate the Efficacy and Safety of Tralokinumab in Adults and Adolescents With Uncontrolled Asthma (STRATOS1), Jun. 12, 2014.
ClinicalTrials.gov Identifier: NCT02194699, A Phase 3 Study to Evaluate the Efficacy and Safety of Tralokinumab in Adults and Adolescents With Uncontrolled Asthma (STRATOS2), Jul. 18, 2014.
ClinicalTrials.gov Identifier: NCT02281357, Phase 3 Study to Evaluate the Efficacy & Safety of Tralokinumab in Adults & Adolescents With OCS Dependent Asthma (TROPOS), Nov. 2, 2014.
ClinicalTrials.gov Identifier: NCT02347176, Phase 2 Study to Evaluate the Efficacy and Safety of Tralokinumab in Adults With Atopic Dermatitis (D2213C00001), Jan. 27, 2015.
ClinicalTrials.gov Identifier: NCT02449473, Study to Evaluate Efficacy & Safety of Tralokinumab in Subjects With Asthma Inadequately Controlled on Corticosteroids May 2015 (MESOS), ClinicalTrials.gov Identifier: NCT02449473.
ClinicalTrials.gov Identifier: NCT02684097, A Pilot Study of Tralokinumab in Subjects With Moderate to Severe Alopecia Areata, Feb. 17, 2016.
ClinicalTrials.gov Identifier: NCT02902809, A Study to Evaluate the Safety of Tralokinumab in Adults and Adolescents With Uncontrolled Asthma, Sep. 16, 2016.
ClinicalTrials.gov Identifier: NCT03131648, Tralokinumab Monotherapy for Moderate to Severe Atopic Dermatitis—ECZTRA 1 (ECZema TRAlokinumab Trial No. 1) (ECZTRA 1), First Posted Apr. 27, 2017.
ClinicalTrials.gov Identifier: NCT03160885, Tralokinumab Monotherapy for Moderate to Severe Atopic Dermatitis—ECZTRA 2 (ECZema TRAlokinumab Trial No. 2) (ECZTRA 2), First Posted May 19, 2017.
ClinicalTrials.gov Identifier: NCT03363854, Tralokinumab in Combination With Topical Corticosteroids for Moderate to Severe Atopic Dermatitis—ECZTRA 3, First Posted Dec. 6, 2017.
ClinicalTrials.gov Identifier: NCT03526861, Tralokinumab Monotherapy for Adolescent Subjects With Moderate to Severe Atopic Dermatitis—ECZTRA 6 (ECZema TRAlokinumab Trial No. 6)., May 16, 2018.
ClinicalTrials.gov Identifier: NCT03556592, Drug-drug Interaction Trial With Tralokinumab in Moderate to Severe Atopic Dermatitis—ECZTRA 4, Jun. 14, 2018.
ClinicalTrials.gov Identifier: NCT03562377, Vaccine Responses in Tralokinumab-Treated Atopic Dermatitis—ECZTRA 5 (ECZema TRAlokinumab Trial No. 5) (ECZTRA 5), Jun. 19, 2018.
ClinicalTrials.gov Identifier: NCT03587805, Long-term Extension Trial in Subjects With Atopic Dermatitis Who Participated in Previous Tralokinumab Trials—ECZTEND, Jul. 16, 2018.
ClinicalTrials.gov Identifier: NCT03761537, Tralokinumab in Combination With Topical Corticosteroids in Subjects With Severe Atopic Dermatitis Who Are Not Adequately Controlled With or Have Contraindications to Oral Cyclosporine A (Ecztra 7), Dec. 3, 2018.
ClinicalTrials.gov Identifier: NCT04556461, Effects of Tralokinumab Treatment of Atopic Dermatitis on Skin Barrier Function (TraSki), Sep. 21, 2020.
ClinicalTrials.gov Identifier: NCT04587453, Tralokinumab in Combination With Topical Corticosteroids in Japanese Subjects With Moderate-to-severe Atopic Dermatitis (ECZTRA 8), Oct. 14, 2020.
ClinicalTrials.gov Identifier: NCT04674826, A Trial to Compare the Pharmacokinetics of Tralokinumab in Healthy Subjects, Dec. 19, 2020.
Eichenfield et al. "Guidelines of care for the management of atopic dermatitis: section 1. Diagnosis and assessment of atopic dermatitis." J Am Acad Dermatol. Feb. 2014; 70(2):338-51.
EMA "Reflection paper on the regulatory guidance for the use of health-related quality of life (HRQOL) measures in the evaluation of medicinal products." EMEA/CHMP/EWP/139391/2004. 2005. Retrieved from the internet <http://www.ema.europa.eu/docs/en_GB/document_library/Scientific_guideline/2009/09/WC500003637.pdf.>.
FDA "The Food and Drug Administration. Guidance for Industry. Patient-Reported Outcome Measures: Use in Medical Product Development to Support Labeling Claims. 2009".
Finlay et al. "Dermatology Life Quality Index (DLQI)—a simple practical measure for routine clinical use" Clin Exp Dermatol. (1994) 19(3): 210-216.
Greiner et al. "A single European currency for EQ-5D health states. Results from a six-country study" The European journal of health economics: HEPAC : health economics in prevention and care. Eur J Health Econ. Sep. 2003; 4(3):222-31.
Guttman-Yassky et al., "Tralokinumab phase 2B study: Effects of the anti-interleukin-13 monoclonal antibody on Staph Aureusskin colonization and systemic levels of inflammatory biomarkers in patients with atopic dermatitis." 24th World Congress of Dermatology, Jun. 10-15, 2019, (Abstract book).
Hanifin et al. "The eczema area and severity index (EASI): assessment of reliability in atopic dermatitis. EASI Evaluator Group." Exp Dermatol. Feb. 2001; 10(1):11-8.
Leung et al., "Deciphering the complexities of atopic dermatitis: shifting paradigms in treatment approaches." J Allergy Clin Immunol. Oct. 2014; 134(4):769-79.
May et al. "Preclinical development of CAT-354, an IL-13 neutralizing antibody, for the treatment of severe uncontrolled asthma." Br J Pharmacol. May 2012; 166(1):177-93.
Medicom Conference Highlights, American Academy of Dermatology annual meeting Washington D.C. Mar. 1-5, 2019 [Retrieved Feb. 15, 2021] Retrieved from the internet <https://conferences.m3medical.com/aad-2019/article/tralokinumab-improves-eczema-and-reduces-staphylococcus-aureus-colonisation-in-ad/>.
NIHR—Tralokinumab for atopic dermatitis, Health Technology Briefing 2019, Leo Pharma UK, 13 pages.
Nomura et al., "Cytokine milieu of atopic dermatitis, as compared to psoriasis, skin prevents induction of innate immune response genes." J Immunol. Sep. 15, 2003;171(6):3262-9.
Panettieri et al., "Tralokinumab for severe, uncontrolled asthma (stratos 1 and Stratos 2): Two randomized, double blind, placebo-controlled, phase 3 clinical trials." Lancet Respir Med. Jul. 2018; 6(7):511-525.
Popovic et al. "Structural Characterisation Reveals Mechanism of IL-13-Neutralising Monoclonal Antibody Tralokinumab as Inhibition of Binding to IL-13R$\alpha$1 and IL-13R$\alpha$2." J Mol Biol. Jan. 20, 2017;429(2):208-219.
Simpson et al., "Two Phase 3 Trials of Dupilumab versus Placebo in Atopic Dermatitis" N Engl J Med. Dec. 15, 2016; 375(24):2335-2348.

(56) References Cited

OTHER PUBLICATIONS

Stadler, European Task Force on Atopic Dermatitis. "Severity scoring of atopic dermatitis: the SCORAD index. Consensus report of the European task force on atopic dermatitis" Dermatology 1993, 186(1): 23-31.

Tazawa et al., "Relative importance of IL-4 and IL-13 in lesional skin of atopic dermatitis" Arch Dermatol Res. Apr. 2004; 295(11):459-64.

Via Ritzau, "LEO Pharma announces positive top-line results for tralokinumab from three Phase 3 studies in adult patients with moderate-to-severe AD." 2019, [online] [Retrieved Jan. 14, 2021] Retrieved from the internet <https://via.ritzau.dk/pressemeddelelse/leo-pharma-announces-positive-top-line-results-for-tralokinumab-from-three-phase-3-studies-in-adult-patients-with-moderate-to-severe-ad?publisherId=12353927&releaseId=13584831>.

Ware & Sherbourne, "The MOS 36-item short-form health survey (SF-36). I. Conceptual framework and item selection" Med Care. Jun. 1992; 30(6):473-83.

Wollenberg et al., "A phase 2b Dose-ranging Efficacy and Safety study of Tralokinumab in Adult Patients with Moderate to Severe Atopic Dermatitis(AD)" Poster presented at the American Academy of Dermatology, Orlando Mar. 3-7, 2017.

Wollenberg et al., "Treatment of atopic dermatitis with tralokinumab an anti-IL-13 mAb" J. Allergy Clin. Immunol. 2019, vol. 143(1):135-141.

Wollenberg et al., Experimental Dermatology: 2018;27 (Suppl.) p. 3-58, Abstract 95, 96 and 97.

Zigmond & Snaith, "The hospital anxiety and depression scale" Acta Psychiatr. Scand. Jun. 1983; 67(6):361-70.

Wollenberg A, et al. Treatment of atopic dermatitis with tralokinumab, an anti-IL-13 mAb. Journal of Allergy and Clinical Immunology, Elsevier, Amsterdam, NL, vol. 143, No. 1, Jun. 12, 2018 (Jun. 12, 2018), pp. 135-141, XP085572598.

Simpson, E., et al. (2020). Efficacy and Safety of Tralokinumab Monotherapy in Adult Patients with Moderate-to-Severe Atopic Dermatitis: Results from Two 52-Week, Phase 3 Trials (ECZTRA 1 and ECZTRA 2). SKIN The Journal of Cutaneous Medicine, 4(6), s96. https://doi.org/10.25251/skin.4.supp.96. November issue and Poster Presentations (FC20 Dermatology Conference) Oct. 27, 2020. Retrieved from the Internet: URL:https://jofskin.org/index.php/skin/article/view/1066.

John Collett Ed—Aulton M E (Ed) 2: "Dosage Regimens", Jan. 1, 2001 (Jan. 1, 2001), Pharmaceutics. the Science of Dosage Form Design Ed. 2, Churchill Livigstone, pp. 275-288, XP003030862.

\* cited by examiner

FIGURE 5A
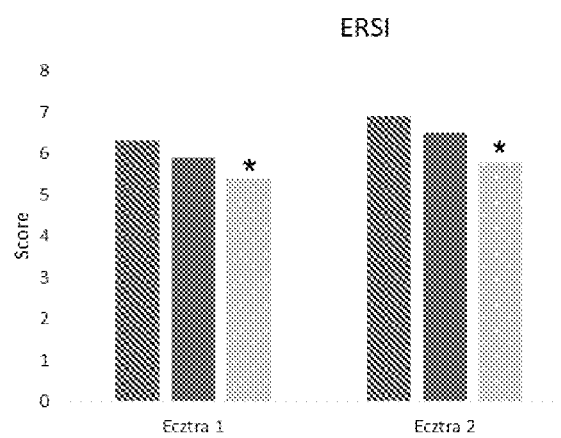
FIGURE 5B
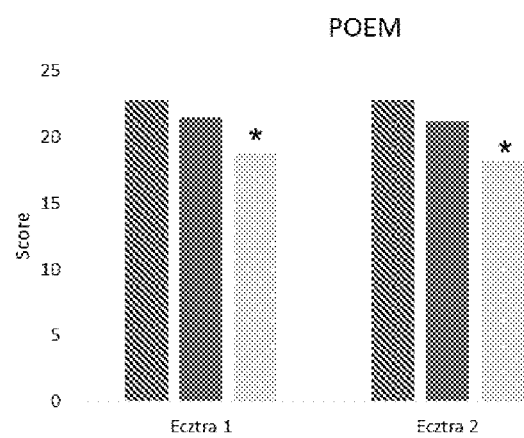
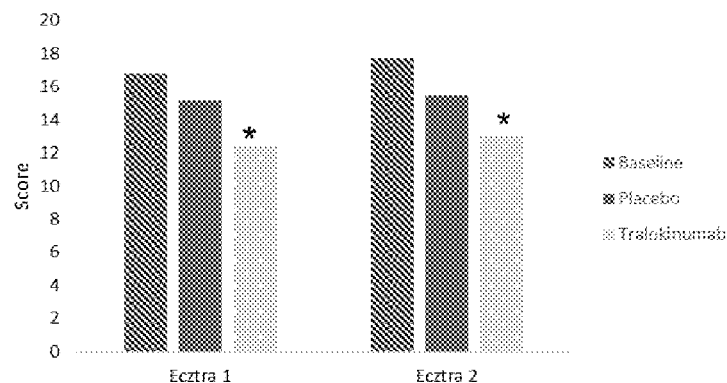
FIGURE 5C

ECZTRA 1

SCORAD

ECZTRA 2

Pruritus

DLQI

EASI

Pruritus:

```
SEQUENCE LISTING

<160> NUMBER OF SEQ ID NOS: 12

<210> SEQ ID NO 1
<211> LENGTH: 5
<212> TYPE: PRT
<213> ORGANISM: Artificial Sequence
<220> FEATURE:
<223> OTHER INFORMATION: HCDR1

<400> SEQUENCE: 1

Asn Tyr Gly Leu Ser
1               5

<210> SEQ ID NO 2
<211> LENGTH: 17
<212> TYPE: PRT
<213> ORGANISM: Artificial Sequence
<220> FEATURE:
<223> OTHER INFORMATION: HCDR2

<400> SEQUENCE: 2

Trp Ile Ser Ala Asn Asn Gly Asp Thr Asn Tyr Gly Gln Glu Phe Gln
1               5                   10                  15

Gly

<210> SEQ ID NO 3
<211> LENGTH: 13
<212> TYPE: PRT
<213> ORGANISM: Artificial Sequence
<220> FEATURE:
```

<223> OTHER INFORMATION: HCDR3

<400> SEQUENCE: 3

Asp Ser Ser Ser Ser Trp Ala Arg Trp Phe Phe Asp Leu
1               5                   10

<210> SEQ ID NO 4
<211> LENGTH: 11
<212> TYPE: PRT
<213> ORGANISM: Artificial Sequence
<220> FEATURE:
<223> OTHER INFORMATION: LCDR1

<400> SEQUENCE: 4

Gly Gly Asn Ile Ile Gly Ser Lys Leu Val His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: LCDR2

<400> SEQUENCE: 5

Asp Asp Gly Asp Arg Pro Ser
1               5

<210> SEQ ID NO 6
<211> LENGTH: 11
<212> TYPE: PRT
<213> ORGANISM: Artificial Sequence
<220> FEATURE:
<223> OTHER INFORMATION: LCDR3

<400> SEQUENCE: 6

Gln Val Trp Asp Thr Gly Ser Asp Pro Val Val
1               5                   10

<210> SEQ ID NO 7
<211> LENGTH: 366
<212> TYPE: DNA
<213> ORGANISM: Artificial Sequence
<220> FEATURE:
<223> OTHER INFORMATION: cDNA heavy chain variable domain

<400> SEQUENCE: 7

```
caggtccagc tggtgcagtc tggggctgag gtgaagaagc ctggggcctc agtgaaggtc    60
tcctgcaagg cttctggtta cacctttaca aattatggtc tcagctgggt gcgacaggcc   120
cctggacaag gcttgagtg gatgggatgg atcagcgcta ataatggcga cacaaattat   180
ggacaggaat tccagggcag agtcaccatg accacagata catccacgag cacagcctac   240
atggagttga ggagcctgag atctgacgac acggccgttt attactgtgc gagagactcc   300
agcagcagct gggcccgctg gttttttcgat ctctggggcc gggggacact ggtcaccgtc   360
tcctca                                                              366
```

<210> SEQ ID NO 8
<211> LENGTH: 122
<212> TYPE: PRT
<213> ORGANISM: Artificial Sequence
<220> FEATURE:
<223> OTHER INFORMATION: Polypeptide sequence heavy chain variable
      region

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
        35                  40                  45

Gly Trp Ile Ser Ala Asn Asn Gly Asp Thr Asn Tyr Gly Gln Glu Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Ser Ser Ser Trp Ala Arg Trp Phe Phe Asp Leu Trp
            100                 105                 110

Gly Arg Gly Thr Leu Val Thr Val Ser Ser
        115                 120

<210> SEQ ID NO 9
<211> LENGTH: 327
<212> TYPE: DNA
<213> ORGANISM: Artificial Sequence
<220> FEATURE:
<223> OTHER INFORMATION: cDNA light chain variable domain

<400> SEQUENCE: 9
tcctatgtgc tgactcagcc accctcggtg tcagtggccc caggaaagac ggccaggatt      60
acctgtgggg gaaacatcat tggaagtaaa cttgtacact ggtaccagca gaagccaggc     120
caggcccctg tgctggtcat ctatgatgat ggcgaccggc cctcaggat ccctgagcga      180 ttctctggct ccaactctgg gaacacggcc accctgacca tcagcagggt cgaggccggg     240
gatgaggccg actattattg tcaggtgtgg gatactggta gtgatcccgt ggtattcggc     300
ggagggacca agctgaccgt cctaggt                                         327

<210> SEQ ID NO 10
<211> LENGTH: 108
<212> TYPE: PRT
<213> ORGANISM: Artificial Sequence
<220> FEATURE:
<223> OTHER INFORMATION: Polypeptide sequence light chain variable
      region

<400> SEQUENCE: 10

Ser Tyr Val Leu Thr Gln Pro Pro Ser Val Ser Val Ala Pro Gly Lys
1               5                   10                  15

Thr Ala Arg Ile Thr Cys Gly Gly Asn Ile Ile Gly Ser Lys Leu Val
            20                  25                  30

His Trp Tyr Gln Gln Lys Pro Gly Gln Ala Pro Val Leu Val Ile Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Gly Ser Asp Pro
                85                  90                  95

Val Val Phe Gly Gly Gly Thr Lys Leu Thr Val Leu
            100                 105

```
<210> SEQ ID NO 11
<211> LENGTH: 449
<212> TYPE: PRT
<213> ORGANISM: Artificial Sequence
<220> FEATURE:
<223> OTHER INFORMATION: Heavy chain

<400> SEQUENCE: 11
```

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Asn | Tyr |
| | | | 20 | | | | | 25 | | | | | 30 | | |
| Gly | Leu | Ser | Trp | Val | Arg | Gln | Ala | Pro | Gly | Gln | Gly | Leu | Glu | Trp | Met |
| | | 35 | | | | | 40 | | | | | 45 | | | |
| Gly | Trp | Ile | Ser | Ala | Asn | Asn | Gly | Asp | Thr | Asn | Tyr | Gly | Gln | Glu | Phe |
| | 50 | | | | | 55 | | | | | 60 | | | | |
| Gln | Gly | Arg | Val | Thr | Met | Thr | Thr | Asp | Thr | Ser | Thr | Ser | Thr | Ala | Tyr |
| 65 | | | | | 70 | | | | | 75 | | | | | 80 |
| Met | Glu | Leu | Arg | Ser | Leu | Arg | Ser | Asp | Asp | Thr | Ala | Val | Tyr | Tyr | Cys |
| | | | | 85 | | | | | 90 | | | | | 95 | |
| Ala | Arg | Asp | Ser | Ser | Ser | Trp | Ala | Arg | Trp | Phe | Phe | Asp | Leu | Trp |
| | | | 100 | | | | | 105 | | | | | 110 | | |
| Gly | Arg | Gly | Thr | Leu | Val | Thr | Val | Ser | Ser | Ala | Ser | Thr | Lys | Gly | Pro |
| | | 115 | | | | | 120 | | | | | 125 | | | |
| Ser | Val | Phe | Pro | Leu | Ala | Pro | Cys | Ser | Arg | Ser | Thr | Ser | Glu | Ser | Thr |
| | 130 | | | | | 135 | | | | | 140 | | | | |
| Ala | Ala | Leu | Gly | Cys | Leu | Val | Lys | Asp | Tyr | Phe | Pro | Glu | Pro | Val | Thr |
| 145 | | | | | 150 | | | | | 155 | | | | | 160 |
| Val | Ser | Trp | Asn | Ser | Gly | Ala | Leu | Thr | Ser | Gly | Val | His | Thr | Phe | Pro |
| | | | | 165 | | | | | 170 | | | | | 175 | |
| Ala | Val | Leu | Gln | Ser | Ser | Gly | Leu | Tyr | Ser | Leu | Ser | Ser | Val | Val | Thr |
| | | | 180 | | | | | 185 | | | | | 190 | | |
| Val | Pro | Ser | Ser | Ser | Leu | Gly | Thr | Lys | Thr | Tyr | Thr | Cys | Asn | Val | Asp |
| | | 195 | | | | | 200 | | | | | 205 | | | |
| His | Lys | Pro | Ser | Asn | Thr | Lys | Val | Asp | Lys | Arg | Val | Glu | Ser | Lys | Tyr |
| | 210 | | | | | 215 | | | | | 220 | | | | |
| Gly | Pro | Pro | Cys | Pro | Ser | Cys | Pro | Ala | Pro | Glu | Phe | Leu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | Gln | Glu | Asp |
| | | | 260 | | | | | 265 | | | | | 270 | | |
| Pro | Glu | Val | Gln | Phe | Asn | Trp | Tyr | Val | Asp | Gly | Val | Glu | Val | His | Asn |
| | | 275 | | | | | 280 | | | | | 285 | | | |
| Ala | Lys | Thr | Lys | Pro | Arg | Glu | Glu | Gln | Phe | Asn | Ser | Thr | Tyr | Arg | Val |
| | 290 | | | | | 295 | | | | | 300 | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Gly | Leu | Pro | Ser | Ser | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Gln | Glu | Glu | Met | Thr | Lys | Asn | Gln | Val | Ser | Leu | Thr |
| | | 355 | | | | | 360 | | | | | 365 | | | |

-continued

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 12
<211> LENGTH: 214
<212> TYPE: PRT
<213> ORGANISM: Artificial Sequence
<220> FEATURE:
<223> OTHER INFORMATION: Light chain

<400> SEQUENCE: 12

Ser Tyr Val Leu Thr Gln Pro Pro Ser Val Ser Val Ala Pro Gly Lys
1               5                   10                  15

Thr Ala Arg Ile Thr Cys Gly Gly Asn Ile Ile Gly Ser Lys Leu Val
            20                  25                  30

His Trp Tyr Gln Gln Lys Pro Gly Gln Ala Pro Val Leu Val Ile Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Gly Ser Asp Pro
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

METHODS FOR TREATING ATOPIC DERMATITIS AND RELATED DISORDERS

INCORPORATION BY REFERENCE

The sequence listing entitled "38381_205_sequence_listing_012024_ST25," created on 20 Jan. 2024, and having a file size of 11 kB, is hereby incorporated by reference herein.

FIELD OF THE INVENTION

The present invention relates to methods for treating atopic dermatitis in a subject using an interleukin-13 (IL-13) binding protein, such as an anti-IL-13 antibody or an IL-13-binding fragment thereof.

BACKGROUND TO THE INVENTION

Atopic dermatitis (AD) is a heterogeneous inflammatory skin disease arising from genetic and environmental factors that disrupt skin barrier function and immune response (Leung, D. Y. and Guttman-Yassky, E. Deciphering the complexities of atopic dermatitis: shifting paradigms in treatment approaches. *J Allergy Clin Immunol.* 2014; 134: 769-779). Current management generally involves treatment combinations to suppress inflammation, restore skin barrier function, and prevent superinfection (Wollenberg, A., Oranje, A., Deleuran, M., Simon, D., Szalai, Z., Kunz, B. et al. ETFAD/EADV Eczema task force 2015 position paper on diagnosis and treatment of atopic dermatitis in adult and paediatric patients. *J Eur Acad Dermatol Venereol.* 2016; 30:729-747).

Topical corticosteroids (TCSs) are overwhelmingly the most frequently prescribed class of drugs for AD patients, although long-term application of a TCS is not recommended. Topical calcineurin inhibitors (TCI) are generally effective and safe as short-term treatments. Skin malignancies and increased risk of lymphomas have prompted regulatory authorities to require a warning regarding the long-term safety of topical tacrolimus and pimecrolimus in their prescribing information, for example. First generation antihistamines are widely prescribed for acute symptomatic treatment of pruritus (itching), although their effectiveness is limited and largely attributed to their sedating effect. Oral immunosuppressants and glucocorticoids are effective, but are sometimes associated with severe toxicity and side effects, thus limiting their use to short term and/or intermittent therapy.

Cyclosporine A (CSA), a therapy for severe AD in some territories, is an immunosuppressant affecting both humoral and cellular immune responses, which increases susceptibility to infections and decreases cancer immunosurveillance. Other commonly recognized toxicities include hypertension and impaired renal and hepatic function. In addition, CSA interacts with other commonly used drugs, potentially affecting their metabolism and effect. Systemic immunosuppressants are typically reserved for treatment of moderate-to-severe AD because of their associated with adverse events and unsuitability for long-term use (Wollenberg, A., Oranje, A., Deleuran, M., Simon, D., Szalai, Z., Kunz, B. et al. ETFAD/EADV Eczema task force 2015 position paper on diagnosis and treatment of atopic dermatitis in adult and paediatric patients. *J Eur Acad Dermatol Venereol.* 2016; 30:729-747). Therefore more effective and well-tolerated therapies are required that target the mechanisms of AD pathophysiology rather than simply providing symptom relief.

A key feature of AD is upregulation of IL-13 and interleukin-4 (IL-4) in lesional and nonlesional skin, suggesting both cytokines can contribute to AD pathogenesis (see Nomura, I., Goleva, E., Howell, M. D., Hamid, Q. A., Ong, P. Y., Hall, C. F. et al. Cytokine milieu of atopic dermatitis, as compared to psoriasis, skin prevents induction of innate immune response genes. *J Immunol.* 2003; 171:3262-3269; Tazawa, T., Sugiura, H., Sugiura, Y., and Uehara, M. Relative importance of IL-4 and IL-13 in lesional skin of atopic dermatitis. *Arch Dermatol Res.* 2004; 295:459-464). Moreover, AD severity is associated with increased IL-13 and associated chemokine mRNA and serum levels, whereas reductions in IL-13 concentrations have correlated with treatment response and improved clinical outcomes. Although treatment with dupilumab, a human mAb that inhibits both IL-4 and IL-13 signaling, has demonstrated improvements in AD symptoms, the relative contribution of each of these cytokines to AD pathogenesis was unclear.

IL-13 is a 114 amino acid cytokine with an unmodified molecular mass of approximately 12 kDa. IL-13 is most closely related to IL-4 with which it shares 30% sequence homology at the amino acid level. The human IL-13 gene is located on chromosome 5q31 adjacent to the IL-4 gene. Although initially identified as a Th2 CD4+ lymphocyte derived cytokine, IL-13 is also produced by Th1 CD4+ T-cells, CD8+ T lymphocytes NK cells, and non-T-cell populations such as mast cells, basophils, eosinophils, macrophages, monocytes and airway smooth muscle cells. IL-13 has been linked with a number of diseases, in particular, diseases which are caused by an inflammatory response. For example, administration of recombinant IL-13 to the airways of naive non-sensitised rodents was shown to cause many aspects of the asthma phenotype including airway inflammation, mucus production and airways hyper-responsiveness. A similar phenotype was observed in a transgenic mouse in which IL-13 was specifically overexpressed in the lung. In this model, more chronic exposure to IL-13 also resulted in fibrosis.

A number of genetic polymorphisms in the IL-13 gene have also been linked to allergic diseases. In particular, a variant of the IL-13 gene in which the arginine residue at amino acid 130 is substituted with glutamine (Q130R) has been associated with bronchial asthma, atopic dermatitis and raised serum IgE levels. This particular IL-13 variant is also referred to as the Q110R variant (arginine residue at amino acid 110 is substituted with glutamine) by some groups who exclude the 20 amino acid signal sequence from the amino acid count.

Tralokinumab (also known as CAT-354 and BAK502G9) is a fully human therapeutic antibody that binds to and neutralizes IL-13, including the Q130R variant (see Popovic et al. *J. Mol. Biol.* (2017) 429 (2): 208-219; May, R. D., Monk, P. D., Cohen, E. S., Manuel, D., Dempsey, F., Davis, N. H. et al. Preclinical development of CAT-354, an IL-13 neutralizing antibody, for the treatment of severe uncontrolled asthma. *Br J Pharmacol.* 2012; 166:177-193).

Tralokinumab has previously been tested in phase 2b study of 204 adults for the treatment of AD—where patients received 45 mg, 150 mg, or 300 mg of subcutaneous tralokinumab, or placebo, every 2 weeks for 12 weeks with concomitant topical glucocorticoids—and was found to improve change from baseline in Eczema Area Severity Index (EASI) score, together with improvements in Scoring atopic dermatitis (SCORAD), Dermatology Life Quality Index (DLQI), and pruritus numeric rating scale scores, as compared to placebo (Wollenberg *J. Allergy Clin. Immunol.* (2019) 143 (1): 135-141).

There remains a desire in the art for further and improved treatments for AD that address, for example, at least some of the concerns referred to above.

SUMMARY OF THE INVENTION

The inventors have found that a patient's response to an IL-13 binding protein (e.g. an anti-IL13 antibody like tralokinumab) is maintained when the dosing frequency of the antibody is decreased. Numerous advantages are associated with reducing dosing frequency, for example, improved patient compliance (e.g. less injections), reduction in the total amount of drug required per patient, and reduced clinician involvement (if, for example, the treatment cannot be self-administered). Patients can sometimes develop antibodies to a therapeutic protein, which neutralise the therapeutic effect. This tends not to be an issue for short term use (e.g. cancer therapy), but the likelihood increases with duration of use and drug exposure. Reducing drug exposure through dosing frequency may help prevent this effect. Increased drug exposure also increases the likelihood of side effects. Reduced dosing frequency may reduce side effects. It follows that tolerability (the balance between the efficacy of a therapeutic and its side effects) can also be improved.

Thus, in one aspect, the invention provides an interleukin-13 (IL-13) binding protein (e.g. an anti-IL-13 antibody or an IL-13-binding fragment thereof) for use in a method of treating atopic dermatitis in a subject, wherein the method comprises the steps of: (a) administering a first dose of the IL-13 binding protein to the subject; and (b) administering one or more secondary dose(s) of the IL-13 binding protein to the subject, wherein each secondary dose is administered to the subject from 15 days to 35 days after the immediately preceding dose.

In another aspect, the invention provides a method of treating atopic dermatitis in a subject in need thereof, wherein the method comprises the steps of: (a) administering a first dose of an IL-13 binding protein (e.g. an anti-IL-13 antibody or an IL-13-binding fragment thereof) to the subject; and (b) administering one or more secondary dose(s) of the IL-13 binding protein to the subject, wherein each secondary dose is administered to the subject from 15 days to 35 days after the immediately preceding dose.

In a further aspect, the invention provides a use of an IL-13 binding protein (e.g. an anti-IL-13 antibody or an IL-13-binding fragment thereof) in the manufacture of a medicament for treating atopic dermatitis in a subject, wherein the method comprises the steps of: (a) administering a first dose of the IL-13 binding protein to the subject; and (b) administering one or more secondary dose(s) of the IL-13 binding protein to the subject, wherein each secondary dose is administered to the subject from 15 days to 35 days after the immediately preceding dose.

In another aspect, the invention provides an interleukin-13 (IL-13) binding protein for use in a method of treating a skin infection in a subject with moderate-to-severe or severe AD, wherein the method comprises administering the IL-13 binding protein to the subject. Preferably, the IL-13 binding protein is not administered in combination with a topical corticosteroid.

In another aspect, the invention provides an interleukin-13 (IL-13) binding protein for use in a method of treating a skin infection in a subject, wherein the method comprises the steps of: (a) selecting a subject with moderate-to-severe or severe AD and having a microbial skin infection; and (b) administering the IL-13 binding protein to the subject. Preferably, the IL-13 binding protein is not administered in combination with a topical corticosteroid.

In another aspect, the invention provides a method of treating a skin infection in a subject with moderate-to-severe or severe AD, wherein the method comprises administering the IL-13 binding protein to the subject. Preferably, the IL-13 binding protein is not administered in combination with a topical corticosteroid.

In another aspect, the invention provides a method of treating a skin infection in a subject, wherein the method comprises the steps of: (a) selecting a subject with moderate-to-severe or severe AD and having a microbial skin infection; and (b) administering the IL-13 binding protein to the subject. Preferably, the IL-13 binding protein is not administered in combination with a topical corticosteroid.

In another aspect, the invention provides a use of an IL-13 binding protein in the manufacture of a medicament for treating a skin infection in a subject with moderate-to-severe or severe AD, wherein the method comprises administering the IL-13 binding protein to the subject. Preferably, the IL-13 binding protein is not administered in combination with a topical corticosteroid.

In another aspect, the invention provides a use of an IL-13 binding protein in the manufacture of a medicament for treating a skin infection in a subject, wherein the method comprises the steps of: (a) selecting a subject with moderate-to-severe or severe AD and having a microbial skin infection; and (b) administering the IL-13 binding protein to the subject. Preferably, the IL-13 binding protein is not administered in combination with a topical corticosteroid.

In another aspect, the invention provides an IL-13 binding protein for use in a method of treating pruritus in a subject with moderate-to-severe or severe AD, wherein the method comprises administering the IL-13 binding protein to the subject. Preferably, the IL-13 binding protein is not administered in combination with a topical corticosteroid.

In another aspect, the invention provides an IL-13 binding protein for use in a method of treating pruritus in a subject, wherein the method comprises the steps of: (a) selecting a subject with moderate-to-severe or severe AD and experiencing pruritus; and (b) administering the IL-13 binding protein to the subject. Preferably, the IL-13 binding protein is not administered in combination with a topical corticosteroid.

In another aspect, the invention provides a method of treating pruritus in a subject with moderate-to-severe or severe AD, wherein the method comprises administering the IL-13 binding protein to the subject. Preferably, the IL-13 binding protein is not administered in combination with a topical corticosteroid. In another aspect, the invention provides a method of treating pruritus in a subject, wherein the method comprises the steps of: (a) selecting a subject with moderate-to-severe or severe AD and experiencing pruritus; and (b) administering the IL-13 binding protein to the subject. Preferably, the IL-13 binding protein is not administered in combination with a topical corticosteroid.

In another aspect, the invention provides a use of an IL-13 binding protein in the manufacture of a medicament for treating pruritus in a subject with moderate-to-severe or severe AD, wherein the method comprises administering the IL-13 binding protein to the subject. Preferably, the IL-13 binding protein is not administered in combination with a topical corticosteroid.

In another aspect, the invention provides a use of an IL-13 binding protein in the manufacture of a medicament for treating pruritus in a subject, wherein the method comprises the steps of: (a) selecting a subject with moderate-to-severe or severe AD and experiencing pruritus; and (b) administering the IL-13 binding protein to the subject. Preferably, the IL-13 binding protein is not administered in combination with a topical corticosteroid.

In another aspect, the invention provides an IL-13 binding protein for use in a method of treating eczema-related sleep interference in a subject with moderate-to-severe or severe AD, wherein the method comprises administering the IL-13 binding protein to the subject. Preferably, the IL-13 binding protein is not administered in combination with a topical corticosteroid.

In another aspect, the invention provides an IL-13 binding protein for use in a method of treating eczema-related sleep interference in a subject, wherein the method comprises the steps of: (a) selecting a subject with moderate-to-severe or severe AD and experiencing eczema-related sleep interference; and (b) administering the IL-13 binding protein to the subject.

In another aspect, the invention provides a method of treating eczema-related sleep interference in a subject with moderate-to-severe or severe AD, wherein the method comprises administering the IL-13 binding protein to the subject. Preferably, the IL-13 binding protein is not administered in combination with a topical corticosteroid.

In another aspect, the invention provides a method of treating eczema-related sleep interference in a subject, wherein the method comprises the steps of: (a) selecting a subject with moderate-to-severe or severe AD and experiencing eczema-related sleep interference; and (b) administering the IL-13 binding protein to the subject.

In another aspect, the invention provides a use of an IL-13 binding protein in the manufacture of a medicament for treating eczema-related sleep interference in a subject with moderate-to-severe or severe AD, wherein the method comprises administering the IL-13 binding protein to the subject. Preferably, the IL-13 binding protein is not administered in combination with a topical corticosteroid.

In another aspect, the invention provides a use of an IL-13 binding protein in the manufacture of a medicament for treating eczema-related sleep interference in a subject, wherein the method comprises the steps of: (a) selecting a subject with moderate-to-severe or severe AD and experiencing eczema-related sleep interference; and (b) administering the IL-13 binding protein to the subject.

In another aspect, the invention provides an IL-13 binding protein for use in a method of treating anxiety and/or depression in a subject with moderate-to-severe or severe AD, wherein the method comprises administering the IL-13 binding protein to the subject. In some embodiments, the subject may have a baseline HADS score of ≥8.

In another aspect, the invention provides an IL-13 binding protein for use in a method of treating anxiety and/or depression in a subject, wherein the method comprises the steps of: (a) selecting a subject with moderate-to-severe or severe AD and experiencing anxiety and/or depression; and (b) administering the IL-13 binding protein to the subject. In some embodiments, the subject may have a baseline HADS score of ≥8.

In another aspect, the invention provides a method of treating anxiety and/or depression in a subject with moderate-to-severe or severe AD, wherein the method comprises administering the IL-13 binding protein to the subject. In some embodiments, the subject may have a baseline HADS score of ≥8.

In another aspect, the invention provides a method of treating anxiety and/or depression in a subject, wherein the method comprises the steps of: (a) selecting a subject with moderate-to-severe or severe AD and experiencing anxiety and/or depression; and (b) administering the IL-13 binding protein to the subject. In some embodiments, the subject may have a baseline HADS score of ≥8.

In another aspect, the invention provides a use of an IL-13 binding protein in the manufacture of a medicament for treating anxiety and/or depression in a subject with moderate-to-severe or severe AD, wherein the method comprises administering the IL-13 binding protein to the subject. In some embodiments, the subject may have a baseline HADS score of ≥8.

In another aspect, the invention provides a use of an IL-13 binding protein in the manufacture of a medicament for treating anxiety and/or depression in a subject, wherein the method comprises the steps of: (a) selecting a subject with moderate-to-severe or severe AD and experiencing anxiety and/or depression and (b) administering the IL-13 binding protein to the subject. In some embodiments, the subject may have a baseline HADS score of ≥8.

In another aspect, the invention provides an IL-13 binding protein for use in a method of improving health status and/or quality of life in a subject with moderate-to-severe or severe AD, wherein the method comprises administering the IL-13 binding protein to the subject. In some embodiments, an improvement in the health status and/or quality of life of the subject may be determined by an increase in the subject's (i) SF-36 score, for example SF-36 physical component score and/or SF-36 mental component score (ii) EQ-5D-5L score, (iii) DLQI score and/or PGI-B score.

In another aspect, the invention provides an IL-13 binding protein for use in a method of improving health status and/or quality of life in a subject, wherein the method comprises the steps of: (a) selecting a subject with moderate-to-severe or severe AD and experiencing reduced health status and/or quality of life; and (b) administering the IL-13 binding protein to the subject. In some embodiments, an improvement in the health status and/or quality of life of the subject may be determined by an increase in the subject's (i) SF-36 score, for example physical component score and/or SF-36 mental component score (ii) EQ-5D-5L score, (iii) DLQI score and/or PGI-B score.

In another aspect, the invention provides a method of improving health status and/or quality of life in in a subject with moderate-to-severe or severe AD, wherein the method comprises administering the IL-13 binding protein to the subject. In some embodiments, an improvement in the health status and/or quality of life of the subject may be determined by an increase in the subject's (i) SF-36 score, for example SF-36 physical component score and/or SF-36 mental component score (ii) EQ-5D-5L score, (iii) DLQI score and/or PGI-B score.

In another aspect, the invention provides a method of improving health status and/or quality of life in in a subject, wherein the method comprises the steps of: (a) selecting a subject with moderate-to-severe or severe AD and experiencing reduced health status and/or quality of life; and (b) administering the IL-13 binding protein to the subject. In some embodiments, an improvement in the health status and/or quality of life of the subject may be determined by an increase in the subject's (i) SF-36 score, for example SF-36 physical component score and/or SF-36 mental component score (ii) EQ-5D-5L score, (iii) DLQI score and/or PGI-B score.

In another aspect, the invention provides a use of an IL-13 binding protein in the manufacture of a medicament for improving health status and/or quality of life in a subject with moderate-to-severe or severe AD, wherein the method comprises administering the IL-13 binding protein to the subject. In some embodiments, an improvement in the health status and/or quality of life of the subject may be determined by an increase in the subject's (i) SF-36 score, for example SF-36 physical component score and/or SF-36 mental component score (ii) EQ-5D-5L score, (iii) DLQI score and/or PGI-B score.

In another aspect, the invention provides a use of an IL-13 binding protein in the manufacture of a medicament for improving health status and/or quality of life in a subject, wherein the method comprises the steps of: (a) selecting a subject with moderate-to-severe or severe AD and experiencing reduced health status and/or quality of life and (b) administering the IL-13 binding protein to the subject. In some embodiments, an improvement in the health status and/or quality of life of the subject may be determined by an increase in the subject's (i) SF-36 score, for example SF-36 physical component score and/or SF-36 mental component score (ii) EQ-5D-5L score, (iii) DLQI score and/or PGI-B score.

DESCRIPTION OF FIGURES

FIG. 5A. Scores for patient reported outcomes at baseline and following 2 weeks of treatment tralokinumab monotherapy or placebo (control) in two trials, ECZTRA 1 and ECZTRA 2. *=significant difference compared to control (p<0.05). ERSI=Eczema-Related Sleep Interference scores.

FIG. 5B. Scores for patient reported outcomes at baseline and following 2 weeks of treatment tralokinumab monotherapy or placebo (control) in two trials, ECZTRA 1 and ECZTRA 2. *=significant difference compared to control (p<0.05). POEM=Patient-Oriented Eczema Measure scores.

FIG. 5C. Scores for patient reported outcomes at baseline and following 2 weeks of treatment tralokinumab monotherapy or placebo (control) in two trials, ECZTRA 1 and ECZTRA 2. *=significant difference compared to control (p<0.05). DLQI=Dermatology Life Quality Index scores.

DETAILED DESCRIPTION

Figure 1:
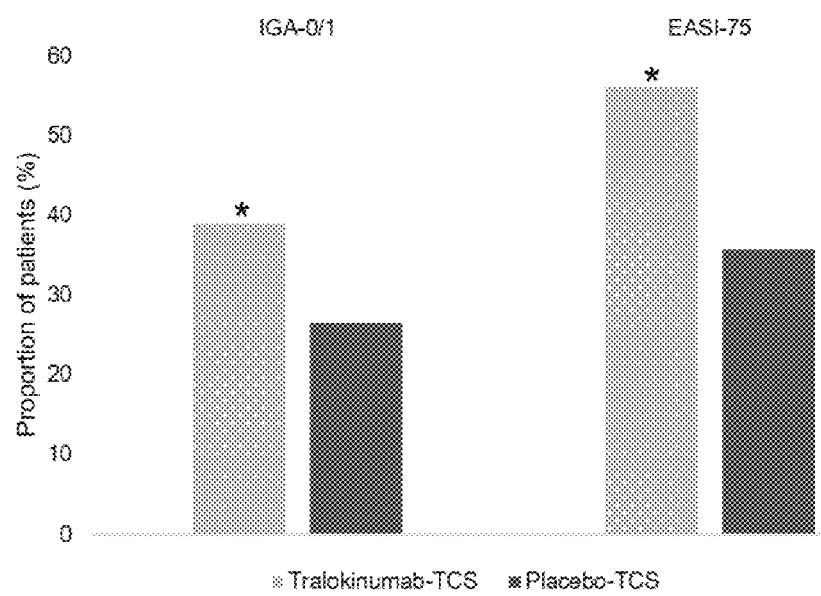
FIG. 1. Proportion of patients (%) achieving IGA-0/1 and EASI-75 following 16 weeks treatment with tralokinumab/TCS or placebo/TCS (control). *=significant difference compared to control (p<0.05).

The invention relates to methods for treating atopic dermatitis in a subject using an interleukin-13 (IL-13) binding protein (e.g. an anti-IL-13 antibody or an IL-13-binding fragment thereof).

Atopic Dermatitis

"Atopic dermatitis" (AD), as used herein, means an inflammatory skin disease characterized by intense pruritus (e.g. severe itch) and by scaly and dry eczematous lesions.

The term "atopic dermatitis" includes AD caused by or associated with epidermal barrier dysfunction, allergy (e.g. allergy to certain foods, pollen, maid, dust mite, animals, etc.), radiation exposure, and/or asthma. In some embodiments, the present invention relates to moderate-to-severe or severe AD.

As used herein, "moderate-to-severe AD" is characterized by intensely pruritic, widespread skin lesions that are often complicated by persistent bacterial, viral or fungal infections. Moderate-to-severe AD also includes chronic AD. In many cases, the chronic lesions include thickened plaques of skin, lichenification and fibrous papules. In general, patients affected by moderate-to-severe AD also have more than 20% of the body's skin affected, or 10% of skin area in addition to involvement of the eyes, hands and body folds. Moderate-to-severe AD is also considered to be present in patients who frequently require treatment with a topical corticosteroid. In the clinical studies reported herein a subject with "moderate to severe AD" was a subject having an IGA score of 3-4.

As used herein, "severe AD" refers to chronic relapsing AD that is refractory to treatment with medium-potency and high-potency TCS and/or immunosuppressant therapy. Severe AD is also characterized by chronic intensely pruritic lesions affecting more than 20% of the body surface area. Severe AD can be considered to be present in subjects with chronic AD according to the Eichenfield criteria (Eichenfield et al 2014, J. Am. Acad. Dermatol. 70:338-351), for which treatment with a potent topical corticosteroid (TCS) is indicated, and/or where the subject is resistant to treatment with a systemic corticosteroid and/or non-steroidal immunosuppressant. In the clinical studies reported herein a subject with "severe AD" was a subject having an IGA score of 4. Thus, in certain embodiments, the method treats severe AD in a subject, where the subject has an IGA score of 4 at baseline.

Treatment of AD

The methods described herein treat AD. Generally, the terms "treat", "treating", "treatment", or the like, mean to alleviate (reduce, minimise, or eliminate) symptoms, or to reduce, minimise or eliminate the causation of symptoms either on a temporary or permanent basis.

AD-Associated Parameters

Various AD-associated parameters are available to measure the severity of AD and the impact of a drug on AD. These include Investigators Global Assessment (IGA); Eczema Area and Severity Index (EASI); SCORing Atopic Dermatitis (SCORAD); and/or pruritus Numeric Rating Scale (NRS). The methods described herein may improve in an AD-associated parameter in the subject. Alternately, the methods may maintain improvement in an AD-associated parameter in the subject. The AD-associated parameter may be selected from: Investigators Global Assessment (IGA); Eczema Area and Severity Index (EASI); Scoring atopic dermatitis (SCORAD); and/or pruritus Numeric Rating Scale (NRS).

The IGA is an instrument used in clinical trials to rate the severity of the subject's global AD and is based on a 5-point scale ranging from 0 (clear) to 4 (severe) based on the condition of the disease at the time of evaluation.

| Score | Disease severity | Standard IGA scale | IGA morphological descriptors |
|---|---|---|---|
| 0 | Clear | No inflammatory signs of atopic dermatitis | No erythema and no elevation (papulation/infiltration). |
| 1 | Almost clear | Just perceptible erythema, and just perceptible papulation/infiltration | Barely perceptible erythema and/or minimal lesion elevation (papulation/infiltration) that is not widespread. |
| 2 | Mild disease | Mild erythema and mild papulation/infiltration | Visibly detectable, light pink erythema and very slight elevation (papulation/infiltration). |
| 3 | Moderate disease | Moderate erythema and moderate papulation/infiltration | Dull red, clearly distinguishable erythema and clearly perceptible but not extensive elevation (papulation/infiltration). |
| 4 | Severe disease | Severe erythema and severe papulation/infiltration | Deep/dark red erythema, marked and extensive elevation (papulation/infiltration). |

The EASI is a validated measure used in clinical practice and clinical trials to assess the severity and extent of AD (Hanifin et al. "*The eczema area and severity index (EASI): assessment of reliability in atopic dermatitis. EASI Evaluator Group. Experimental dermatology*" (2001) 10 (1): 11-18). SCORAD is one of the most commonly used disease severity scores in clinical trials with AD and in clinical practice (see "*European Task Force on Atopic Dermatitis. Severity scoring of atopic dermatitis: the SCORAD index. Consensus report of the European task force on atopic dermatitis*" Dermatology (1993) 186 (1): 23-31).

Worst Daily Pruritus NRS is established according to FDA and EMA recommendations (see, e.g. FDA "*The Food and Drug Administration. Guidance for Industry. Patient-Reported Outcome Measures: Use in Medical Product Development to Support Labeling Claims.* 2009" and EMA "*Reflection paper on the regulatory guidance for the use of health-related quality of life (HRQOL) measures in the evaluation of medicinal products. EMEA/CHMP/EWP/139391/2004.* 2005). For pruritus NRS, a subject assesses their worst itch severity over the past 24 hours using an 11 point NRS ("Worst Daily Pruritus NRS") from 0 (no itch) to 10 (worst itch imaginable).

For each AD-associated parameter the improvement or maintained improvement is measured relative to baseline. An improvement in this context can be a reduction in IGA score, a reduction in EASI score, a reduction in SCORAD score (where >50 severe, 25-50 is moderate, <25 is mild), reduction in pruritus NRS score, where each score is compared to baseline.

The baseline is an initial measurement of an AD-associated parameter or patient-related outcome (or any other parameter) that is taken before initiation of treatment by the method described herein, i.e. a measurement taken before the "baseline dose" (defined elsewhere).

An Investigator's Global Assessment 0 or 1 (IGA 0/1; clear or almost clear skin) and/or ≥75% improvement of Eczema Area and Severity Index (EASI-75) are the regulatory primary efficacy endpoints in Phase 3 clinical trials in AD. Thus, the methods described herein may preferably achieve or maintain an Investigator's Global Assessment (IGA) score of 0 or 1 and/or ≥75% improvement of Eczema Area and Severity Index (EASI-75) over baseline (e.g. as shown in Examples 1 and 4 herein). In some embodiments, the methods may achieve or maintain a ≥50% improvement of Eczema Area and Severity Index (EASI-50) over baseline (e.g. as shown in Example 3).

Additionally, or alternatively, the methods described herein may improve at least one patient-related outcome (PRO) selected from the group consisting of: worst daily pruritus Numerical Rating Scale (NRS) (see pruritus NRS discussed above), eczema-related sleep interference, Patient Oriented Eczema Measure (POEM), Dermatology Life Quality Index (DLQI), Patient Global Impression of Bother (PGI-B), Hospital Anxiety and Depression Scale (HADS), Short Form (36) Health Survey (SF-36) and EuroQOL 5-Dimension Health Questionnaire 5 Level (EQ-5D-5L).

For eczema-related sleep interference NRS, a subject rates how much their eczema interfered with their sleep the previous night using an 11 point NRS from 0 (no interference) to 10 (complete interference). The POEM is a validated questionnaire used to assess disease symptoms in AD patients in both clinical practice and clinical trials (see Charman et al. "*The patient-oriented eczema measure: development and initial validation of a new tool for measuring atopic eczema severity from the patients perspective*" Arch Dermatol. (2004) 140 (12): 1513-1519). DLQI is a patient-reported validated questionnaire with content specific to subjects with dermatology conditions (see Finlay et al. "*Dermatology Life Quality Index (DLQI)—a simple practical measure for routine clinical use*" Clin Exp Dermatol. (1994) 19 (3): 210-216). The Patient Global Impression of Bother (PGI-B) is designed to capture the subject's perception of how bothered they have been by their AD over the past 24 hours at the time of completion. A 5-point categorical response scale will be used ('not at all', 'slightly', 'somewhat', 'a lot', 'very much'). The Hospital Anxiety and Depression Scale (HADS) is a Likert-scale tool widely used to detect states of anxiety and depression in a general hospital setting ((see Zigmond A S, Snaith R P. "*The hospital anxiety and depression scale*". Acta Psychiatr Scand. 1983; 67 (6): 361-70). The tool consists of 14 items that assess the subject's anxiety (7 items) and depression (7 items) during the last week. Each item is scored from 0 to 3, with high scores indicating more severe anxiety or depression. Short Form (36) Health Survey (SF-36) is a patient-reported survey designed to evaluate health status by generating scores for 8 health domains (physical functioning, role physical, bodily pain, general health, vitality, social functioning, role emotional, and mental health) and 2 psychometrically derived summary scores (a physical component summary and a mental component summary). (see Ware J E J, Sherbourne C D. "*The MOS 36-item short-form health survey (SF-36). I. Conceptual framework and item selection*" Med Care. 1992; 30 (6): 473-83). EuroQoL 5-Dimension Health Questionnaire 5 Level (EQ-5D-5L) is a standardised measure of health status developed by the EuroQoL group to provide a simple, generic measure of health for clinical and economic appraisal (see Greiner W et al. "*A single European currency for EQ-5D health states. Results from a six-country study*" The European journal of health economics: HEPAC: health economics in prevention and care. 2003; 4 (3): 222-31). The EQ-5D-5L is a self-administered questionnaire used to assess health status 'today' and is divided into 2 sections: The first section includes 5 dimensions (mobility, self-care, usual activity, pain/discomfort, and anxiety/depression); each dimension is assessed by the subject using a 5-point scale ('no problems', 'slight problems', 'moderate problems', 'severe problems', and 'extreme problems'). The second section consists of a vertical visual analogue scale anchored at 0 ('the worst health you can imagine') and 100 ('the best health you can imagine').

The methods may maintain improvement in at least one patient-related outcome (PRO) selected from the group consisting of: worst daily pruritus Numerical Rating Scale (NRS), eczema-related sleep interference, Patient Oriented Eczema Measure (POEM), Dermatology Life Quality Index (DLQI), Patient Global Impression of Bother (PGI-B), Hospital Anxiety and Depression Scale (HADS), Short Form (36) Health Survey (SF-36) and EuroQoL 5-Dimension Health Questionnaire 5 Level (EQ-5D-5L). For each PRO, the improvement or maintained improvement is relative to baseline. An improvement in this context can be a reduction (e.g. a ≥3 point reduction) in the PRO score (or, for example, a ≥4 point reduction for DLQI), where the score is compared to baseline.

In some embodiments, the method described herein may achieve: (a) ≥50% improvement of Eczema Area and Severity Index (EASI-50); (b) ≥2 point reduction of IGA score; (c) ≥ 3 point reduction in pruritus NRS; (d) ≥4 point reduction in POEM score; (e) ≥4 point reduction in DLQI score; (f) ≥0.4 point reduction in eczema-related sleep interference; (g) ≥1-point reduction in PGI-B score; (h) ≥2 point or ≥3 point reduction in HADS score (i) ≥4 point increase in SF-36 Physical Component Summary Score and/or ≥2 point increase in SF-36 Mental Component Summary Score; and/or (j) ≥0.2 point increase in EQ-5D-5L index score. In some embodiments, the method may maintain: (a) ≥50% improvement of Eczema Area and Severity Index (EASI-50); (b) ≥2 point reduction of IGA score; (c) ≥3 point reduction in pruritus NRS; (d) ≥4 point reduction in POEM score; (e) ≥4 point reduction in DLQI score; (f) ≥0.4 point reduction in eczema-related sleep interference; (g) ≥1-point reduction in PGI-B score; (h) ≥2 point or ≥3 point point reduction in HADS score; (i) ≥4 point increase in SF-36 Physical Component Summary Score and/or ≥2 point increase in SF-36 Mental Component Summary Score; and/or (j) ≥0.2 point increase in EQ-5D-5L index score.

For example, the methods described herein may achieve one or more (in particular all) of the following: (a) ≥50% improvement of Eczema Area and Severity Index (EASI-50); (b) ≥2 point reduction of IGA score; (c) ≥4 point reduction in POEM score; and (d) ≥4 point reduction in DLQI score. The methods may maintain one or more (or all) of the following: (a) ≥50% improvement of Eczema Area and Severity Index (EASI-50); (b) ≥2 point reduction of IGA score; (c) ≥4 point reduction in POEM score; and (d) ≥4 point reduction in DLQI score.

In preferred embodiments, the method described herein may achieve: (a) ≥4 point reduction in pruritus NRS; (b) ≥4 point reduction in POEM score; (c) ≥4 point reduction in DLQI score; and/or (d) ≥2 point reduction in eczema-related sleep interference (e.g. after 2 or 3 weeks, as illustrated in Example 2).

In preferred embodiments, the method described herein may achieve: (a) ≥50% improvement of Eczema Area and Severity Index (EASI-50); (b) ≥3 point reduction in pruritus NRS; (c) ≥4 point reduction in POEM score; (d) ≥4 point reduction in DLQI score; and/or (e) ≥1-point reduction in PGI-B score (e.g. after 12 weeks, as illustrated in Example 3).

In preferred embodiments, the method described herein may achieve: (a) ≥50% improvement of Eczema Area and Severity Index (EASI-50); and/or (b) ≥75% improvement of Eczema Area and Severity Index (EASI-75) (e.g. after 24 weeks, as illustrated in Example 3).

In preferred embodiments, the method described herein may achieve: (a) ≥4 point reduction in pruritus NRS; (b) ≥4 point reduction in POEM score; (c) ≥4 point reduction in DLQI score; and/or (d) ≥around 1 point reduction in eczema-related sleep interference (e.g. after 2 or 3 weeks, as illustrated in Example 5).

In preferred embodiments, the method described herein may achieve: (a) ≥2 point reduction or ≥3 point reduction in HADS score; (b) ≥4 point increase in SF-36 Physical Component Summary Score and/or ≥2 point increase in SF-36 Mental Component Summary Score; and/or (c) ≥0.2 point increase in EQ-5D-5L index score (e.g. after 16 weeks, as illustrated in Examples 9 and 10).

In some instances, the methods may achieve one, two, three, four, five, six, seven, eight, nine or all of the following: (a) ≥50% improvement of Eczema Area and Severity Index (EASI-50); (b) ≥2 point reduction of IGA score; (c) ≥3 point reduction in pruritus NRS; (d) ≥4 point reduction in POEM score; (e) ≥4 point reduction in DLQI score; (f) ≥0.4 point reduction in eczema-related sleep interference; (g) ≥1-point reduction in PGI-B score (e.g. as illustrated in Examples 1-3); (h) ≥2 point or ≥3 point reduction in HADS score; (i) ≥4 point increase in SF-36 Physical Component Summary Score and/or ≥2 point increase in SF-36 Mental Component Summary Score; and/or (j) ≥0.2 point increase in EQ-5D-5L index score.

In some instances, the methods described herein may maintain one, two, three, four, five, six, seven, eight, nine or all of the following: (a) ≥50% improvement of Eczema Area and Severity Index (EASI-50); (b) ≥2 point reduction of IGA score; (c) ≥3 point reduction in pruritus NRS; (d) ≥4 point reduction in POEM score; (e) ≥4 point reduction in DLQI score; (f) ≥0.4 point reduction in eczema-related sleep interference; (g) ≥1-point reduction in PGI-B score; (h) ≥2 point or ≥3 point reduction in HADS score; (i) ≥4 point increase in SF-36 Physical Component Summary Score and/or ≥2 point increase in SF-36 Mental Component Summary Score; and/or (j) ≥0.2 point increase in EQ-5D-5L index score.

TCS Dependence

Long-term application of a TCS is not recommended because of the risk of skin atrophy, dyspigmentation, acneiform eruptions, and risks associated with systemic absorption (e.g. hypothalamic pituitary axis effects, Cushing's disease, etc.). Repeated application of any topical therapy over a long period of time or to large surface areas can also lead to reduced patient compliance.

The methods described herein may reduce the topical corticosteroid (TCS) dependence of the subject with AD (especially moderate-to-severe or severe AD).

Reduced dependence may be assessed by comparing the cumulative amount (in grams) of a formulation containing TCS applied by a subject after initiation of a method described herein over a particular time interval (e.g. 16 weeks), as compared to a placebo-treated subject. For example, a subject may use at least 0.2 g less, at least 0.3 g less, at least 0.4 g less or at least 0.5 g less TCS per day, as compared to a placebo-treated subject. Typically, a subject may use at least 0.5 g less TCS per day, as compared to a placebo-treated subject (e.g. as in Example 1).

Reduced dependence may also be assessed by the number of TCS-free days (which may still include lower potency TCS and TCI) after initiation of the method, as compared to the same measurement performed at baseline.

A TCS can be classified as group I, group II, group III and group IV topical corticosteroid. According to the Anatomical Therapeutic Classification System of World Health Organization, corticosteroids are classified as weak/lower potency (group I), moderately potent (group II) and potent (group III) and very potent (group IV), based on their activity as compared to hydrocortisone. Group IV TCS (very potent) are up to 600 times as potent as hydrocortisone and include clobetasol propionate and halcinonide. Group III TCS (potent) are 50 to 100 times as potent as hydrocortisone and include betamethasone valerate, betamethasone dipropionate, diflucortolone valerate, hydrocortisone-17-butyrate, mometasone furoate, and methylprednisolone aceponate. Group II TCS (moderately potent) are 2 to 25 times as potent as hydrocortisone and include clobetasone butyrate, and triamcinolone acetonide. Group I TCS (mild) includes hydrocortisone.

The term "TCS-free day" means a day in which the subject does not use a TCS of Group II, Group III or Group IV.

For example, the subject the number of TCS-free days may increase by about 0.5 day, about 0.75 day, about 1 day, about 1.5 days, about 2 days, about 3 days or more averaged over a week, as compared to a placebo-treated subject. Typically, the number of TCS-free days may increase by about 0.5 day, as compared to a placebo-treated subject (e.g. as illustrated in Example 1).

As shown in the examples below, the IL-13 binding protein can be administered as a monotherapy, i.e. without TCS, as so can be used to wean a subject off TCS use. Accordingly, in the methods described herein a medium-potency or high-potency TCS may be administered alongside the IL-13 binding protein. The amount of TCS can then be reduced by at least 20%, at least 30%, at least 40%, at least 50%, at least 60%, at least 70%, at least 80%, at least 90%, at least 95%, or around 100% after initiation of the method (e.g. over a 3-4 month period), as compared to the amount of TCS at baseline.

Treatment of a Skin Infection

In some aspects, the methods described herein treat a skin infection. Generally, the terms "treat", "treating", "treatment", or the like, mean to alleviate (reduce, minimise, or eliminate) symptoms, or to reduce, minimise or eliminate the causation of symptoms either on a temporary or permanent basis.

The patient to be treated has a microbial skin infection, such as a bacterial infection, a fungal infection or a viral infection. For example, the skin infection may be *Staphylococcus aureus* infection, *Streptococcus* infection, impetigo, cellulitis, infected dermatitis, eczema herpeticum, folliculitis, infected blister, mycosis and tinea *versicolor*.

In some embodiments, the IL-13 binding protein is not administered in combination with a topical corticosteroid. "Not administered in combination with" means "not administered in the same course of treatment". In some embodiments, the IL-13 binding protein is administered as a monotherapy for treating skin infection in a subject having moderate to severe AD.

In some embodiments, the IL-13 binding agent is administered with a second therapeutic agent, such as an antibacterial agent, an anti-viral agent, an anti-fungal agent, another IL-13 antagonist, an IgE inhibitor, a non-steroid anti-inflammatory drug (NSAID) or interferon γ (IFNγ). The second therapeutic agent may be administered to the subject before, after or concurrently with the IL-13 binding protein.

Treatment of Pruritus

In some aspects, the methods described herein treat pruritus (i.e. itching).

Treatment of pruritus means a reduction of Worst Daily Pruritus Numerical Rating Score (NRS) compared to baseline, e.g. before treatment. In some embodiments, treatment of puritus is characterised by a ≥1-point reduction, a ≥2-point reduction, a ≥3-point reduction, or a ≥4-point reduction in Worst Daily Pruritus NRS from baseline e.g. before treatment.

Worst Daily Pruritus NRS is established according to FDA and EMA recommendations (see, e.g. FDA "*The Food and Drug Administration. Guidance for Industry. Patient-Reported Outcome Measures: Use in Medical Product Development to Support Labeling Claims.* 2009" and EMA "*Reflection paper on the regulatory guidance for the use of health-related quality of life (HRQOL) measures in the evaluation of medicinal products. EMEA/CHMP/EWP/139391/2004.* 2005). For pruritus NRS, a subject assesses their worst itch severity over the past 24 hours using an 11 point NRS ("Worst Daily Pruritus NRS") from 0 (no itch) to 10 (worst itch imaginable).

In some embodiments, the IL-13 binding protein is not administered in combination with a topical corticosteroid. "Not administered in combination with" means "not administered in the same course of treatment". In some embodiments, the IL-13 binding protein is administered as a monotherapy for treating pruritus in a subject having moderate to severe AD.

Treatment of Eczema-Related Sleep Interference

In some aspects, the methods described herein treat eczema-related sleep interference.

For eczema-related sleep interference numerical rating score (NRS), a subject rates how much their eczema interfered with their sleep the previous night using an 11 point NRS from 0 (no interference) to 10 (complete interference).

Treatment of eczema-related sleep interference means a reduction of eczema-related sleep interference NRS compared to baseline e.g. before treatment. In some embodiments, treatment of eczema-related sleep interference NRS is characterised by a ≥0.4-point reduction, a ≥1-point reduction, a ≥2-point reduction, or a ≥4-point reduction in eczema-related sleep interference NRS from baseline, e.g. before treatment.

Treatment of Anxiety and Depression

In some aspects, the methods described herein treat anxiety and/or depression.

To assess anxiety and/or depression using HADS, a patient scores fourteen items on a questionnaire from 0-3, resulting in a total score of 0 to 21 for either anxiety or depression.

Treatment of anxiety and/or depression means a reduction in HADS score compared to baseline e.g. before treatment, for example a reduction in HADS anxiety score and/or HADS depression score. In some embodiments, treatment of anxiety and/or depression is characterised by a ≥1-point reduction, a ≥2-point reduction, a ≥3-point reduction, or a ≥4-point reduction in HADS score from baseline, e.g. before treatment.

In some embodiments, the methods described herein treat anxiety and/or depression in a subject having AD, for example moderate to severe AD. In some preferred embodiments, the subject may have a baseline (e.g. before treatment) HADS score of ≥8, for example a baseline HADS anxiety score and/or HADS depression score of ≥8.

Treatment of Patients Experiencing Conjunctivitis

In some aspects, the invention provides an IL-13 binding protein for use in a method of treating atopic dermatitis in a subject who has experienced conjunctivitis when treated with the IL-13 binding protein in combination with a topical corticosteroid, wherein the method comprises the steps of: (a) administering a first dose of the IL-13 binding protein to said subject, wherein the IL-13 binding protein is not administered to the subject in combination with a topical corticosteroid; and (b) administering one or more secondary dose(s) of the IL-13 binding protein to the subject, wherein each secondary dose is administered to the subject from 12 days to 35 days after the immediately preceding dose and wherein the IL-13 binding protein is not administered to the subject in combination with a topical corticosteroid. Preferably, each secondary dose is administered to the subject from 12 days to 16 days after the immediately preceding dose, e.g. 14 days after the immediately preceding dose, or from 25 days to 31 days after the immediately preceding dose, e.g. about 4 weeks after the immediately preceding dose.

In some aspects, the invention provides an IL-13 binding protein for use in a method of treating atopic dermatitis in a subject, wherein the method comprises the steps of: (a) selecting a subject who has experienced conjunctivitis when treated with the IL-13 binding protein in combination with a topical corticosteroid; (b) administering a first dose of the IL-13 binding protein to said subject, wherein the IL-13 binding protein is not administered to the subject in combination with a topical corticosteroid; and (c) administering one or more secondary dose(s) of the IL-13 binding protein to the subject, wherein each secondary dose is administered to the subject from 12 days to 35 days after the immediately preceding dose and wherein the IL-13 binding protein is not administered to the subject in combination with a topical corticosteroid. Preferably, each secondary dose is administered to the subject from 12 days to 16 days after the immediately preceding dose, e.g. 14 days after the immediately preceding dose, or from 25 days to 31 days after the immediately preceding dose, e.g. about 4 weeks after the immediately preceding dose.

In some aspects, the invention provides a method for treating atopic dermatitis in a subject who has experienced conjunctivitis when treated with the IL-13 binding protein in combination with a topical corticosteroid, wherein the method comprises the steps of: (a) administering a first dose of the IL-13 binding protein to said subject, wherein the IL-13 binding protein is not administered to the subject in combination with a topical corticosteroid; and (b) administering one or more secondary dose(s) of the IL-13 binding protein to the subject, wherein each secondary dose is administered to the subject from 12 days to 35 days after the immediately preceding dose and wherein the IL-13 binding protein is not administered to the subject in combination with a topical corticosteroid. Preferably, each secondary dose is administered to the subject from 12 days to 16 days after the immediately preceding dose, e.g. 14 days after the immediately preceding dose, or from 25 days to 31 days after the immediately preceding dose, e.g. about 4 weeks after the immediately preceding dose.

In some aspects, the invention provides a method for treating atopic dermatitis in a subject, wherein the method comprises the steps of: (a) selecting a subject who has experienced conjunctivitis when treated with the IL-13 binding protein in combination with a topical corticosteroid; (b) administering a first dose of the IL-13 binding protein to said subject, wherein the IL-13 binding protein is not administered to the subject in combination with a topical corticosteroid; and (c) administering one or more secondary dose(s) of the IL-13 binding protein to the subject, wherein each secondary dose is administered to the subject from 12 days to 35 days after the immediately preceding dose and wherein the IL-13 binding protein is not administered to the subject in combination with a topical corticosteroid. Preferably, each secondary dose is administered to the subject from 12 days to 16 days after the immediately preceding dose, e.g. 14 days after the immediately preceding dose, or from 25 days to 31 days after the immediately preceding dose, e.g. about 4 weeks after the immediately preceding dose.

In some aspects, the invention provides the use of an IL-13 binding protein in the manufacture of a medicament for treating atopic dermatitis in a subject who has experienced conjunctivitis when treated with the IL-13 binding protein in combination with a topical corticosteroid, wherein the method comprises the steps of: (a) administering a first dose of the IL-13 binding protein to said subject, wherein the IL-13 binding protein is not administered to the subject in combination with a topical corticosteroid; and (b) administering one or more secondary dose(s) of the IL-13 binding protein to the subject, wherein each secondary dose is administered to the subject from 12 days to 35 days after the immediately preceding dose and wherein the IL-13 binding protein is not administered to the subject in combination with a topical corticosteroid. Preferably, each secondary dose is administered to the subject from 12 days to 16 days after the immediately preceding dose, e.g. 14 days after the immediately preceding dose, or from 25 days to 31 days after the immediately preceding dose, e.g. about 4 weeks after the immediately preceding dose.

In some aspects, the invention provides the use of an IL-13 binding protein in the manufacture of a medicament for treating atopic dermatitis in a subject, wherein the method comprises the steps of: (a) selecting a subject who has experienced conjunctivitis when treated with the IL-13 binding protein in combination with a topical corticosteroid; (b) administering a first dose of the IL-13 binding protein to said subject, wherein the IL-13 binding protein is not administered to the subject in combination with a topical corticosteroid; and (c) administering one or more secondary dose(s) of the IL-13 binding protein to the subject, wherein each secondary dose is administered to the subject from 12 days to 35 days after the immediately preceding dose and wherein the IL-13 binding protein is not administered to the subject in combination with a topical corticosteroid. Preferably, each secondary dose is administered to the subject from 12 days to 16 days after the immediately preceding dose, e.g. 14 days after the immediately preceding dose, or from 25 days to 31 days after the immediately preceding dose, e.g. about 4 weeks after the immediately preceding dose.

In some aspects, the invention provides an IL-13 binding protein for use in a method of treating atopic dermatitis in a subject who has experienced conjunctivitis when treated with an anti-IL4Rα antibody or an antibody that inhibits IL4/IL13 signalling, e.g. dupilumab, wherein the method comprises the steps of: (a) administering a first dose of the IL-13 binding protein to said subject; and (b) administering one or more secondary dose(s) of the IL-13 binding protein to the subject, wherein each secondary dose is administered to the subject from 12 days to 35 days after the immediately preceding dose. Preferably, each secondary dose is administered to the subject from 12 days to 16 days after the immediately preceding dose, e.g. 14 days after the immediately preceding dose, or from 25 days to 31 days after the immediately preceding dose, e.g. about 4 weeks after the immediately preceding dose. Preferably, the IL-13 binding protein is not administered to the subject in combination with a topical corticosteroid.

In some aspects, the invention provides an IL-13 binding protein for use in a method of treating atopic dermatitis in a subject, wherein the method comprises the steps of: (a) selecting a subject who has experienced conjunctivitis when treated with an anti-IL4Rα antibody or an antibody that inhibits IL4/IL13 signalling, e.g. dupilumab; (b) administering a first dose of the IL-13 binding protein to said subject; and (c) administering one or more secondary dose(s) of the IL-13 binding protein to the subject, wherein each secondary dose is administered to the subject from 12 days to 35 days after the immediately preceding dose. Preferably, each secondary dose is administered to the subject from 12 days to 16 days after the immediately preceding dose, e.g. 14 days after the immediately preceding dose, or from 25 days to 31 days after the immediately preceding dose, e.g. about 4 weeks after the immediately preceding dose. Preferably, the IL-13 binding protein is not administered to the subject in combination with a topical corticosteroid.

In some aspects, the invention provides a method for treating atopic dermatitis in a subject who has experienced conjunctivitis when treated with an anti-IL4Rα antibody or an antibody that inhibits IL4/IL13 signalling, e.g. dupilumab, wherein the method comprises the steps of: (a) administering a first dose of the IL-13 binding protein to said subject; and (b) administering one or more secondary dose(s) of the IL-13 binding protein to the subject, wherein each secondary dose is administered to the subject from 12 days to 35 days after the immediately preceding dose. Preferably, each secondary dose is administered to the subject from 12 days to 16 days after the immediately preceding dose, e.g. 14 days after the immediately preceding dose, or from 25 days to 31 days after the immediately preceding dose, e.g. about 4 weeks after the immediately preceding dose. Preferably, the IL-13 binding protein is not administered to the subject in combination with a topical corticosteroid.

In some aspects, the invention provides a method for treating atopic dermatitis in a subject, wherein the method comprises the steps of: (a) selecting a subject who has experienced conjunctivitis when treated with an anti-IL4Rα antibody or an antibody that inhibits IL4/IL13 signalling, e.g. dupilumab; (b) administering a first dose of the IL-13 binding protein to said subject; and (c) administering one or more secondary dose(s) of the IL-13 binding protein to the subject, wherein each secondary dose is administered to the subject from 12 days to 35 days after the immediately preceding dose. Preferably, each secondary dose is administered to the subject from 12 days to 16 days after the immediately preceding dose, e.g. 14 days after the immediately preceding dose, or from 25 days to 31 days after the immediately preceding dose, e.g. about 4 weeks after the immediately preceding dose. Preferably, the IL-13 binding protein is not administered to the subject in combination with a topical corticosteroid.

In some aspects, the invention provides the use of an IL-13 binding protein in the manufacture of a medicament for treating atopic dermatitis in a subject who has experienced conjunctivitis when treated with an anti-IL4Rα antibody or an antibody that inhibits IL4/IL13 signalling, e.g. dupilumab, wherein the method comprises the steps of: (a) administering a first dose of the IL-13 binding protein to said subject; and (b) administering one or more secondary dose(s) of the IL-13 binding protein to the subject, wherein each secondary dose is administered to the subject from 12 days to 35 days after the immediately preceding dose. Preferably, each secondary dose is administered to the subject from 12 days to 16 days after the immediately preceding dose, e.g. 14 days after the immediately preceding dose, or from 25 days to 31 days after the immediately preceding dose, e.g. about 4 weeks after the immediately preceding dose. Preferably, the IL-13 binding protein is not administered to the subject in combination with a topical corticosteroid.

In some aspects, the invention provides the use of an IL-13 binding protein in the manufacture of a medicament for treating atopic dermatitis in a subject, wherein the method comprises the steps of: (a) selecting a subject who has experienced conjunctivitis when treated with an anti-IL4Rα antibody or an antibody that inhibits IL4/IL13 signalling, e.g. dupilumab; (b) administering a first dose of the IL-13 binding protein to said subject; and (c) administering one or more secondary dose(s) of the IL-13 binding protein to the subject, wherein each secondary dose is administered to the subject from 12 days to 35 days after the immediately preceding dose. Preferably, each secondary dose is administered to the subject from 12 days to 16 days after the immediately preceding dose, e.g. 14 days after the immediately preceding dose, or from 25 days to 31 days after the immediately preceding dose, e.g. about 4 weeks after the immediately preceding dose. Preferably, the IL-13 binding protein is not administered to the subject in combination with a topical corticosteroid.

In some embodiments of the above aspects for treatment of AD patients experiencing conjunctivitis following treatment with an alternative therapy, the method comprises the steps of:
(i) administering one or more prior dose(s) of the IL-13 binding protein to the subject for around 8 weeks to 16 weeks, wherein each prior dose is administered from 12 days to 16 days after the immediately preceding dose;
(ii) administering a first dose of the IL-13 binding protein to the subject; and
(iii) administering one or more secondary dose(s) of the IL-13 binding protein to the subject for at least 12 weeks, wherein each secondary dose of the IL-13 binding protein is administered to the subject from 12 to 16 days or from 26 days to 30 days after the immediately preceding dose, wherein the first dose of said one or more prior doses is around 600 mg of IL-13 binding protein and each dose (prior dose(s), first dose, and secondary dose(s)) administered after the first of said one or more prior doses is around 300 mg of IL-13 binding protein.

In some embodiments of the above aspects for treatment of AD patients experiencing conjunctivitis following treatment with an alternative therapy, the method comprises the steps of:
(i) administering one or more prior dose(s) of the IL-13 binding protein to the subject for around 12 weeks to 16 weeks, wherein each prior dose is administered about 2 weeks after the immediately preceding dose;
(ii) administering a first dose of the IL-13 binding protein to the subject; and
(iii) administering one or more secondary dose(s) of the IL-13 binding protein to the subject for at least 16 weeks, wherein each secondary dose of the IL-13 binding protein is administered to the subject around 2 weeks or around 4 weeks after the immediately preceding dose, wherein the first dose of said one or more prior doses is around 600 mg of IL-13 binding protein and each dose (prior dose(s), first dose, and secondary dose(s)) administered after the first of said one or more prior doses is around 300 mg of IL-13 binding protein.

Subject

As used herein, the term "subject" includes human and non-human animals, particularly mammals. Typically, the subject is a human, as shown in the examples below.

A subject with AD (especially moderate-to-severe AD or severe AD) may be resistant, non-responsive or inadequately responsive to treatment with a non-steroid systemic immunosuppressant. The term "non-steroid systemic immunosuppressant" includes cyclosporine A, methotrexate, mycophenolate mofetil, azathioprine, and interferon-gamma. In certain embodiments, the term also includes immunobiologics such as tumor necrosis factor alpha (TNFa) inhibitors (e.g. an anti-TNFa antibody such as infliximab), CD11a inhibitors (e.g. an anti-CD11a antibody such as efalizumab), IgE inhibitors (e.g. omalizumab), CD20 inhibitors (e.g. rituximab). Thus, in some cases, the methods described herein may treat AD in subjects that are resistant, nonresponsive (refractory) or inadequately responsive to treatment with a systemic immunosuppressant. The term "resistant, non-responsive or inadequately responsive to a systemic immunosuppressant" refers to a subject with AD that has been treated with a systemic immunosuppressant and the immunosuppressant did not have a therapeutic effect, e.g. a subject with moderate-to-severe AD or severe AD (such as those with chronic relapsing AD) that has been treated with a non-steroid systemic immunosuppressant for between 1-3 months and did not show a decrease in one or more AD-associated parameter score(s). The time for the assessment of a therapeutic effect will vary depending on the typical timeframe for onset of action of the non-steroid systemic immunosuppressant. Such timeframes are well known. For example, for cyclosporine the onset of action is typically 2-6 weeks, but for other non-steroid systemic immunosuppressants it is typically around 8-12 weeks.

In some embodiments, immunosuppressant treatment has been deemed not medically advisable by a physician for the subject. Such a subject may be identified by the following criteria: (1) no prior immunosuppressant exposure; (2) not currently a candidate for immunosuppressant treatment due to: medical contraindication(s); or hypersensitivity to the immunosuppressant or excipient(s); use of concomitant medications prohibited with immunosuppressant; or increased susceptibility to immunosuppressant induced renal damage or increased risk of serious infections; (3) previous intolerance and/or unacceptable toxicity on previous exposure to an immunosuppressant; and/or (4) requirement for immunosuppressant at doses or duration beyond that specified in the prescribing information.

IL-13 Binding Protein

An IL-13 binding protein is a protein that specifically binds to and neutralizes human IL-13.

Herein, the term "specifically binds" means that a protein (such as an antibody or antigen-binding fragment thereof) forms a complex with an antigen that is relatively stable under physiological conditions. Methods for determining whether a protein specifically binds to an antigen are well known in the art and include, for example, equilibrium dialysis, surface plasmon resonance (e.g. using a BIAcore 200 Biosensor (BIAcore AB), and the like. For example, an IL-13 binding protein (e.g. an anti-IL-13 antibody or IL-13 binding fragment thereof) that "specifically binds" IL-13 may bind IL-13 with a $K_D$ of less than about 1000 nM, less than about 500 nM, less than about 100 nM, less than about 50 nM, less than about 20 nM, less than about 10 nM, less than about 5 nM, less than about 1 nM, less than about 0.5 nM, less than about 0.25 nM, less than about 0.1 nM or less than about 0.05 nM, as measured by surface plasmon resonance at 25° C. The exemplified antibody, tralokinumab binds human bound human IL-13 with a $K_D$ of 178 pM, as measured by surface plasmon resonance (see WO 2005/007699 for detailed methods). Accordingly, in a preferred embodiment, the anti-IL-13 antibody has a $K_D$ of less than about 200 pM, as measured by surface plasmon resonance at 37° C. or 25° C. Although an IL-13 binding protein specifically binds human IL-13, it may have cross-reactivity to other antigens, such as IL-13 from other (non-human) species.

Methods for measuring neutralisation activity are well known in the art. Neutralisation activity can be measured in an IL-13 dependent TF-1 cell proliferation assay relative to a control antibody that is not directed to IL-13, as described in WO 2005/007699. In this assay, inhibition of IL-13 dependent proliferation is determined by measuring the reduction in incorporation of tritiated thymidine into the newly synthesized DNA of dividing cells. Briefly, commercial TF-1 cells are maintained according to supplied protocols. Assay media comprises RPMI-1640 with GLUTA-MAX I (Invitrogen) containing 5% FBS and 1% sodium pyruvate. Prior to each assay, TF-1 cells are pelleted by centrifugation at 300×g for 5 minutes, the media removed by aspiration and the cells resuspended in assay media. This process is repeated twice with cells resuspended at a final concentration of $10^5$ cells/mL in assay media. Test solutions of antibody (in triplicate) are diluted to the desired concentration in assay media. An antibody that is not directed at IL-13 is used as a negative control. Recombinant bacterially derived human or murine IL-13 is added to a final concentration of 50 ng/mL when mixed with the appropriate test antibody in a total volume of 100 µL/well in a 96 well assay plate. The concentration of IL-13 used in the assay is selected as the dose that at final assay concentration gives approximately 80% of the maximal proliferative response. All samples are incubated for 30 minutes at room temperature. 100 µL of resuspended cells are then added to each assay point to give a total assay volume of 200 µL/well. Assay plates are incubated for 72 hours at 37° C. under 5% $CO_2$. 25 µL of tritiated thymidine (10 µCi/mL) is then added to each assay point and assay plates are returned to the incubator for a further 4 hours. Cells are harvested on glass fibre filter plates (Perkin Elmer) using a cell harvester. Thymidine incorporation is determined using a Packard TopCount microplate liquid scintillation counter.

Anti-IL-13 Antibodies and IL-13-Binding Thereof

Typically, the IL-13 binding protein is an anti-IL-13 antibody or an IL-13-binding fragment thereof.

The term "antibody", as used herein, includes immunoglobulin molecules comprising four polypeptide chains, two heavy (H) chains and two light (L) chains inter-connected by disulfide bonds, as well as multimers thereof (e.g. IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In some cases, the FRs of the anti-IL-13 antibody (or IL-13-binding fragment or derivative thereof) may be identical to the human germline sequences, or may be naturally or artificially modified.

The heavy chain constant region of the antibodies may be from any types of constant region, such as IgG, IgM, IgD, IgA, and IgE. Generally, the antibody is an IgG (e.g. isotype IgG1, IgG2, IgG3 or IgG4). Preferably, the antibody is an IgG4, as exemplified herein.

The antibody may be a mouse, human, primate, humanized or chimeric antibody. The antibody may be polyclonal or monoclonal. For therapeutic applications, monoclonal and human (or humanized) antibodies are preferred. In a particularly preferred embodiment, the antibody is human or humanized, and monoclonal.

The antibody can be a multispecific (e.g. bispecific) antibody. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen binding fragment of an antibody as described herein using routine techniques available in the art. For example, the methods that use of bispecific antibodies, wherein one arm of an immunoglobulin is specific for IL-13, and the other arm of the immunoglobulin is specific for a second therapeutic target or is conjugated to a therapeutic moiety.

An IL-13-binding fragment of an anti-IL-13 antibody may be any naturally occurring, enzymatically obtainable, synthetic, or genetically engineered polypeptide. Such fragments may be derived, e.g. from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g. commercial sources, DNA libraries (including, e.g. phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of IL-13-binding fragments include: Fab, Fab', F(ab')2, Fd, Fv, single-chain Fv (scFv), disulphide-linked Fvs, dAb fragments, and other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immuno-pharmaceuticals (SMIPs), and shark variable IgNAR domains.

An IL-13-binding fragment of an anti-IL-13-binding antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

The anti-IL-13 antibody, or an IL-13-binding fragment thereof, may comprise: a heavy chain complementarity determining region 1 (HCDR1) comprising an amino acid sequence of SEQ ID NO:1; a heavy chain complementarity determining region 2 (HCDR2) comprising an amino acid sequence of SEQ ID NO:2; a heavy chain complementarity determining region 3 (HCDR3) comprising an amino acid sequence of SEQ ID NO:3; a light chain complementarity determining region 1 (LCDR1) comprising an amino acid sequence of SEQ ID NO:4; a light chain complementarity determining region 2 (LCDR2) comprising an amino acid sequence of SEQ ID NO:5; and a light chain complementarity determining region 3 (LCDR3) comprising an amino acid sequence of SEQ ID NO:6. The anti-IL-13 antibody, or an IL-13-binding fragment thereof, may comprise a heavy chain variable region (HCVR) and a light chain variable region (LCVR), wherein: (i) the heavy chain variable region comprises: a heavy chain complementarity determining region 1 (HCDR1) comprising an amino acid sequence of SEQ ID NO:1; a heavy chain complementarity determining region 2 (HCDR2) comprising an amino acid sequence of SEQ ID NO:2; and a heavy chain complementarity determining region 3 (HCDR3) comprising an amino acid sequence of SEQ ID NO:3; and (ii) the light chain variable region comprises: a light chain complementarity determining region 1 (LCDR1) comprising an amino acid sequence of SEQ ID NO:4; a light chain complementarity determining region 2 (LCDR2) comprising an amino acid sequence of SEQ ID NO:5; and a light chain complementarity determining region 3 (LCDR3) comprising an amino acid sequence of SEQ ID NO:6. In addition, the anti-IL-13 antibody, or an IL-13-binding fragment thereof, may further comprise: (i) an amino acid sequence that is at least 80%, at least 85%, at least 90%, at least 95%, at least 96%, at least 97%, at least 98%, or at least 99% identical to a heavy chain variable region sequence of SEQ ID NO: 8; and/or (ii) an amino acid sequence that is 80%, at least 85%, at least 90%, at least 95%, at least 96%, at least 97%, at least 98%, or at least 99% identical to a light chain variable region sequence of SEQ ID NO: 10. The anti-IL-13 antibody, or an IL-13-binding fragment thereof, may comprise a heavy chain variable region sequence of SEQ ID NO: 8 and a light chain variable region sequence of SEQ ID NO: 10.

The anti-IL-13 antibody, or the IL-13-binding fragment thereof, may comprise: (i) an amino acid sequence that is at least 80%, at least 85%, at least 90%, at least 95%, at least 96%, at least 97%, at least 98%, or at least 99% identical to the heavy chain sequence of SEQ ID NO: 11; and/or (ii) an amino acid sequence that is at least 80%, at least 85%, at least 90%, at least 95%, at least 96%, at least 97%, at least 98%, or at least 99% identical to the light chain sequence of SEQ ID NO: 12. In some cases, the anti-IL-13 antibody, or an IL-13-binding fragment or IL-13-binding derivative thereof, comprises a heavy chain of SEQ ID NO: 11 and a light chain sequence of SEQ ID NO: 12.

One such antibody that can be used in the methods described herein is the anti-IL-13 antibody, tralokinumab (as described in the *"International Nonproprietary Names for Pharmaceutical Substances (INN)"* list 102 (*WHO Drug Information* (2009) 23 (4): pp 348)). Tralokinumab is a fully human IgG4-lambda antibody, which specifically binds and neutralises human IL-13.

TABLE 1

| SEQ ID number | Name | Sequence |
|---|---|---|
| | | Tralokinumab |
| SEQ ID NO: 1 | HCDR1 | NYGLS |
| SEQ ID NO: 2 | HCDR2 | WISANNGDTNYGQEFQG |
| SEQ ID NO: 3 | HCDR3 | DSSSSWARWFFDL |
| SEQ ID NO: 4 | LCDR1 | GGNIIGSKLVH |
| SEQ ID NO: 5 | LCDR2 | DDGDRPS |
| SEQ ID NO: 6 | LCDR3 | QVWDTGSDPVV |
| SEQ ID NO: 7 | cDNA heavy chain variable domain | caggtccagctggtgcagtctggggctgaggtgaagaagcctgggg cctcagtgaaggtctcctgcaaggcttctggttacacctttacaaattat ggtctcagctgggtgcgacaggcccctggacaagggcttgagtggat gggatggatcagcgctaataatggcgacacaaattatggacaggaatt ccagggcagagtcaccatgaccacagatacatccacgagcacagcc tacatggagttgaggagcctgagatctgacgacacggccgtttattact gtgcgagagactccagcagcagctgggcccgctggttttttcgatctct gggccgggggacactggtcaccgtctcctca |
| SEQ ID NO: 8 | polypeptide sequence heavy chain variable region | QVQLVQSGAEVKKPGASVKVSCKASGYTFT NYGLSWVRQAPGQGLEWMGWISANNGDTN YGQEFQGRVTMTTDTSTSTAYMELRSLRSD DTAVYYCARDSSSSWARWFFDLWGRGTLV TVSS |
| SEQ ID NO: 9 | cDNA light chain variable domain | tcctatgtgctgactcagccaccctcggtgtcagtggccccaggaaag acggccaggattacctgtgggggaaacatcattggaagtaaacttgta cactggtaccagcagaagccaggccaggcccctgtgctggtcatcta tgatgatggcgaccggccctcagggatccctgagcgattctctggctc caactctgggaacacggccaccctgaccatcagcagggtcgaggcc ggggatgaggccgactattattgtcaggtgtgggatactggtagtgat cccgtggtattcggcggagggaccaagctgaccgtcctaggt |
| SEQ ID NO: 10 | polypeptide sequence light chain variable region | SYVLTQPPSVSVAPGKTARITCGGNIIGSKLV HWYQQKPGQAPVLVIYDDGDRPSGIPERFSG SNSGNTATLTISRVEAGDEADYYCQVWDTG SDPVVFGGGTKLTVL |
| SEQ ID NO: 11 | Heavy chain | QVQLVQSGAEVKKPGASVKVSCKASGYTFT NYGLSWVRQAPGQGLEWMGWISANNGDTN YGQEFQGRVTMTTDTSTSTAYMELRSLRSD DTAVYYCARDSSSSWARWFFDLWGRGTLV TVSSASTKGPSVFPLAPCSRSTSESTAALGCL VKDYFPEPVTVSWNSGALTSGVHTFPAVLQS SGLYSLSSVVTVPSSSLGTKTYTCNVDHKPS NTKVDKRVESKYGPPCPSCPAPEFLGGPSVF LFPPKPKDTLMISRTPEVTCVVVDVSQEDPE VQFNWYVDGVEVHNAKTKPREEQFNSTYR VVSVLTVLHQDWLNGKEYKCKVSNKGLPSS IEKTISKAKGQPREPQVYTLPPSQEEMTKNQ VSLTCLVKGFYPSDIAVEWESNGQPENNYKT TPPVLDSDGSFFLYSRLTVDKSRWQEGNVFS CSVMHEALHNHYTQKSLSLSLGK |
| SEQ ID NO: 12 | Light chain | SYVLTQPPSVSVAPGKTARITCGGNIIGSKLV HWYQQKPGQAPVLVIYDDGDRPSGIPERFSG SNSGNTATLTISRVEAGDEADYYCQVWDTG SDPVVFGGGTKLTVLGQPKAAPSVTLFPPSS EELQANKATLVCLISDFYPGAVTVAWKADS SPVKAGVETTTPSKQSNNKYAASSYLSLTPE QWKSHRSYSCQVTHEGSTVEKTVAPTECS |

Methods for identifying, isolating and testing (e.g. binding and neutralisation) of antibodies and fragment thereof are well-known in the art. See WO 2005/007699, which teaches the identification and characterisation of various anti-IL13 antibodies and fragments and provides suitable methods for doing so.

Dose and Dosing Regimen

The invention provides an interleukin-13 (IL-13) binding protein as described above (e.g. an anti-IL-13 antibody or IL-13 binding fragment thereof) for use in any method of treatment described herein, wherein the method comprises the steps of: (a) administering a first dose of the IL-13 binding protein to the subject; and (b) administering one or more secondary dose(s) of the IL-13 binding protein to the subject, wherein each secondary dose is administered to the subject from 12 days to 35 days after the immediately preceding dose. Preferably, each secondary dose is administered to the subject from 12 days to 16 days after the immediately preceding dose, e.g. 14 days after the immediately preceding dose, or from 25 days to 31 days after the immediately preceding dose, e.g. about 4 weeks after the immediately preceding dose.

The term "dose" refers to the amount (mass) of IL-13 binding protein administered to the subject on the particular treatment day. For example, a dose of 300 mg of IL-13 binding protein means that on a treatment day a total of 300 mg of IL-13 binding protein is given to the subject. Typically, a dose is administered in a single administration step (e.g. one injection). However, in some embodiments, one, two, three or more administration steps (e.g. one, two, three or more injections) may be used to provide the subject with the desired dose.

The terms "prior dose", "first dose", "secondary dose", and "tertiary dose" refer to the temporal sequence of administration of the IL-13 binding protein. The term "first dose" is a single dose of IL-13 binding protein that is followed by one or more secondary dose(s). The first dose may be preceded by one or more prior dose(s), or the "first dose" may be the initiation of treatment by the method described herein (in the latter case, this dose can therefore be referred to as the "baseline dose"). Subsequent to the first dose is one or more secondary dose(s); and the one or more secondary dose(s) may be followed by one or more tertiary dose(s).

The phrase "immediately preceding dose" means, in a sequence of multiple doses, the dose of IL-13 binding protein which is administered to a patient prior to the administration of the very next dose in the sequence, with no intervening doses of the IL-13 binding protein.

"Dosing frequency" is the frequency of administering a dose of the IL-13 binding protein. Thus, a decrease in dosing frequency means an increase in the time interval between doses. Common terminology used in relation to dosing frequency is QW (once weekly), Q2W (once every 2 weeks), Q3W (every 3 weeks), or Q4W (every 4 weeks).

The first dose may be from about 10 mg to about 600 mg of the IL-13 binding protein, from about 50 mg to 500 mg, from about 100 mg to about 400 mg, from about 250 mg to about 350 mg or from about 280 mg to about 320 mg of IL-13 binding protein. For example, the first dose is about 10 mg, about 25 mg, about 50 mg, about 100 mg, about 150 mg, about 200 mg, about 250 mg, about 300 mg, about 400 mg or about 500 mg. In some cases, the first dose is 600 mg or less, 500 mg or less, 400 mg or less, 300 mg or less, 200 mg or less, or 200 mg or less. In preferred embodiments, the first dose is about 300 mg of IL-13 binding protein (e.g. as illustrated in the examples).

Each secondary dose may be administered to the subject from 18 days to 35 days, from 21 days to 35 days, from 22 days to 34 days, from 24 days to 32 days, from 25 days to 31 days, from 26 days to 30 days, or from 27 days to 29 days after the immediately preceding dose. In certain cases, each secondary dose may be administered to the subject about 28 days after the immediately preceding dose (as exemplified herein).

In the methods described herein, the method may be carried out until it provides improvement in an AD-associated parameter and/or patient-related outcome as described herein. In some cases, the method may provide an improvement in an AD-associated parameter and/or patient-related outcome in around 2 weeks, around 3 weeks, around 12 weeks, around 3 months, around 16 weeks, around 24 weeks, around 6 months, around 32 weeks, around 36 weeks, around a year, or around 52 weeks. In preferred embodiments, the improvement in an AD-associated parameter and/or patient-related outcome is provided in around 16 weeks (e.g. an improvement in IGA and EASI scores, as in Example 1 and Example 4).

In some cases, the method may be continued until the subject reaches a low disease state. For example, the subject may reach a low disease state in around 4 weeks, around 8 weeks, around 12 weeks, around 3 months, around 16 weeks, around 24 weeks, around 6 months, around 32 weeks, around 36 weeks, around a year, or around 52 weeks. In preferred embodiments, the subject may reach a low disease state in around 16 weeks (as in Example 1 and Example 4).

In some cases, the method may be carried out for at least 4 weeks, at least 8 weeks, at least 12 weeks, at least 3 months, at least 16 weeks, at least 24 weeks, at least 6 months, at least 32 weeks, at least 36 weeks, at least a year, or at least 52 weeks or more. In some cases, the method may be carried out for around 2 weeks, around 3 weeks, around 12 weeks, around 3 months, around 16 weeks, around 24 weeks, around 6 months, around 32 weeks, around 36 weeks, around a year, around 52 weeks. In preferred embodiments, the method is carried out for at least 16 weeks (e.g. as in Example 1 and Example 4), at least 32 weeks (e.g. as in Example 1) or at least 52 weeks (e.g. as in Example 4).

Herein, the phrase "low disease state" is an Investigator's Global Assessment (IGA) score of 0 or 1 and/or ≥75% improvement of Eczema Area and Severity Index (EASI-75) over baseline.

Step (b) of the method (i.e. administering one or more secondary dose(s) of the IL-13 binding protein to the subject) may be continued (i.e. by administering more than one secondary dose) for from 8 weeks to 52 weeks, from 12 to 40 weeks or from 16 to 36 weeks. The one or more secondary dose(s) may be administered for at least 8 weeks, at least 12 weeks, at least 3 months, at least 16 weeks, at least 20 weeks, at least 24 weeks, at least 6 months, at least 28 weeks, at least 32 weeks, at least 36 weeks, at least a year, at least 52 weeks or more. Step (b) of the method may be continued (i.e. by administering more than one secondary dose) for around 8 weeks, around 12 weeks, around 3 months, around 16 weeks, around 20 weeks, around 24 weeks, around 6 months, around 28 weeks, around 32 weeks, around 36 weeks, around a year, around 52 weeks or more. In preferred embodiments, the one or more secondary dose(s) is administered for at least 16 weeks (e.g. as in Example 1) or at least 36 weeks (e.g. as in Example 4). Additionally, or alternatively, step (b) may be continued until the method provides improvement in an AD-associated parameter and/or patient-related outcome as described herein. Step (b) of may be continued to maintain improvement in an AD-associated parameter and/or patient-related outcome as described herein. In particular cases, step (b) may be continued until the subject reaches a low disease state.

Each secondary dose may be from about 10 mg to about 600 mg of the IL-13 binding protein, from about 50 mg to 500 mg, from about 100 mg to about 400 mg, from about 250 mg to about 350 mg or from about 280 mg to about 320 mg of IL-13 binding protein. For example, each secondary dose is about 10 mg, about 25 mg, about 50 mg, about 100 mg, about 150 mg, about 200 mg, about 250 mg, about 300 mg, about 400 mg or about 500 mg. In some cases, each secondary dose is 600 mg or less, 500 mg or less, 400 mg or less, 300 mg or less, 200 mg or less or 200 mg or less. In preferred embodiments, each secondary dose is about 300 mg of IL-13 binding protein (e.g. as in the examples). Typically, the first dose and one or more secondary dose(s) are the same amount (i.e. in milligrams) of IL-13 binding protein.

In preferred embodiments, the method comprises the steps of: (a) administering a first dose of about 300 mg of the IL 13 binding protein (e.g. tralokinumab) to the subject; and (b) administering one or more secondary dose(s) of about 300 mg of the IL-13 binding protein (e.g. tralokinumab) to the subject, wherein each secondary dose is administered to the subject about 4 weeks after the immediately preceding dose, optionally wherein the method is carried out for about 12 weeks (i.e. where about 300 mg of the IL-13 binding protein (e.g. tralokinumab) is administered to the subject at week 0, week 4, week 8 and week 12). Preferably, each administration is by subcutaneous injection.

In the methods described herein, prior to step (a) (i.e. administering a first dose of the IL-13 binding protein to the subject) the method may further comprise a step of administering one or more prior dose(s) of the IL-13 binding protein to the subject. Each prior dose can be administered to the subject from 3 days to 6 weeks after the immediately preceding prior dose, e.g. from 1 week to 6 weeks, from 1 week to 4 weeks, from 1 week to 3 weeks or from 1 week to 2 weeks. In preferred embodiments, each prior dose is administered to the subject from 12 days to 16 days (e.g. about 2 weeks) after the immediately preceding prior dose (as illustrated in the examples).

The method may comprise administering one or more prior dose(s) of the IL-13 binding protein to the subject for from 2 weeks to 36 weeks, from 4 weeks to 20 weeks from 8 weeks to 16 weeks, or from 12 weeks to 16 weeks, e.g. about 2 weeks, about 4 weeks, about 6 weeks, about 8 weeks, about 12 weeks, about 16 weeks, about 20 weeks or more. Preferably, the method comprises administering one or more prior dose(s) of the IL-13 binding protein to the subject for around 16 weeks or less (e.g. as in Examples 1 and 4). Additionally, or alternatively, administering one or more prior dose(s) of the IL-13 binding protein may be continued (by administering more than one prior dose), until the method provides improvement in an AD-associated parameter and/or patient-related outcome as described herein. In certain cases, administering one or more prior dose(s) of the IL-13 binding protein may be continued until the subject reaches a low disease state. For example, if the subject demonstrates a partial improvement in an AD-associated parameter and/or patient-related outcome as described herein following administration of the one or more prior dose(s) of the IL-13 binding protein to the subject for around 16 weeks, then administering one or more prior dose(s) of the IL-13 binding protein to the subject may be continued for more than 16 weeks, e.g. for about 20 weeks or more, for about 24 weeks or more, for about 28 weeks or more, for about 32 weeks or more, for about 36 weeks or more, for about 40 weeks or more, for about 44 weeks or more, for about 48 weeks or more, or for about 52 weeks or more, until the method provides the required improvement in an AD-associated parameter and/or patient-related outcome as described herein. In preferred embodiments, each prior dose is administered to the subject from 12 days to 16 days (e.g. about 2 weeks) after the immediately preceding prior dose. Preferably, administering the one or more prior dose(s) from 12 days to 16 days (e.g. about 2 weeks) after the immediately preceding prior dose is continued until the subject achieves an Investigator's Global Assessment (IGA) score of 0 or 1 and/or ≥75% improvement of Eczema Area and Severity Index (EASI-75) over baseline in the subject. Once the subject has achieved the desired response, one or more secondary dose(s) of the IL-13 binding protein can be administered to the subject from 15 days to 35 days after the immediately preceding dose, preferably 28 days after the immediately preceding dose.

Each prior dose may be from about 10 mg to about 600 mg of the IL-13 binding protein, from about 50 mg to 500 mg, from 100 mg to about 400 mg, from about 250 mg to about 350 mg or from about 280 mg to about 320 mg of IL-13 binding protein. For example, each prior dose is about 10 mg, about 25 mg, about 50 mg, about 100 mg, about 150 mg, about 200 mg, about 250 mg, about 300 mg, about 400 mg or about 500 mg. In some cases, the dose is 600 mg or less, 500 mg or less, 400 mg or less, 300 mg or less, 200 mg or less or 200 mg or less. In preferred embodiments, each prior dose is about 300 mg of IL-13 binding protein (e.g. as illustrated in the examples).

When administering one or more prior dose(s) leads to improvement in one or more AD-associated parameter or patient-related outcome as described herein, steps (a) and (b) of the method (i.e. administering a first dose and one or more secondary dose(s) of the IL-13 binding protein to the subject) may further improve, or maintain, the one or more AD-associated parameter or patient-related outcome. When the subject reaches a low disease state by administering one or more prior dose(s), steps (a) and (b) of the method (i.e. administering a first dose and one or more secondary dose(s) of the IL-13 binding protein to the subject) may maintain the low disease state. Preferably, administering one or more prior dose(s) may achieve an Investigator's Global Assessment (IGA) score of 0 or 1 and/or ≥75% improvement of Eczema Area and Severity Index (EASI-75) over baseline in a subject, which is then maintained by method steps (a) and (b) (e.g. as illustrated in Examples 1 and 4).

Where the method comprises one or more prior dose(s) of the IL-13 binding protein, the first of the one or more prior dose(s) is the initial dose in the temporal sequence of administration of the IL-13 binding protein and marks the initiation of treatment by the method described herein. The "first" prior dose in these cases can therefore also be referred to as the "baseline dose".

For example, the methods described herein may comprise the steps of: (i) administering one or more prior dose(s) of the IL-13 binding protein to the subject from 2 weeks to 36 weeks, wherein each prior dose is administered from 3 days to 2 weeks after the immediately preceding dose; (ii) administering a first dose of the IL-13 binding protein to the subject; and (iii) administering one or more secondary dose(s) of the IL-13 binding protein to the subject for at least 8 weeks, wherein each secondary dose of the IL-13 binding protein is administered to the subject from 12 days to 35 days after the immediately preceding dose, wherein each dose (prior dose(s), first dose, and secondary dose(s)) is from about 10 mg to about 600 mg of IL-13 binding protein.

The methods described herein may also comprise the steps of: (i) administering one or more prior dose(s) of the IL-13 binding protein to the subject for around 8 to 16 weeks, wherein each prior dose is administered from 12 days to 16 days after the immediately preceding dose; (ii) administering a first dose of the IL-13 binding protein to the subject; and (iii) administering one or more secondary dose(s) of the IL-13 binding protein to the subject for at least 12 weeks, wherein each secondary dose of the IL-13 binding protein is administered to the subject from 12 to 16 days (e.g. 14 days) or from 26 to 30 days (e.g. 28 days) after the immediately preceding dose, wherein each dose (prior dose(s), first dose, and secondary dose(s)) is from 250 mg to 350 mg of IL-13 binding protein.

The methods described herein may also comprise the steps of: (i) administering one or more prior dose(s) of the IL-13 binding protein to the subject for around 8 to 16 weeks, wherein each prior dose is administered from 12 days to 16 days after the immediately preceding dose; (ii) administering a first dose of the IL-13 binding protein to the subject; and (iii) administering one or more secondary dose(s) of the IL-13 binding protein to the subject for at least 8 weeks, wherein the first dose of said one or more prior doses is around 600 mg of IL-13 binding protein and each dose (prior dose(s), first dose, and secondary dose(s)) administered after the first of said one or more prior doses is around 300 mg of IL-13 binding protein.

The methods described herein may also comprise the steps of: (i) administering one or more prior dose(s) of the IL-13 binding protein to the subject for around 12 weeks to 16 weeks, wherein each prior dose is administered about 2 weeks after the immediately preceding dose; (ii) administering a first dose of the IL-13 binding protein to the subject; and (iii) administering one or more secondary dose(s) of the IL-13 binding protein to the subject for at least 16 weeks, wherein each secondary dose of the IL-13 binding protein is administered to the subject around 2 weeks or around 4 weeks after the immediately preceding dose, wherein each dose (prior dose(s), first dose, and secondary dose(s)) is around 300 mg of IL-13 binding protein.

The methods described herein may also comprise the steps of: (i) administering one or more prior dose(s) of the IL-13 binding protein to the subject for around 12 weeks to 16 weeks, wherein each prior dose is administered about 2 weeks after the immediately preceding dose; (ii) administering a first dose of the IL-13 binding protein to the subject; and (iii) administering one or more secondary dose(s) of the IL-13 binding protein to the subject for at least 16 weeks, wherein each secondary dose of the IL-13 binding protein is administered to the subject around 2 weeks or around 4 weeks after the immediately preceding dose, wherein the first dose of said one or more prior doses is around 600 mg of IL-13 binding protein and each dose (prior dose(s), first dose, and secondary dose(s)) administered after the first of said one or more prior doses is around 300 mg of IL-13 binding protein.

In the uses and method described herein, following step (b) (i.e. administering one or more secondary dose(s) of the IL-13 binding protein to the subject) the method may further comprise a step of: (c) administering one or more tertiary dose(s) of the IL-13 binding protein to the subject.

Each tertiary dose can be administered to the subject from 3 days to 6 weeks after the immediately preceding tertiary dose, e.g. from 1 week to 6 weeks, from 1 week to 4 weeks, from 1 week to 3 weeks or from 1 week to 2 weeks. In preferred embodiments, each tertiary dose is administered to the subject from 12 days to 16 days (e.g. about 2 weeks) after the immediately preceding tertiary dose.

The method may comprise administering one or more tertiary dose(s) of the IL-13 binding protein to the subject for from 2 weeks to 36 weeks, from 4 weeks to 20 weeks from 8 weeks to 16 weeks, or from about 12 weeks to 16 weeks, e.g. about 2 weeks, about 4 weeks, about 6 weeks, about 8 weeks, about 12 weeks, about 16 weeks, or about 20 weeks or more. Additionally, or alternatively, administering one or more tertiary dose(s) of the IL-13 binding protein may be continued (by administering more than one tertiary dose) until the method provides improvement in an AD-associated parameter and/or patient-related outcome as described herein. In certain cases, administering one or more tertiary dose(s) of the IL-13 binding protein may be continued until the subject reaches a low disease state.

Each tertiary dose may be from about 10 mg to about 600 mg of the IL-13 binding protein, from about 50 mg to 500 mg, from about 100 mg to about 400 mg, from about 250 mg to about 350 mg or from about 280 mg to about 320 mg of IL-13 binding protein. For example, each tertiary dose is about 10 mg, about 25 mg, about 50 mg, about 100 mg, about 150 mg, about 200 mg, about 250 mg, about 300 mg, about 400 mg or about 500 mg. In some cases, the dose is 600 mg or less, 500 mg or less, 400 mg or less, 300 mg or less, 200 mg or less or 200 mg or less. In preferred embodiments, each tertiary dose is about 300 mg of IL-13 binding protein.

When method steps (a) and (b) (and optionally any prior doses) lead to improvement in one or more AD-associated parameter or patient-related outcome as described herein, step (c) (i.e. administering one or more tertiary dose(s) of the IL-13 binding protein to the subject) may further improve, or maintain, the one or more AD-associated parameter or patient-related outcome. When the subject reaches a low disease state by administering a first dose and one or more secondary dose(s) of the IL-13 binding protein to the subject (and optionally any prior doses), step (c) (i.e. administering one or more tertiary dose(s) of the IL-13 binding protein to the subject) may maintain a low disease state. For example, a first dose and one or more secondary dose(s) (and optionally any prior doses) may achieve an Investigator's Global Assessment (IGA) score of 0 or 1 and/or ≥75% improvement of Eczema Area and Severity Index (EASI-75) over baseline in a subject, which is then maintained by method step (c).

In the methods described herein, following step (c) the method may further comprise one or more repeat of steps (a), (b) and (c), e.g. the sequence of administration steps may continue repeating—step (a), step (b), step (c), step (a), step (b), step (c) and so on. For example, when step (c) leads to improvement in one or more AD-associated parameter or patient-related outcome as described herein, the one or more repeat of steps (a) and (b) may maintain the one or more AD-associated parameter or patient-related outcome. When the subject reaches a low disease state by administering one or more tertiary dose(s) of the IL-13 binding protein to the subject, the one or more repeat of steps (a) and (b) may maintain the low disease state. For example, the one or more tertiary dose(s) may achieve an Investigator's Global Assessment (IGA) score of 0 or 1 and/or ≥75% improvement of Eczema Area and Severity Index (EASI-75) over baseline in a subject, which is then maintained by the one or more repeat of method steps (a) and (b).

In some embodiments, each dose (the first dose and one or more secondary dose(s), and optionally the one or more prior dose(s) and/or one or more tertiary dose(s)) is the same amount (in milligrams) of the of the IL-13 binding protein, for example, from about 10 mg to about 600 mg of the IL-13 binding protein, from about 50 mg to 500 mg, from about 100 mg to about 400 mg, from about 250 mg to about 350 mg or from about 280 mg to about 320 mg of IL-13 binding protein. In particular, each dose may be about 10 mg, about 25 mg, about 50 mg, about 100 mg, about 150 mg, about 200 mg, about 250 mg, about 300 mg, about 400 mg or about 500 mg. In some cases, the dose is 600 mg or less, 500 mg or less, 400 mg or less, 300 mg or less, 200 mg or less or 200 mg or less. In preferred embodiments, each dose (i.e. the first dose and one or more secondary dose(s), and optionally the one or more prior dose(s) and/or one or more tertiary dose(s)) is about 300 mg of IL-13 binding protein (e.g. as illustrated in the examples).

In some embodiments the very first dose of said one or more prior doses and/or said one or more tertiary doses is a bolus dose which is double the amount of the doses following the bolus dose.

In some embodiments the very first dose of said one or more prior doses and/or said one or more tertiary doses is 600 mg dose and the dose(s) following the 600 mg dose is 300 mg dose(s).

In some embodiments a bolus dose is given as a first dose of the above mentioned "one or more prior doses" or as the first dose in step (c). The bolus is typically twice the amount of the dose administered with the next administration. For example, a dose of 600 mg is used as a bolus dose when the next dose administered is 300 mg, and a dose of 300 mg is used as a bolus dose when the next dose administered is 600 mg.

In some cases, the one or more prior dose(s) and the one or more tertiary dose(s) may be administered to the subject at the same dosing frequency interval (e.g. about 2 weeks after the immediately preceding dose).

Administration

In the methods described herein, the IL-13 binding protein (e.g. an anti-IL-13 antibody or an IL-13-binding fragment thereof) may be administered by any appropriate method. Typically, administration is parenteral, e.g. intradermal, intramuscular, intravenous and subcutaneous. Subcutaneous administration is particularly preferred (e.g. as illustrated in the examples). Each dose of the IL-13 binding protein may therefore be administered subcutaneously.

Administration is preferably in a "therapeutically effective amount", this being sufficient to show improvement or maintained improvement in one or more AD-associated parameter or patient-related outcome as described herein, or achievement of a low disease state.

Administration may be by any convenient route, for example by infusion or bolus injection, by absorption through epithelial or mucocutaneous linings (e.g. oral mucosa, rectal and intestinal mucosa, etc.).

Subcutaneous or intravenous delivery may be with a standard needle and syringe (e.g. including with a prefilled syringe). It is envisaged that the methods described herein will not be restricted to use in the clinic. Therefore, subcutaneous injection using a needle free device is also preferred. Such delivery devices can be reusable or disposable. Numerous reusable pen and autoinjector delivery devices are known in the art and may find use in the present invention. Examples include AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ 1, 11 and 111 (Nova Nordisk, Copenhagen, Denmark), NOVOPEN JUNIOR™ (Nova Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (Sanofi-Aventis, Frankfurt, Germany). Exemplary disposable pen delivery devices for subcutaneous delivery that may find use in the present invention applications include the SOLOSTAR™ pen (Sanofi-Aventis), the FLEXPEN™ (Nova Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park Ill.).

Each dose of IL-13 binding protein of is not necessarily administered in a single administration step (e.g. one injection or one tablet etc.). Indeed, depending on the concentration of the IL-13 binding protein (e.g. in the pharmaceutical composition), one, two, three or more administration steps (e.g. one, two, three or more injections) may be required to provide the subject with the required amount IL-13 binding protein (e.g. a 300 mg dose, for example). Thus, in some embodiments, each dose of the IL-13 binding protein is administered in one or two injections (e.g. subcutaneously). Typically subcutaneous injections have a volume of around 1.5 mL or less, such as a volume of from 0.2 to 1.5 mL, e.g. around 1 mL.

Monotherapy and Combination Therapy

The methods described herein may be a monotherapy (e.g. as in Examples 4 and 5). As used herein, the term "monotherapy" is a therapy which uses a single drug to treat a disease or condition. Therefore, a subject that is treated with a monotherapy will receive only a single drug to treat the relevant disorder, e.g. AD, a skin infection, pruritus or eczema-related sleep interference. For example, an anti-IL-13 antibody monotherapy refers to a monotherapy which comprises the administration of anti-IL-13 antibody to the subject as the sole drug for the treatment of AD or a skin infection.

The methods described herein may be a combination therapy (e.g. as in Examples 1-3). As used herein, the term "combination therapy" is a therapy which uses more than one drug to treat a disease or condition. For example, a subject that is treated with a combination therapy will receive more than one drug (e.g. two, three or more) to treat AD.

In some embodiments, the IL-13 binding protein is administered in combination with a topical therapy (such as a topical corticosteroid or a topical calcineurin inhibitor). In some instances, the additional treatment (e.g. TCS or TCI) is administered as needed by the subject.

In some cases, the IL-13 binding protein is administered in combination with a second therapeutic agent selected from the group consisting of a topical corticosteroid, a topical calcineurin inhibitor, an anti-histamine, an emollient, or an anti-bacterial therapeutic. In some cases, the IL-13 binding protein is administered in combination with a Group I, Group II, Group III or Group IV corticosteroid. Preferably, the IL-13 binding protein can be administered in combination with mometasone furoate (e.g. 0.1% cream), as illustrated in Example 1.

Pharmaceutical Compositions and Formulations

The present invention envisages methods where each dose of the IL-13 binding protein (e.g. an anti-IL-13 antibody or an IL-13-binding fragment thereof) is administered as a pharmaceutical composition.

The pharmaceutical compositions may be formulated with suitable carriers, excipients, and other agents that provide suitable transfer, delivery, tolerance, and the like. A multitude of formulations can be found in the formulary known to all pharmaceutical chemists: Remington's Pharmaceutical Sciences, Mack Publishing Company, Easton, PA.

The dose administered to a patient according to the methods described herein may be varied depending upon the age and the size of the patient, symptoms, conditions, route of administration, and the like. The dose can be calculated according to body weight or body surface area.

Thus, the pharmaceutical compositions may comprise, in addition to the active ingredient (i.e. the IL-13 binding protein), a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous or subcutaneous. Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection or subcutaneous injection, the pharmaceutical composition may be a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The pharmaceutical composition may be a liquid formulation or a lyophilized formulation which is reconstituted before use. As excipients for a lyophilized formulation, for example, sugar alcohols, or saccharides (e.g. mannitol or glucose) may be used. In the case of a liquid formulation, the pharmaceutical composition is usually provided in the form of containers with defined volume, including sealed and sterilized plastic or glass vials, ampoules and syringes, as well as in the form of large volume containers like bottles. Preferably, in the methods described herein, the pharmaceutical composition is a liquid formulation.

Exemplary pharmaceutical compositions that can be used in the context of the present invention are disclosed in, for example, WO 2007/036745 and WO 2018/158332.

Preferably, the IL-13 binding protein may be present within the pharmaceutical composition at a concentration of from 1 mg/mL to 200 mg/mL, more preferably 150 mg/mL.

Preferably, the pharmaceutical composition may be buffered to a pH of 5.2 to 5.7, most preferably 5.5 (e.g. ±0.1). The selection of such a pH confers significant stability to the pharmaceutical composition. Examples of alternative buffers that control the pH in this range include succinate, gluconate, histidine, citrate, phosphate, glutarate, cacodylate, sodium hydrogen maleate, tris(hydroxymethyl)aminomethane (Tris), 2-(N-morpholino) ethanesulphonic acid (MES), imidazole. Preferably, the buffer is acetate buffer, more preferably sodium acetate buffer.

Preferably, the acetate buffer is present within the pharmaceutical composition in an amount of from 1 mM to 100 mM, more preferably from 30 mM to 70 mM, especially 50 mM.

It will be appreciated that references to "pharmaceutically acceptable excipient" includes references to any excipient conventionally used in pharmaceutical compositions. Such excipients may typically include one or more surfactant, inorganic or organic salt, stabilizer, diluent, solubilizer, reducing agent, antioxidant, chelating agent, preservative and the like.

Examples of a typical surfactant include: nonionic surfactants (HLB 6 to 18) such as sorbitan fatty acid esters (e.g. sorbitan monocaprylate, sorbitan monolaurate, sorbitan monopalmitate), glycerine fatty acid esters (e.g. glycerine monocaprylate, glycerine monomyristate, glycerine monostearate), polyglycerine fatty acid esters (e.g. decaglyceryl monostearate, decaglyceryl distearate, decaglyceryl monolinoleate), polyoxyethylene sorbitan fatty acid esters (e.g. polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate), polyoxyethylene sorbitol fatty acid esters (e.g. polyoxyethylene sorbitol tetrastearate, polyoxyethylene sorbitol tetraoleate), polyoxyethylene glycerine fatty acid esters (e.g. polyoxyethylene glyceryl monostearate), polyethylene glycol fatty acid esters (e.g. polyethylene glycol distearate), polyoxyethylene alkyl ethers (e.g. polyoxyethylene lauryl ether), polyoxyethylene polyoxypropylene alkyl ethers (e.g. polyoxyethylene polyoxypropylene glycol ether, polyoxyethylene polyoxypropylene propyl ether, polyoxyethylene polyoxypropylene cetyl ether), polyoxyethylene alkylphenyl ethers (e.g. polyoxyethylene nonylphenyl ether), polyoxyethylene hydrogenated castor oils (e.g. polyoxyethylene castor oil, polyoxyethylene hydrogenated castor oil), polyoxyethylene beeswax derivatives (e.g. polyoxyethylene sorbitol beeswax), polyoxyethylene lanolin derivatives (e.g. polyoxyethylene lanolin), and polyoxyethylene fatty acid amides (e.g. polyoxyethylene stearyl amide); anionic surfactants such as C10-C18 alkyl sulfates salts (e.g. sodium cetyl sulfate, sodium lauryl sulfate, sodium oleyl sulfate), polyoxyethylene C10-C18 alkyl ether sulfates salts with an average of 2 to 4 moles of ethylene oxide (e.g. sodium polyoxyethylene lauryl sulfate), and C8-C18 alkyl sulfosuccinate ester salts (e.g. sodium lauryl sulfosuccinate ester); and natural surfactants such as lecithin, glycerophospholipid, sphingophospholipids (e.g. sphingomyelin), and sucrose esters of C12-C18 fatty acids. The surfactant may be selected from polyoxyethylene sorbitan fatty acid esters. Preferred surfactants are polysorbate 20, 21, 40, 60, 65, 80, 81 and 85, most preferably polysorbate 20 and 80, especially polysorbate 80.

Preferably, the surfactant is present within the pharmaceutical composition in an amount of from 0.001% to 0.1% (w/w), more preferably 0.005% and 0.05% (w/w), especially 0.01% (w/w).

Examples of a typical inorganic salt include: sodium chloride, potassium chloride, calcium chloride, sodium phosphate, sodium sulphate, ammonium sulphate, potassium phosphate and sodium bicarbonate or any other sodium, potassium or calcium salt. Preferably, the inorganic salt is sodium chloride.

Preferably, the inorganic salt is present within the pharmaceutical composition in an amount of from 10 mM to 200 mM, more preferably from 60 mM to 130 mM, especially 85 mM.

Examples of a reducing agent include N-acetylcysteine, Nacetylhomocysteine, thioctic acid, thiodiglycol, thioethanolamine, thioglycerol, thiosorbitol, thioglycolic acid and a salt thereof, sodium thiosulfate, glutathione, and a C1-C7 thioalkanoic acid.

Examples of an antioxidant include erythorbic acid, dibutylhydroxytoluene, butylhydroxyanisole, alpha-tocopherol, tocopherol acetate, L-ascorbic acid and a salt thereof, L-ascorbic acid palmitate, L-ascorbic acid stearate, sodium bisulfite, sodium sulfite, triamyl gallate and propyl gallate.

Examples of a chelating agent include disodium ethylenediaminetetraacetate (EDTA), sodium pyrophosphate and sodium metaphosphate.

Examples of a stabiliser include creatinine, an amino acid selected from histidine, alanine, glutamic acid, glycine, leucine, phenylalanine, methionine, isoleucine, proline, aspartic acid, arginine, lysine and threonine, a carbohydrate selected from sucrose, trehalose, sorbitol, xylitol and mannose, surfactants selected from polyethylene glycol (PEG; e.g. PEG3350 or PEG 4000) or polyoxyethylene sorbitan fatty acid esters (e.g. polysorbate 20 or polysorbate 80), or any combination thereof.

In one preferred embodiment the stabiliser comprises a single carbohydrate (e.g. trehalose).

In an alternatively preferred embodiment the stabilizer comprises an amino acid in combination with a carbohydrate (e.g. trehalose and alanine or trehalose, alanine and glycine).

In a further alternatively preferred embodiment the stabiliser comprises an amino acid in combination with a carbohydrate and a surfactant (e.g. trehalose, alanine and PEG3350; trehalose, proline and PEG3350; trehalose, alanine and polysorbate 80; trehalose, proline and polysorbate 80; trehalose, alanine, glycine and PEG3350; trehalose, alanine, glycine and polysorbate 80).

In a yet further alternatively preferred embodiment the stabiliser comprises an amino acid in combination with a surfactant (e.g. alanine and PEG3350 or alanine, glycine and PEG3350).

In a yet further alternatively preferred embodiment the stabiliser comprises a carbohydrate in combination with a surfactant (e.g. trehalose and PEG3350 or trehalose and polysorbate 80).

Examples of a preservative include octadecyldimethylbenzyl ammonium chloride, hexamethonium chloride, benzalkonium chloride (a mixture of alkylbenzyldimethylammonium chlorides in which the alkyl groups are long chain compounds), benzethonium chloride, aromatic alcohols such as phenol, butyl and benzyl alcohol, alkyl parabens such as methyl or propyl paraben, catechol, resorcinol, cyclohexanol, 3-pentanol, and m-cresol. In a preferred embodiment, the pharmaceutical composition comprises an IL-13 binding protein as described herein, a surfactant and an inorganic salt buffered to a pH of 5.5±0.1 with acetate buffer.

In a further preferred embodiment, the pharmaceutical composition comprises an IL-13 binding protein as described herein, sodium chloride and polysorbate 80, buffered to a pH of 5.5±0.1 with sodium acetate buffer.

In a yet further preferred embodiment, the pharmaceutical composition comprises an IL-13 binding protein as described herein (e.g. tralokinumab), 50 mM sodium acetate buffer, 85 mM sodium chloride, 0.01% (w/v) polysorbate 80, wherein the pharmaceutical composition has a pH of 5.5.

In a yet further preferred embodiment, the pharmaceutical composition comprises 150 mg/mL of an IL-13 antibody (e.g. tralokinumab), 50 mM sodium acetate buffer, 85 mM sodium chloride, 0.01% (w/v) polysorbate 80, wherein the pharmaceutical composition has a pH of 5.5.

Other Definitions

Unless defined otherwise, all technical and scientific terms used herein have the same meaning as commonly understood to one of ordinary skill in the art to which this invention belongs.

The articles "a" and "an" refer to one or to more than one (i.e., to at least one) of the grammatical object of the article. By way of example, "an element" means one element or more than one element.

The terms "comprise" and "comprising" are used in the inclusive, open sense, meaning that additional elements may be included.

In general, methods "comprising" a number of steps do not require the steps to be performed in a particular order. Where a method comprises a number of sequentially numbered or alphabetical steps (e.g. (1), (2), (3); (i), (ii), (iii); or (a), (b), (c) etc.), this implies that the steps must be performed in the prescribed order unless stated otherwise. The term "including" is used herein to mean "including but not limited to".

The term "about" in relation to a numerical value x is optional and means, for example, x±10%.

Generally, the terms "treat", "treating", "treatment", or the like, mean to alleviate (reduce, minimise, or eliminate) symptoms, or to reduce, minimise or eliminate the causation of symptoms either on a temporary or permanent basis. All publications mentioned herein are incorporated by reference in their entirety.

EXAMPLES

The invention is further illustrated by the following examples. It will be appreciated that the examples are for illustrative purposes only and are not intended to limit the invention as described above. Modification of detail may be made without departing from the scope of the invention.

Example 1: Tralokinumab/TCS Combination Therapy is Effective in Treating Moderate to Severe Atopic Dermatitis A Phase 3 trial (EZCTRA 3) was conducted to assess the efficacy and safety of a combination therapy of tralokinumab and (as needed) topical corticosteroid (TCS) in moderate-to-severe AD.

Methods

This was a double-blind, randomized 32 week study (NCT03363854). Patients with moderate-to-severe AD (IGA of 3 or 4) were randomized 2:1 and administered subcutaneous tralokinumab 300 mg (Q2W+TCS) or control (placebo Q2W+TCS) every 2 weeks. A loading dose of 600 mg Tralokinumab or placebo was given on day 0. Throughout the entire treatment period, all patients applied a thin layer of supplied TCS as needed (mometasone furoate 0.1% cream; Europe: Class 3 [potent]; US: Class 4 [midstrength]); provided in kit sizes of 180-200 g at each visit) once daily to areas with active lesions. An additional lower potency TCS or topical calcineurin inhibitor [TCI] was prescribed if needed for use on body areas where the supplied TCS was inadvisable, areas of thin skin (e.g., face, skin fold areas, genital areas), or on areas where continued treatment with TCS was considered unsafe. TCS use was continually monitored for safety and appropriateness and was discontinued gradually when control was achieved. Patients were instructed to return used and unused tubes at each trial visit to allow measurement of the amount of TCS used. An emollient was applied twice daily (or more, as needed) for at least 14 days before randomization and throughout the trial (including safety follow-up). For lesional skin, emollient was only applied when TCS was not applied. Rescue treatment in the form of topical and systemic medications was permitted to control intolerable AD symptoms. Patients receiving higher potency TCS (Europe: Class >3; US: Class <4) continued treatment, while those receiving systemic corticosteroids or nonsteroidal systemic immunosuppressive drugs temporarily discontinued treatment until cessation of rescue (and a 5 half-life washout for systemic treatment).

Primary endpoints were an Investigator's Global Assessment (IGA) score of 0 or 1 (IGA-0/1; clear or almost clear skin) and ≥75% improvement of Eczema Area and Severity Index (EASI-75) at week 16. At baseline, 46.3% of 380 randomized patients had severe AD (IGA-4). The mean baseline EASI score was 29.4. Additional secondary endpoints were the amount of TCS used and number of days without TCS use.

At week 16, tralokinumab responders (IGA-0/1 and/or EASI-75) were re-randomized 1:1 to tralokinumab Q2W or every 4 weeks (Q4W)+TCS for an additional 16 weeks. Placebo responders continued placebo Q2W+TCS; all non-responders received tralokinumab Q2W+TCS.

TABLE 2

Demographic and clinical characteristics of randomized patients at baseline

| Characteristic | All randomized (N = 380) | Placebo every other week + TCS (N = 127) | Tralokinumab every other week + TCS (N = 253) |
|---|---|---|---|
| Median age, years (IQR) | 36.0 (27.0-51.0) | 34.0 (24.0-50.0) | 37.0 (28.0-52.0) |
| Sex, n (%) | | | |
| Male | 209 (55.0) | 84 (66.1) | 125 (49.4) |
| Female | 171 (45.0) | 43 (33.9) | 128 (50.6) |
| Race, n (%) | | | |
| White | 288 (75.8) | 85 (66.9) | 203 (80.2) |
| Black or African American | 35 (9.2) | 12 (9.4) | 23 (9.1) |
| Asian | 41 (10.8) | 24 (18.9) | 17 (6.7) |
| Native Hawaiian or other Pacific Islander | 2 (0.5) | 1 (0.8) | 1 (0.4) |
| Other | 14 (3.7) | 5 (3.9) | 9 (3.6) |
| Median duration of AD, years (IQR) | N = 379 26.0 (17.0-39.0) | N = 126 26.0 (18.0-39.0) | N = 253 27.0 (17.0-39.0) |
| Median BSA, % (IQR) | 41.0 (28.0-69.5) | 40.0 (26.0-74.0) | 41.0 (30.0-63.0) |
| IGA, n (%) | | | |
| Moderate | 202 (53.2) | 66 (52.0) | 136 (53.8) |
| Severe | 176 (46.3) | 60 (47.2) | 116 (45.8) |
| Missing* | 2 (0.5) | 1 (0.8) | 1 (0.4) |
| Median EASI score (IQR) | N = 378 25.5 (19.2-37.1) | N = 126 26.5 (19.9-39.3) | N = 252 24.7 (18.4-35.9) |
| Median | N = 378 | N = 126 | N = 252 |

TABLE 2-continued

Demographic and clinical characteristics of randomized patients at baseline

| Characteristic | All randomized (N = 380) | Placebo every other week + TCS (N = 127) | Tralokinumab every other week + TCS (N = 253) |
|---|---|---|---|
| SCORAD total score (IQR) | 66.5 (57.9-77.6) | 67.9 (59.4-79.0) | 66.2 (57.6-76.3) |
| Median | N = 375 | N = 125 | N = 250 |
| DLQI score (IQR) | 18.0 (12.0-23.0) | 18.0-(12.0-23.0) | 18.0 (12.0-23.0) |
| Median | N = 377 | N = 126 | N = 251 |
| weekly average of worst daily pruritus NRS score (IQR) | 8.0 (6.6-8.9) | 8.0 (7.0-9.0) | 8.0-(6.6-8.7) |
| History of allergic conjunctivitis (atopy form), n (%) | | | |
| Current | 84 (22.1) | 26 (20.5) | 58 (22.9) |
| Past | 45 (11.8) | 11 (8.7) | 34 (13.4) |
| History of asthma (atopy form), n (%) | | | |
| Current | 177 (46.6) | 58 (45.7) | 119 (47.0) |
| Past | 47 (12.4) | 19 (15.0) | 28 (11.1) |
| History of atopic keratoconjunctivitis (atopy form), n(%) | | | |
| Current | 13 (3.4) | 5 (3.9) | 8 (3.2) |
| Past | 6 (1.6) | 4 (3.1) | 2 (0.8) |
| History of food allergy (atopy form), n (%) | | | |
| Current | 138 (36.3) | 48 (37.8) | 90 (35.6) |
| Past | 12 (3.2) | 3 (2.4) | 9 (3.6) |
| History of hay fever (atopy form), n (%) | | | |
| Current | 210 (55.3) | 69 (54.3) | 141 (55.7) |
| Past | 20 (5.3) | 3 (2.4) | 17 (6.7) |

*Patients did not receive a treatment dose and were not included in the FAS.

Results

Tralokinumab Treatment Significantly Improved IGA and EASI Scores after 16 Weeks 380 patients were randomized in the initial treatment period; 253 to tralokinumab plus TCS every other week and 127 to placebo plus TCS every other week. One patient from each treatment group withdrew from the trial before being dosed; therefore, 252 patients treated with tralokinumab plus TCS every other week and 126 patients treated with placebo plus TCS every other week were included in the full analysis and safety analysis sets. Continuation treatment (based on response at week 16 and initial treatment) was assigned to 353 patients.

Baseline demographics and disease characteristics were balanced across treatment groups, with approximately half of patients having severe disease (IGA-4) at baseline; median duration of AD was 26.0 years and median body surface area involvement was 41%. A number of patients had comorbid atopic diseases. All patients received prior therapy, with almost all receiving TCS (98.2%) and 61.6% used systemic steroids. Cyclosporine was the most common prior oral immunosuppressant used (31.1%).

There were significant differences between tralokinumab plus TCS and placebo plus TCS for both primary endpoints. More patients achieved IGA-0/1 and EASI-75 with tralokinumab plus TCS compared with placebo plus TCS at week 16. IGA-0/1 was achieved by 38.9% of patients who received tralokinumab plus TCS versus 26.2% of patients who received placebo plus TCS (p=0.015). EASI-75 was achieved by 56% of patients who received tralokinumab plus TCS versus 35.7% of patients who received placebo plus TCS (p<0.001). The sensitivity, secondary, and tertiary analyses supported the results of the primary analysis, FIG. 1.

Irrespective of IGA severity at baseline and history of atopic disease (asthma, food allergy and hay fever), the proportion of IGA-0/1 and EASI-75 responders was higher with tralokinumab plus TCS than placebo plus TCS. IGA-0/1 and EASI-75 response rates were higher in female patients and in patients aged ≥65 (tralokinumab plus TCS group only).

Rescue medication use was higher with placebo plus TCS (10.2%) than with tralokinumab plus TCS (2.8%).

Tralokinumab Treatment Reduced the Need for TCS Use

Rescue treatment was reported by 2.8% of tralokinumab-treated patients, compared to 10.2% of control patients. Significantly less TCS was used cumulatively by tralokinumab-treated than control patients over 16 weeks (134.9 g versus 193.5 g, 458.6 g; p=0.004). The number of TCS-free days (weekly average from eDiary, including lower potency TCS and TCI) was significantly higher for tralokinumab-treated compared to control patients at week 7 (Δ0.6 days; p=0.040) and from week 9 to 15 (range: Δ1.0 days; p=0.001 to Δ0.6 days; p=0.045). Tralokinumab-treated patients also had 0.5 more TCS-free days on average at week 16 (p=0.17).

At week 16, subjects in the tralokinumab group used 50% less of the supplied TCS compared to subjects who received placebo (p<0.001) [data not shown]. A greater proportion of patients used less than 5 g of TCS at week 15-16 with tralokinumab plus TCS (55.3%) versus placebo plus TCS (36.7%). The reduction in TCS use in the tralokinumab plus TCS treatment group was not compensated by use of lower potency TCS or TCI.

Results at week 16 may be seen in Table 3 below.

TABLE 3

Efficacy outcomes for initial treatment period: full analysis set

| Outcome | Placebo every other week + TCS (N = 126) | Tralokinumab every other week + TCS (N = 252) |
|---|---|---|
| Primary endpoints | | |
| IGA-0/1 at week 16, n (%) *, † | 33/126 (26.2) | 98/252 (38.9) |
| Difference versus placebo every other week + TCS (95% CI)‡ | | 12.4 (2.9, 21.9) p = 0.015§ |
| EASI-75 at week 16, n (%)*, † | 45/126 (35.7) | 141/252 (56.0) |
| Difference versus placebo every other week + TCS (95% CI)‡ | | 20.2 (9.8, 30.6) p < 0.001§ |
| EASI, LS mean % change from baseline (±SE) | −55.3 (±3.2) | −71.3§ (±2.2) |
| Key secondary endpoints | | |
| Adjusted mean change from baseline in SCORAD at week 16 (SE)∥ | −26.8 (1.80) | −37.7 (1.25) |
| Difference versus placebo every other week + TCS (95% CI) | | −10.9 (−15.2 to −6.6) p < 0.001 |
| SCORAD 50, % responders† | 38.1 | 61.1§ |
| SCORAD, LS mean %-change from baseline (±SE)∥ | −40.0 (±2.6) | −55.9§ (±1.8) |
| Worst daily pruritus NRS (weekly average) reduction ≥4 at week 16, n/N (%)*, † | 43/126 (34.1) | 113/249¶ (45.4) |
| Difference versus placebo every other week + TCS (95% CI)‡ | | 11.3 (0.9, 21.6) p = 0.037§ |
| Adjusted mean change from baseline in DLQI at week 16 (SE)∥ | −8.8 (0.56) | −11.7 (0.39) |
| Difference versus placebo every other week + TCS (95% CI) | | −2.9 (−4.3 to −1.6) p < 0.001 |
| Additional secondary endpoints | | |
| Adjusted mean change from baseline in worst daily pruritus NRS (weekly average) at week 16 (SE)‡‡ | N = 100 −2.9 (0.21) | N = 221 −4.1 (0.15) |
| Difference versus placebo every other week + TCS (95% CI) | | −1.2 (−1.7 to −0.7) p < 0.001 |
| DLQI reduction ≥4 at week 16, n/N (%)† | 81/123§§ (65.9) | 207/248§§ (83.5) |
| Difference versus placebo every other week + TCS (95% CI)‡ | | 17.6 (8.0, 27.1) p < 0.001†† |
| Adjusted mean change from baseline in EASI at week 16 (SE)∥ | N = 108 −15.6 (0.96) | N = 229 −21.0 (0.67) |
| Difference versus placebo every other week + TCS (95% CI) | | −5.4 (−7.7 to −3.1) p < 0.001 |
| EASI-50 at week 16, n (%)† | 73/126 (57.9) | 200/252 (79.4) |
| Difference versus placebo every other week + TCS (95% CI)‡ | | 21.3 (11.3, 31.3) p < 0.001†† |
| EASI-90 at week 16, n (%)† | 27/126 (21.4) | 83/252 (32.9) |
| Difference versus placebo every other week + TCS (95% CI)‡ | | 11.4 (2.1, 20.7) p = 0.022†† |
| Cumulative amount of TCS used at week 16, adjusted geometric mean (Se)∥ | N = 108 98.6 (1.14) | N = 229 58.6 (1.10) |
| Ratio of means (95% CI) | | 0.6 (0.4, 0.8) p = 0.002 |
| Other endpoints | | |
| Adjusted mean change from baseline in SCORAD at week 2 (SE) | −16.4 (1.33) | −20.6 (0.93) |
| Difference versus placebo every other week + TCS (95% CI) | | −4.2 (−7.4 to −1.0) p = 0.010 |
| Adjusted mean change from baseline in DLQI at week 2 (SE) | −7.3 (0.53) | −8.9 (0.37) |
| Difference versus placebo every other week + TCS (95% CI) | | −1.7 (−2.9 to −0.4) p = 0.011 |

TABLE 3-continued

Efficacy outcomes for initial treatment period: full analysis set

| Outcome | Placebo every other week + TCS (N = 126) | Tralokinumab every other week + TCS (N = 252) |
|---|---|---|
| Adjusted mean change from baseline in worst daily pruritus NRS (weekly average) at week 1 (SE) | N = 125<br>−1.3 (0.13) | N = 248<br>−1.5 (0.09) |
| Difference versus placebo | | −0.2 (−0.6 to −0.1)<br>p = 0.14 |

*Mean across multiple imputations, where applicable;

†Patients who received rescue medication considered nonresponders. Patients with missing data at week 16 imputed as nonresponders;

‡Mantel-Haenszel risk difference, stratified by region and baseline IGA;

§Single imputation analyses: Cochran-Mantel-Haenszel test, stratified by region and baseline IGA. Multiple imputation analyses: Combined inference from multiple Mantel-Haenszel risk differences and associated SE;

∥Data collected after permanent discontinuation of IMP or initiation of rescue medication not included. Repeated measurements model on post-baseline data: Change = Treatment * Week + Baseline * Week + Region + Baseline IGA. In case of no postbaseline assessments before initiation of rescue medication, the week 2 change is imputed as 0;

¶Based on patients in FAS with a baseline pruritus NRS weekly average of at least 4;

**Based on patients in FAS with a baseline pruritus NRS weekly average of at least 3;

††Cochran-Mantel-Haenszel test, stratified by region and baseline IGA;

‡‡Data collected after permanent discontinuation of IMP or initiation of rescue medication not included. Repeated measurements model: Change = Treatment * Week + Baseline * Week + Region + Baseline IGA. In case of no postbaseline assessments before initiation of rescue medication, the week 1 change is imputed as 0;

§§Analysis only includes patients with baseline DLQI ≥ 4.

∥∥Data collected after permanent discontinuation of IMP or initiation of rescue medication not included. The response variable was the logarithm of the [cumulative amount of TCS + 1]. Estimated parameters are back transformed using exponential function. A value of one was subtracted from the back-transformed adjusted mean and CI limits to account for adding the same factor before data transformation. Repeated measurements model: log[cumulative TCS amount + 1] (g) = Treatment * Week + Region + Baseline IGA.

Other endpoint results may be seen in Table 4 below:

TABLE 4

| | Combination therapy | |
|---|---|---|
| | ECZTRA 3 week 16 | |
| | Placebo + TCS | TRADENAME 300 mg Q2 W + TCS |
| Patients randomised | 126 | 252 |
| Eczema-related sleep NRS, LS mean change from baseline (SE)[a] | −3.1 (0.22) | −4.3[§] (0.15) |
| POEM, LS mean change from baseline (SE)[a] | −7.8 (0.66) | −11.8[§] (0.46) |
| POEM (≥4-point improvement), responders[b] | 59.3% (73/123) | 78.4%[§] (190/250) |

Least squares, SE: Standard error If needed to control intolerable symptoms of atopic dermatitis, patients were permitted to receive rescue treatment at the discretion of the investigator.

[a]Data after initiation of rescue medication or permanent discontinuation of treatment was excluded from the analyses.

[b]Subjects who received rescue treatment or had missing data were treated as nonresponders. The percentage is calculated relative to the number of subjects with POEM ≥4 at baseline §p < 0.001.

Other endpoint results for patients achieving clinical response at week 16 may be seen in Table 5:

TABLE 5

| | Treatment regimen Week 16-32[a] Responders at Week 16[b] | | | |
|---|---|---|---|---|
| | Q2 W + TCS | | Q4 W + TCS | |
| | Patients randomised | | | |
| | N = 69 | | N = 69 | |
| | Week number | | | |
| | W 16 | W 32 | W 16 | W 32 |
| DLQI, LS mean change from baseline (SE)[c] | −14.0 (0.6) | −14.6 (0.6) | −13.9 (0.6) | −13.7 (0.6) |
| POEM, LS mean change from baseline (SE)[c] | −15.2 (0.7) | −15.6 (0.7) | −14.1 (0.7) | −13.9 (0.8) |
| Eczema-related sleep NRS, LS mean change from baseline (SE)[c] | −5.2 (0.3) | −5.5 (0.3) | −4.8 (0.3) | −5.2 (0.3) |
| DLQI (≥4-point improvement), % responders[d] | 98.5% (65/66) | 89.4% (59/66) | 100.0% (68/68) | 83.8% (57/68) |
| POEM (≥4-point improvement), % responders[d] | 89.7% (61/68) | 88.2% (60/68) | 94.1% (64/68) | 83.8% (57/68) |

LS: Least squares, SE: Standard error. If needed to control intolerable symptoms of atopic dermatitis, patients were permitted to receive rescue treatment at the discretion of the investigator.

[a]All patients were initially treated with TRADENAME 300 mg Q2 W + TCS from Week 0 to Week 16. They were subsequently treated with TRADENAME 300 mg Q2 W + TCS or Q4 W + TCS.

[b]Responders at Week 16 at are identified as patients achieving either IGA 0/1 and/or EASI75.

[c]Data after initiation of rescue medication or permanent discontinuation of treatment was excluded from the analyses.

[d]Number of responders divided by number of subjects having baseline value ≥4 of the given parameter.

Subjects who received rescue treatment or had missing data were treated as nonresponders.

Tralokinumab Response was Maintained Over 32 Weeks

Figure 6:
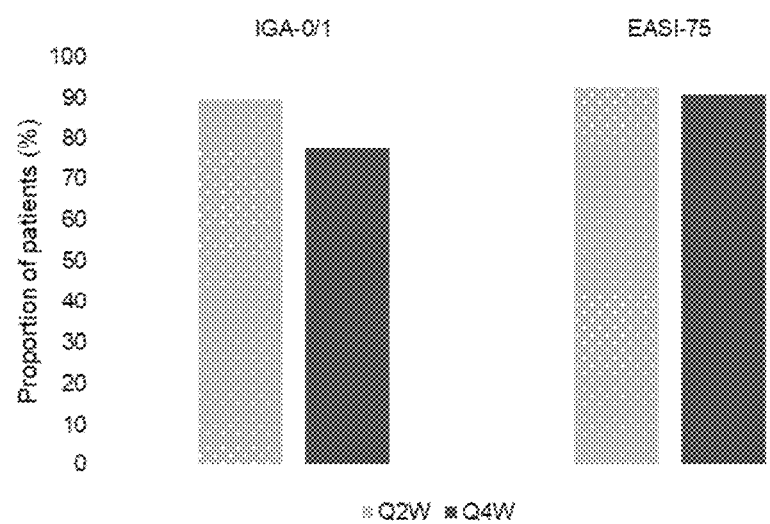
FIG. 6. Proportion of patients (%) achieving IGA-0/1 and EASI-75 at week 32. Patients were responders to tralokinumab/TCS treatment at week 16. At week 16 responders were split into two groups and treated with tralokinumab/TCS every 2 weeks (Q2W) or 4 weeks (Q4W) for the remainder of the study.
Figures 7A, 7B:
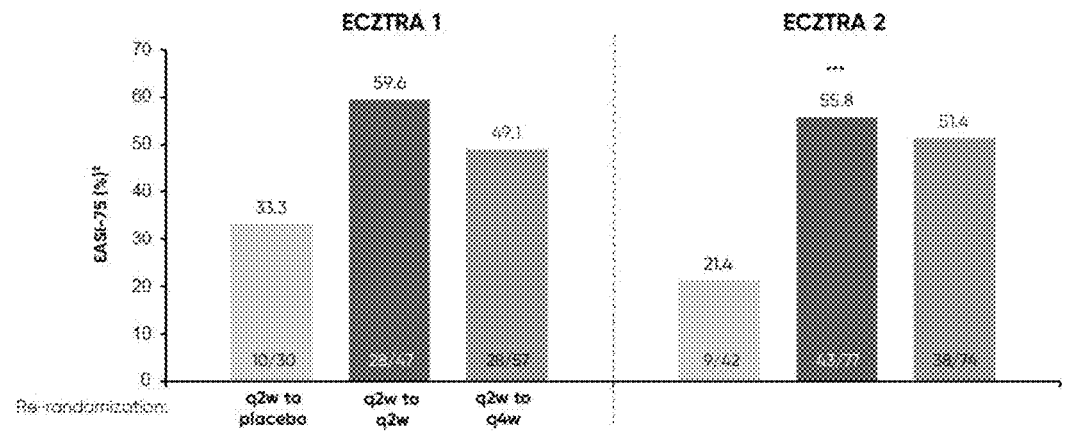
FIG. 7A. Proportion of patients (%) achieving EASI-75 at week 52 of ECZTRA 1 trials. Patients were responders to tralokinumab treatment at week 16. At week 16 responders were split into groups and treated with tralokinumab every 2 weeks (Q2W) or 4 weeks (Q4W) for the remainder of the study. ‡Assessed in patients achieving EASI-75 at week 16 without use of rescue medication after initial randomization to tralokinumab. Patients who, after week 16, received rescue medication or were transferred to open-label treatment were considered nonresponders at week 52; Missing values imputed as nonresponse.
FIG. 7B. Proportion of patients (%) achieving EASI-75 at week 52 of ECZTRA 2 trials. Patients were responders to tralokinumab treatment at week 16. At week 16 responders were split into groups and treated with tralokinumab every 2 weeks (Q2W) or 4 weeks (Q4W) for the remainder of the study. ‡Assessed in patients achieving EASI-75 at week 16 without use of rescue medication after initial randomization to tralokinumab. Patients who, after week 16, received rescue medication or were transferred to open-label treatment were considered nonresponders at week 52; Missing values imputed as nonresponse.
Figures 7C, 7D:
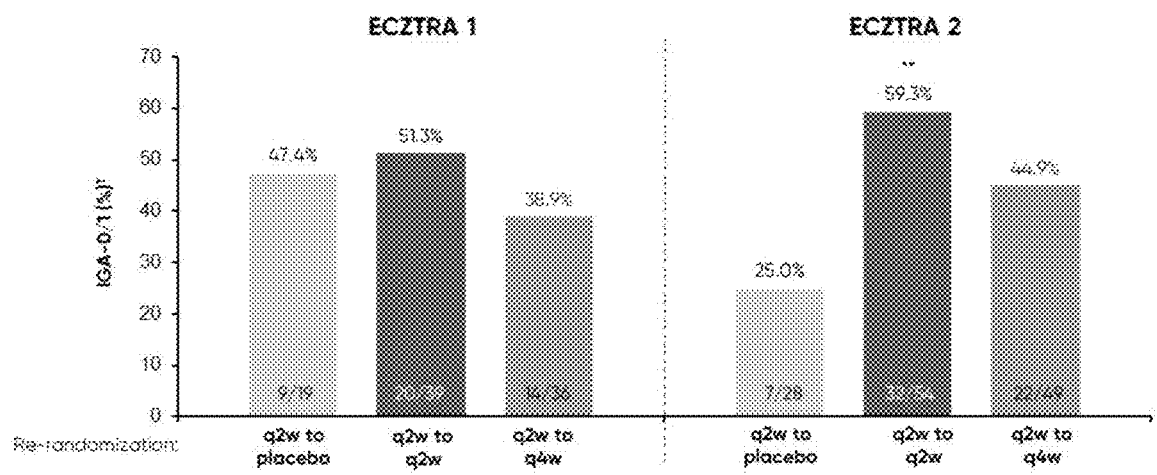
FIG. 7C. Proportion of patients (%) achieving IGA-0/1 at week 52 of ECZTRA 1 trials. Patients were responders to tralokinumab treatment at week 16. At week 16 responders were split into groups and treated with tralokinumab every 2 weeks (Q2W) or 4 weeks (Q4W) for the remainder of the study. †Assessed in patients achieving IGA-0/1 at week 16 without use of rescue medication after initial randomization to tralokinumab. Patients who, after week 16, received rescue medication or were transferred to open-label treatment were considered nonresponders at week 52; Missing values imputed as nonresponse.
FIG. 7D. Proportion of patients (%) achieving IGA-0/1 at week 52 of ECZTRA 2 trials. Patients were responders to tralokinumab treatment at week 16. At week 16 responders were split into groups and treated with tralokinumab every 2 weeks (Q2W) or 4 weeks (Q4W) for the remainder of the study. †Assessed in patients achieving IGA-0/1 at week 16 without use of rescue medication after initial randomization to tralokinumab. Patients who, after week 16, received rescue medication or were transferred to open-label treatment were considered nonresponders at week 52; Missing values imputed as nonresponse.

The majority of week 16 tralokinumab responders maintained their response at week 32 with tralokinumab, regardless of dosing frequency (2 week or 4 week). Among tralokinumab responders, 89.6% maintained an IGA-0/1 score and 92.5% maintained EASI-75 at week 32 when receiving tralokinumab every two weeks (Q2W+TCS). For tralokinumab Q4W+TCS, 77.6% achieved IGA-0/1 and 90.8% achieved EASI-75 at week 32. The results are shown in FIG. 6.

Among all the subjects who achieved either IGA 0 or 1 or EASI-75 at week 16, the mean percentage improvement in EASI score from baseline was 93.5% at week 32 when maintained on Tralokinumab 300 mg Q2W+TCS and 91.5% at week 32 for subjects on Tralokinumab 300 mg Q4W+TCS.

Of the patients who did not achieve IGA-0/1 and/or EASI-75 with tralokinumab (Q2W+TCS) at week 16, 30.5% and 55.8% achieved IGA-0/1 and EASI-75 respectively at week 32, following continued tralokinumab Q2W+TCS treatment Of the patients who achieved an EASI-75 or IGA-0/1 response at week 16 on tralokinumab plus TCS every other week, the majority were also EASI-90 responders and continued to maintain that response up to week 32, irrespective of continued every other week, or every 4 weeks dosing. Patients who did not achieve an EASI-75 or IGA-0/1 response at week 16 continued to improve with tralokinumab plus TCS every other week.

Other endpoints at week 16 and 32 are shown in Tables 6 and 7:

TABLE 6

| | Treatment regimen Week 16-32[d] | | | | | |
|---|---|---|---|---|---|---|
| | Responders at Week 16[e] | | | | Non-responders at Week 16 | |
| | Q2W + TCS | | Q4W + TCS | | Q2W + TCS | |
| | Patients randomised | | | | | |
| | N = 69 | | N = 69 | | N = 95 | |
| | Week number | | | | | |
| | W 16 | W 32 | W 16 | W 32 | W 16 | W 32 |
| EASI-50, % responders[a] | 100.0 | 98.6 | 97.1 | 91.3 | 63.2 | 76.8 |
| EASI-90, % responders[a] | 58.0 | 72.5 | 60.9 | 63.8 | 1.1 | 34.7 |
| EASI, LS % mean change from baseline (SE)[b] | −90.5 (2.7) | −93.2 (2.3) | −89.3 (2.7) | −91.5 (2.3) | −46.9 (2.4) | −73.5 (2.0) |
| SCORAD, LS % mean change from baseline (SE)[b] | −73.2 (2.1) | −79.2 (2.5) | −72.3 (2.1) | −73.3 (2.5) | −32.7 (1.8) | −54.5 (2.2) |
| Pruritus NRS (>4-point improvement, % responders)[a,c] | 63.2 | 70.6 | 64.2 | 61.2 | 27.4 | 38.9 |
| Pruritus NRS, mean change from baseline (SE)[b] | −5.0 (0.2) | −5.4 (0.2) | −4.6 (0.2) | −4.9 (0.2) | −3.0 (0.2) | −3.7 (0.2) |

LS: Least squares,
SE: Standard error.
If needed to control intolerable symptoms of atopic dermatitis, patients were permitted to receive rescue treatment at the discretion of the investigator.
[a]Patients who received rescue treatment or had missing data were considered non-responders in the analyses.
[b]Data after initiation of rescue medication or permanent discontinuation of treatment was excluded from the analyses.
[c]The percentage is calculated relative to the number of subjects with a baseline value >4.
[d]All patients were initially treated with TRADENAME 300 mg Q2W + TCS from Week 0 to Week 16. They were subsequently treated with TRADENAME 300 mg Q2W + TCS or Q4W + TCS
[e]Responders at Week 16 at are identified as patients achieving either IGA 0/1 and/or EASI75.

TABLE 7

| | Monotherapy | | | |
|---|---|---|---|---|
| | ECZTRA 1 week 16 | | ECZTRA 2 week 16 | |
| | Placebo | TRADENAME 300 mg Q2 W | Placebo | TRADENAME 300 mg Q2 W |
| Patients randomised | 199 | 603 | 201 | 593 |
| Eczema-related sleep NRS, LS mean change from baseline (SE)[a] | −1.9 (0.2) | −2.6[#] (0.1) | −1.5 (0.2) | −2.9[§] (0.1) |
| POEM, LS mean change from baseline (SE)[a] | −3.0 (0.66) | −7.6[§] (0.35) | −3.7 (0.66) | −8.8[§] (0.33) |
| POEM (≥4-point improvement), responders[b] | 18.0% (35/194) | 43.0%[§] (253/588) | 22.1% (44/199) | 54.4%[§] (319/586) |
| SF-36, physical component, LS mean change from baseline (SE)[a] | 2.9 (0.56) | 4.5* (0.30) | 3.2 (0.57) | 5.8[§] (0.29) |
| SF-36, mental component, LS mean change from baseline (SE)[a] | 0.3 (0.78) | 2.5* (0.42) | 0.5 (0.76) | 3.5[§] (0.38) |

LS: Least squares, SE: Standard error. If needed to control intolerable symptoms of atopic dermatitis, patients were permitted to receive rescue treatment at the discretion of the investigator.
[a]Data after initiation of rescue medication or permanent discontinuation of treatment was excluded from the analyses.
[b]Subjects who received rescue treatment or had missing data were treated as non-responders. The percentage is calculated relative to the number of subjects with POEM ≥4 at baseline
*$p < 0.05$,
$p < 0.01$,
§$p < 0.001$.

Tralokinumab has a Favorable Safety Profile

Table 8 shows the overall frequency and severity of adverse effects over 16 weeks.

Summary of AEs and AESIs in the 16 week initial treatment period

TABLE 8

| Event | Week 16* | |
|---|---|---|
| | Placebo every other week + TCS (N = 126, PYE = 37.94) | Tralokinumab every other week + TCS (N = 252, PYE = 75.03) |
| Adverse or serious adverse event, n (%) R | | |
| At least one adverse event | 84 (66.7) 485.0 | 180 (71.4) 671.7 |
| At least one serious adverse event | 4 (3.2) 10.54 | 2 (0.8) 2.67 |
| Severity | | |
| Mild | 69 (54.8) 347.9 | 157 (62.3) 511.8 |
| Moderate | 30 (23.8) 110.7 | 66 (26.2) 150.6 |
| Severe | 7 (5.6) 26.36 | 7 (2.8) 9.33 |
| Leading to discontinuation of IMP | 1 (0.8) 2.64 | 6 (2.4) 10.66 |
| Not recovered/not resolved | 13 (10.3) 47.4 | 48 (19.0) 80.0 |
| Recovering/resolving | 7 (5.6) 23.7 | 13 (5.2) 20.0 |
| Recovered/resolved | 78 (61.9) 413.8 | 167 (66.3) 563.7 |
| Recovered/resolved with sequelae | 0 | 3 (1..2) 4.0 |

TABLE 8-continued

| Event | Week 16* | |
|---|---|---|
| | Placebo every other week + TCS (N = 126, PYE = 37.94) | Tralokinumab every other week + TCS (N = 252, PYE = 75.03) |
| Frequent AEs (≥5% in any treatment group)[†] | | |
| Viral upper respiratory tract infection | 14 (11.1) 47.44 | 49 (19.4) 85.29 |
| Upper respiratory tract infection | 6 (4.8) 18.45 | 19 (7.5) 27.99 |
| Conjunctivitis[‡] | 4 (3.2) 10.54 | 28 (11.1) 42.65 |
| Injection site reaction | 0 | 17 (6.7) 39.98 |
| Dermatitis atopic | 10 (7.9) 31.63 | 6 (2.4) 10.66 |
| Headache | 6 (4.8) 23.72 | 22 (8.7) 34.65 |
| AESIs - eye disorders | 7 (5.6) 18.45 | 34 (13.5) 51.980 |
| Conjunctivitis[‡] | 7 (5.6) 18.45 | 33 (13.1) 50.64 |
| Keratoconjunctivitis | 0 | 1 (0.4) 1.44 |
| Keratitis | 0 | 0 |
| AESIs - skin infections requiring systemic treatment | 7 (5.6) 23.72 | 4 (1.6) 5.33 |
| AESIs - eczema herpeticum | 1 (0.8) 2.64 | 1 (0.4) 1.33 |
| AESIs - malignancies diagnosed after randomization | 0 | 0 |

*AEs collected during the exposure time in the initial treatment period are shown;
[†]Classification according to MedDRA 20.0;
[‡]PTs according to MedDRA 20.0 include conjunctivitis, conjunctivitis allergic and conjunctivitis viral Overall, the safety profile at week 32 was comparable with the initial treatment period, as shown in Table 9 below.

TABLE 9

| | Week 32[†] | | | | |
|---|---|---|---|---|---|
| | Week 16 tralokinumab responders | | Week 16 tralokinumab nonresponders | Week 16 placebo nonresponders | Week 16 placebo responders |
| Event, n (%) R | Tralokinumab Q2W + TCS (N = 69, PYE = 21.46) | Tralokinumab Q4W + TCS (N = 69, PYE = 20.7) | Tralokinumab Q2W + TCS (N = 95, PYE = 28.28) | Tralokinumab Q2W + TCS (N = 79, PYE = 22.99) | Placebo Q2W + TCS (N = 41, PYE = 12.25) |
| AEs | 48 (69.6) 540.5 | 41 (59.4) 439.6 | 62 (65.3) 654.2 | 55 (69.6) 552.5 | 26 (63.4) 359.3 |
| Severity | | | | | |
| Mild | 41 (59.4) 419.3 | 35 (50.7) 347.8 | 51 (53.7) 477.4 | 41 (51.9) 348.0 | 17 (41.5) 236.8 |
| Moderate | 16 (23.2) 111.8 | 12 (17.4) 91.78 | 30 (31.6) 173.3 | 25 (31.6) 195.8 | 12 (29.3) 122.5 |
| Severe | 2 (2.9) 9.32 | 0 | 1 (1.1) 3.54 | 2 (2.5) 8.70 | 0 |
| Leading to discontinuation of IMP | 0 | 1 (1.4) 4.83 | 1 (1.1) 3.54 | 2 (2.5) 8.70 | 1 (2.4) 8.17 |
| Leading to withdrawal from trial | 0 | 1 (1.4) 4.83 | 0 | 2 (2.5) 8.70 | 1 (2.4) 8.17 |

TABLE 9-continued

| | Week 32[†] | | | | |
| --- | --- | --- | --- | --- | --- |
| | Week 16 tralokinumab responders | | Week 16 tralokinumab nonresponders | Week 16 placebo nonresponders | Week 16 placebo responders |
| Event, n (%) R | Tralokinumab Q2 W + TCS (N = 69, PYE = 21.46) | Tralokinumab Q4 W + TCS (N = 69, PYE = 20.7) | Tralokinumab Q2 W + TCS (N = 95, PYE = 28.28) | Tralokinumab Q2 W + TCS (N = 79, PYE = 22.99) | Placebo Q2 W + TCS (N = 41, PYE = 12.25) |
| Recovered/resolved | 43 (62.3) 451.9 | 35 (50.7) 328.5 | 56 (58.9) 509.2 | 46 (58.2) 400.2 | 22 (53.7) 302.1 |
| SAEs | 3 (4.3) 18.64 | 0 | 2 (2.1) 7.07 | 0 | 1 (2.4) 8.17 |
| Frequent AEs (≥5% in any treatment group)[∥] | | | | | |
| Infections and infestations | 30 (43.5) 205.0 | 20 (29.0) 125.6 | 40 (42.1) 233.4 | 31 (39.2) 195.8 | 17 (41.5) 187.8 |
| Viral upper respiratory tract infection | 12 (17.4) 60.57 | 9 (13.0) 48.30 | 20 (21.1) 99.01 | 15 (19.0) 65.25 | 7 (17.1) 65.32 |
| Conjunctivitis | 3 (4.3) 13.98 | 0 | 3 (3.2) 10.61 | 3 (3.8) 13.05 | 1 (2.4) 8.17 |
| Upper respiratory tract infection | 7 (10.1) 37.27 | 3 (4.3) 14.49 | 6 (6.3) 24.75 | 3 (3.8) 13.05 | 2 (4.9) 16.3 |
| Oral herpes | 3 (4.3) 13.98 | 4 (5.8) 19.32 | 4 (4.2) 17.68 | 2 (2.5) 8.70 | 1 (2.4) 8.17 |
| General disorders and administration site conditions | 10 (14.5) 116.5 | 8 (11.6) 72.46 | 12 (12.6) 81.33 | 8 (10.1) 47.85 | 0 |
| Injection site reaction | 5 (7.2) 65.23 | 4 (5.8) 43.47 | 5 (5.3) 17.68 | 2 (2.5) 8.70 | 0 |
| Skin and subcutaneous tissue disorders | 4 (5.8) 27.95 | 2 (2.9) 9.66 | 14 (14.7) 70.72 | 10 (12.7) 43.50 | 2 (4.9) 16.33 |
| AD | 1 (1.4) 4.66 | 1 (1.4) 4.83 | 8 (8.4) 28.29 | 6 (7.6) 26.10 | 2 (4.9) 16.33 |
| Nervous system disorders | 5 (7.2) 23.30 | 8 (11.6) 38.64 | 9 (9.5) 31.83 | 4 (5.1) 17.40 | 1 (2.4) 8.17 |
| Headache | 2 (2.9) 9.32 | 5 (7.2) 24.15 | 7 (7.4) 24.75 | 2 (2.5) 8.70 | 1 (2.4) 8.17 |
| Gastrointestinal disorders | 6 (8.7) 51.25 | 7 (10.1) 53.13 | 9 (9.5) 45.97 | 12 (15.2) 60.90 | 3 (7.3) 32.66 |
| Nausea | 3 (4.3) 13.98 | 4 (5.8) 19.32 | 3 (3.2) 14.14 | 1 (1.3) 4.35 | 0 |
| AESIs - eye disorders | 3 (4.3) 13.98 | 1 (1.4) 4.83 | 4 (4.2) 14.14 | 6 (7.6) 34.80 | 2 (4.9) 16.33 |
| Conjunctivitis | 3 (4.3) 13.98 | 1 (1.4) 4.83 | 4 (4.2) 14.14 | 6 (7.6) 30.45 | 1 (2.4) 8.17 |
| Keratoconjunctivitis | 0 | 0 | 0 | 1 (1.3) 4.35 | 1 (2.4) 8.17 |
| AESIs - skin infections requiring systemic treatment | 0 | 0 | 1 (1.1) 3.54 | 2 (2.5) 8.70 | 0 |
| AESIs - eczema herpeticum | 0 | 0 | 1 (1.1) 3.54 | 1 (1.3) 8.70 | 0 |
| AESIs - malignancies diagnosed after randomization | 0 | 1 (1.4) 4.83 | 0 | 0 | 1 (2.4) 8.17 |

*AEs collected during the exposure time in the continuation treatment period are shown. Responders and nonresponders presented as treated. A responder was defined as having IGA-0/1 or EASI-75 at week 16;
[†]Classification according to MedDRA 20.0.

Overall, tralokinumab used for a period up to 32 weeks in combination with TCS was well-tolerated and had an acceptable safety profile in adults with moderate-to-severe AD. The most frequent AEs (in ≥5% patients in any treatment group) occurring in a greater proportion of patients treated with tralokinumab Q2W plus TCS versus placebo Q2W plus TCS were viral upper respiratory tract infection, conjunctivitis, headache, upper respiratory tract infection, and injection site reaction. Conjunctivitis (as a preferred term) occurred in 10.9% of patients receiving tralokinumab plus TCS (total i.e. all tralokinumab groups over the entire treatment period), which is greater than the 2.6% of patients who experienced conjunctivitis with tralokinumab (total) in the Phase 2 trial (Wollenberg et al., The Journal of Allergy and Clinical Immunology 2019; 143:135-141) and the 4.0% and 3.8% who experienced conjunctivitis with dupilumab as monotherapy (total) in SOLO1 and 2 (Simpson et al., The New England Journal of Medicine 2016; 375:2335-2348), but lower than the 17.8% who experienced conjunctivitis with dupilumab plus TCS (total) in LIBERTY AD CHRONOS (Blauvelt et al., Lancet 2017; 389:2287-2303). As an AESI, conjunctivitis was more frequently reported with tralokinumab Q2W plus TCS than placebo Q2W plus TCS at week 16 (13.1% versus 5.6%); however, these were all mild or moderate and most resolved. Notably, fewer skin infections requiring systemic treatment occurred with tralokinumab Q2W plus TCS compared to placebo Q2W plus TCS.

Tralokinumab+TCS was associated with lower rates of severe and serious infections, eczema herpeticum, and skin infections requiring systemic treatment versus placebo+TCS.

Conclusions

Tralokinumab 300 mg Q2W+TCS is efficacious in treating moderate-to-severe AD, with a favorable safety profile. TCS use is significantly lower in tralokinumab-treated patients than placebo, demonstrating the potential steroid-sparing effects of tralokinumab. Tralokinumab maintained efficacy in responders when the dosing frequency was 2 weeks. Surprisingly, a response was also maintained at a dosing frequency of 4 weeks.

Example 2: Tralokinumab/TCS Combination Therapy Improves Short Term Patient Reported Outcomes Patient-reported outcomes (PRO) were used to assess the benefits of these treatment regimens as experienced by the patients.

Methods

Patient reported outcomes (PROs) experienced by patients were investigated during the tralokinumab/TCS combination therapy trial described in Example 1. PROs included ≥4-point reduction in worst daily pruritus Numerical Rating Scale (NRS), reduction in eczema-related sleep interference, Patient-Oriented Eczema Measure (POEM), and change in Dermatology Life Quality Index (DLQI) scores.

At baseline the mean eczema-related sleep interference was 6.9, mean POEM was 22.3 and the mean DLQI score was 17.6. The baseline worst daily pruritus score was 7.7.

Results

Figure 2:
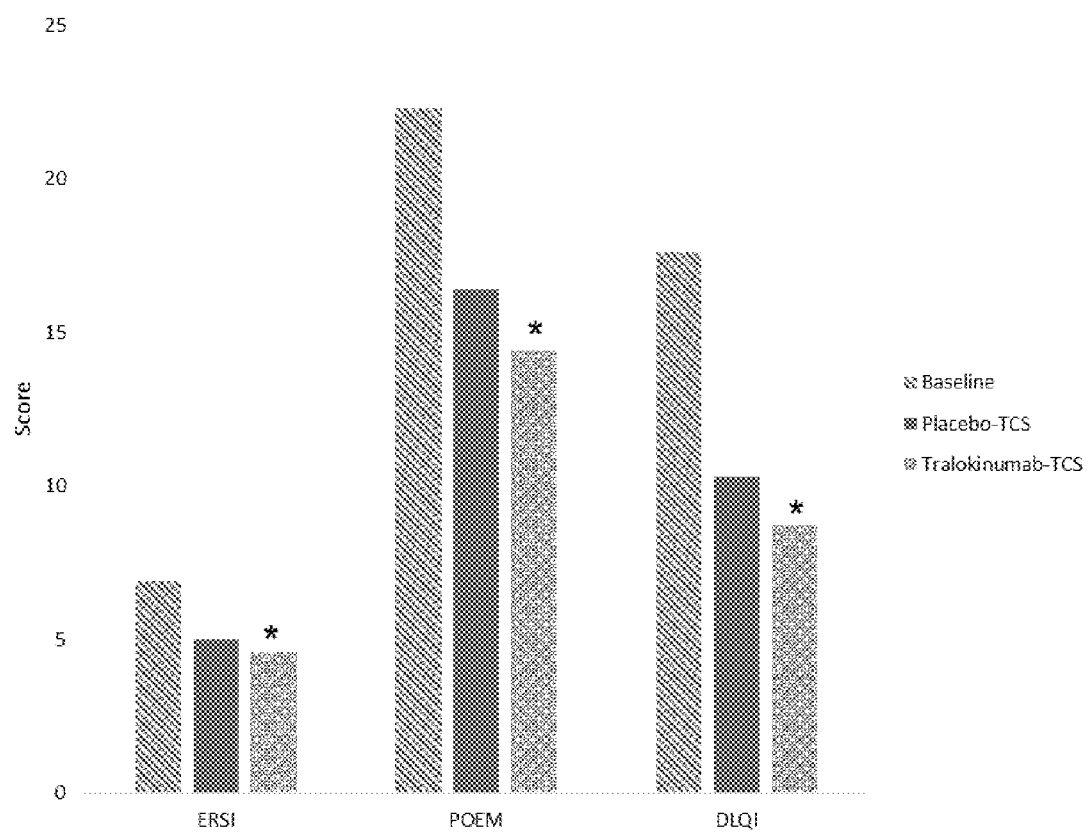
FIG. 2. Scores for patient reported outcomes at baseline and following 2 weeks of treatment with tralokinumab/TCS or placebo/TCS (control). ERSI=Eczema-Related Sleep Interference, POEM=Patient-Oriented Eczema Measure, DLQI=Dermatology Life Quality Index. *=significant difference compared to control (p<0.05).

Following 2 weeks of treatment, eczema-related sleep interference, Patient-Oriented Eczema Measure (POEM), and change in Dermatology Life Quality Index (DLQI) scores were significantly reduced in tralokinumab/TCS patients compared to placebo/TCS patients (FIG. 2). The mean eczema-related sleep interference decreased by 2.3 points compared to a decrease of 1.9 in the control group (p=0.037) (FIG. 2). Mean POEM was significantly reduced in the tralokinumab/TCS treatment group (−7.9 compared to −5.9 for placebo/TCS; p=0.006). The mean reported DLQI score decreased 8.9 points following tralokinumab/TCS treatment (compared to −7.3 for placebo/TCS; p=0.011). Mean improvements from baseline for DLQI and POEM reached the minimal clinical important difference (MCID) in addition to statistical significance.

By week 3, the proportion of patients with a ≥4-point reduction in worst daily pruritus from baseline was significantly higher with tralokinumab treatment, compared to the control group (27.3% compared to 17.5%; p=0.029).

FIGS. 9, 11A-11C and 12A-12C shows that tralokinumab/TCS significantly improved all secondary endpoints at week 16 versus placebo/TCS.

Conclusions

Early significant improvements in PROs were seen for tralokinumab/TCS combination therapy. Patients experience benefit from tralokinumab soon after treatment is initiated, with significant improvements following only 2 weeks of treatment.

Example 3: Further Analysis of Tralokinumab/TCS Combination Therapy Efficacy The Investigator's Global Assessment 0 or 1 (IGA 0/1; clear or almost clear skin) and/or ≥75% improvement of Eczema Area and Severity Index (EASI-75) assessed in Example 1 above are the regulatory primary efficacy endpoints in Phase 3 trials in AD. However, these endpoints do not comprehensively capture the full burden of AD.

Further analyses were used to assess the response to treatment with tralokinumab/TCS based on targets and timepoints typically used in clinical practice.

Methods

Data from the experiment described in Example 1 were further analysed to assess the patient response at 3 and 6 months after treatment with tralokinumab/TCS. The response was based on clinician-assessed signs (EASI), patient-reported symptoms (pruritus and POEM), and patient-reported quality of life scores (DLQI and Patient Global Impression of Bother (PGI-B)). The chosen time points reflected typical follow-up for adult AD patients initiating a new treatment. All 252 patients who received tralokinumab/TCS in Example 1 were included in this analysis.

Results

Table 10 shows the proportion of tralokinumab/TCS-treated patients achieving target outcomes at week 12.

TABLE 10

| Outcome | Proportion of patients (%) treated with tralokinumab/TCS | Proportion of patients (%) in placebo/control group |
| --- | --- | --- |
| EASI-50 | 79 | 58.7 |
| ≥3 point reduction in worst daily pruritus | 59 | 42.1 |
| ≥4 point reduction in POEM | 78 | 56.1 |
| ≥4-point reduction in DLQI | 77 | 65.9 |
| ≥1-point reduction in PGI-B | 80.2 | 72.2 |

A high proportion of patients (79.4%; 196/247 assessed) achieved both a ≥1-point reduction in PGI-B and at least one of the other endpoints shown in Table 10.

At week 24, 81.0% (204/252) achieved EASI-50 (≥50% improvement of EASI) and 69.0% achieved EASI-75. For patients in the sub-group with both a ≥1-point reduction PGI-B and any of the other endpoints shown in Table 10 at 12 weeks (n=196), 90.8% achieved EASI-50 and 75.5% achieved EASI-75 at week 24.

The improvement in DLQI was maintained beyond week 16 in all treatment groups. The high level of maintained response with tralokinumab every other week or every 4 weeks was not associated with an increased use of TCS. The worst daily pruritus NRS scores decreased from 2.6 to 2.2 between weeks 16 and 32 in the tralokinumab plus TCS every other week group and from 3.0 to 2.7 in the tralokinumab plus TCS every 4 weeks group.

Figure 10A:
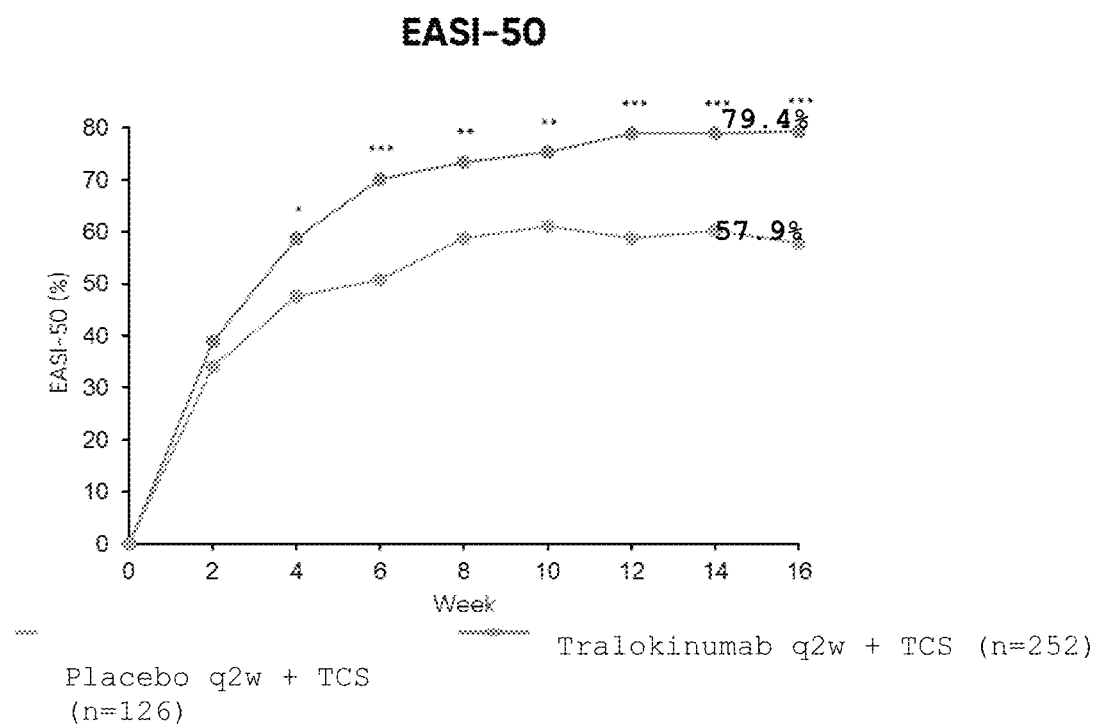
FIG. 10A. Achievement of EASI-50 following 16 weeks treatment with tralokinumab/TCS or placebo/TCS (control) (ECZTRA 3 trial). Patients with missing data imputed as nonresponders. *p<0.05 versus placebo+TCS; p<0.01 versus placebo+TCS; *p<0.001 versus placebo+TCS. EASI-50, at least 50% reduction in EASI score.
Figure 10B:
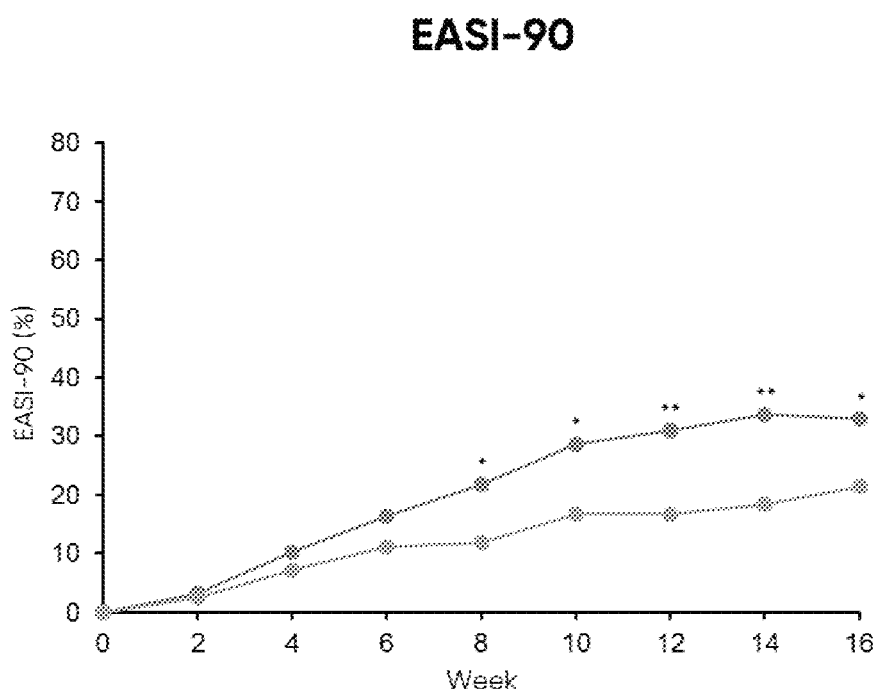
FIG. 10B. Achievement of EASI-90 following 16 weeks treatment with tralokinumab/TCS or placebo/TCS (control) (ECZTRA 3 trial). Patients with missing data imputed as nonresponders. *p<0.05 versus placebo+TCS; p<0.01 versus placebo+TCS; *p<0.001 versus placebo+TCS. EASI-90, at least 90% reduction in EASI score.
Figure 11A:
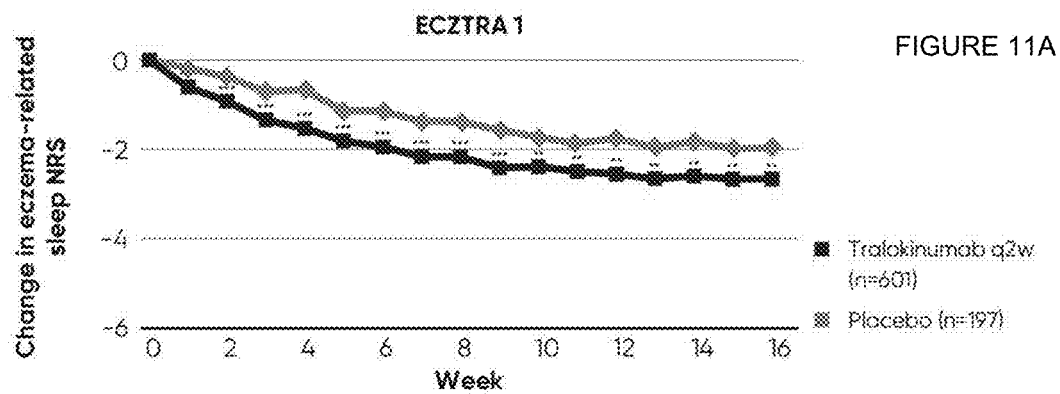
FIG. 11A. Eczema-Related Sleep Interference (ERSI) scores following 16 weeks of treatment in the ECZTRA 1 trials. *P<0.05;  P<0.01; P<0.001.
Figure 11B:
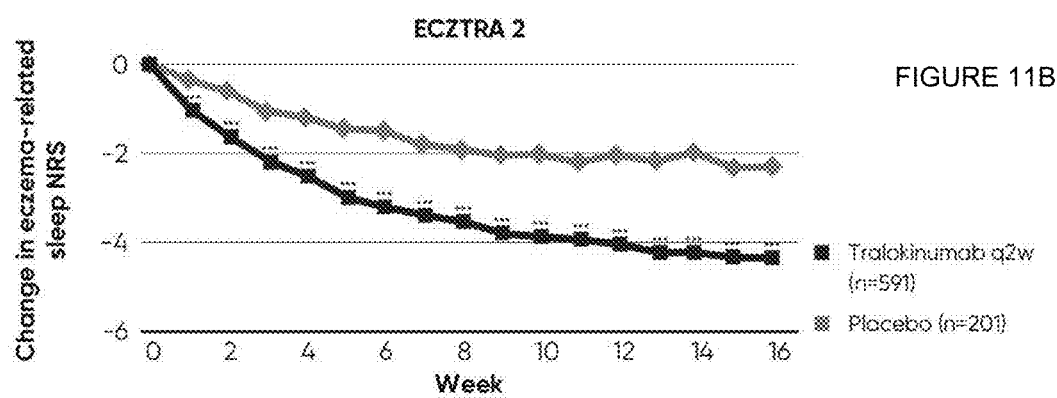
FIG. 11B. Eczema-Related Sleep Interference (ERSI) scores following 16 weeks of treatment in the ECZTRA 2 trials. *P<0.05;  P<0.01; P<0.001.
Figure 11C:
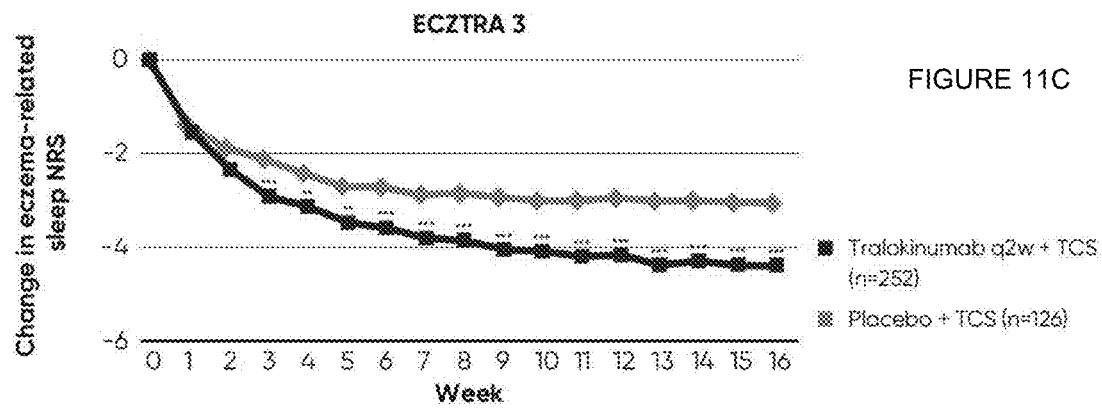
FIG. 11C. Eczema-Related Sleep Interference (ERSI) scores following 16 weeks of treatment in the ECZTRA 3 trials. *P<0.05;  P<0.01; P<0.001.
Figure 12A:
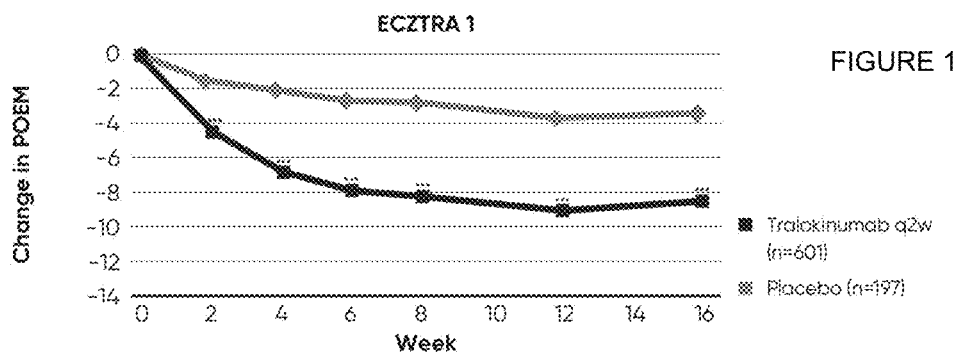
FIG. 12A. Patient-Oriented Eczema Measure (POEM) scores following 16 weeks of treatment in the ECZTRA 1 trials. *P<0.05;  P<0.01; P<0.001.
Figure 12B:
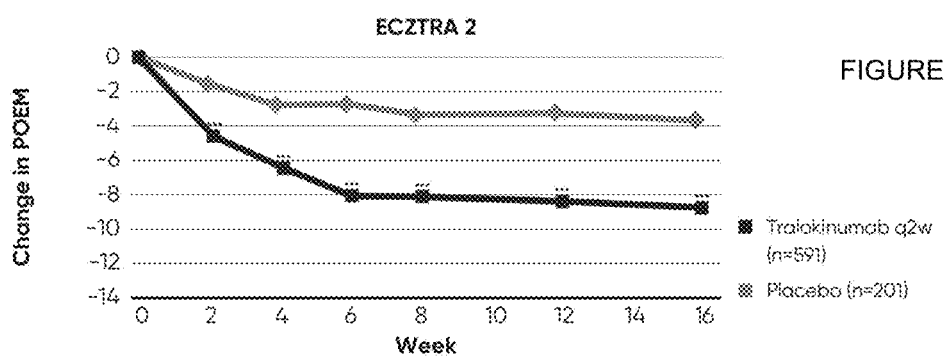
FIG. 12B. Patient-Oriented Eczema Measure (POEM) scores following 16 weeks of treatment in the ECZTRA 2 trials. *P<0.05;  P<0.01; P<0.001.
Figure 12C:
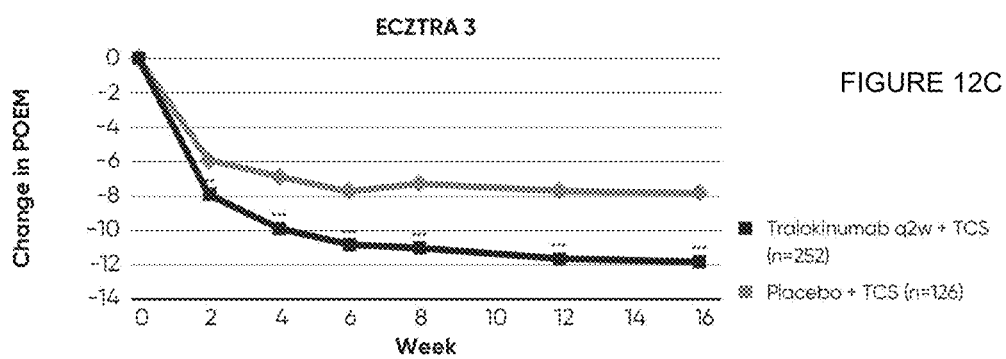
FIG. 12C. Patient-Oriented Eczema Measure (POEM) scores following 16 weeks of treatment in the ECZTRA 3 trials. *P<0.05;  P<0.01; P<0.001.
Figure 13A:
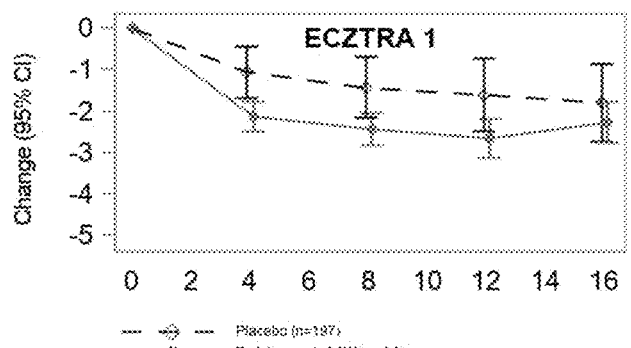
FIG. 13A. Adjusted mean change from baseline in HADS total score by Week for the ECZTRA 1 trials, initial treatment period: FAS.
Figure 13B:
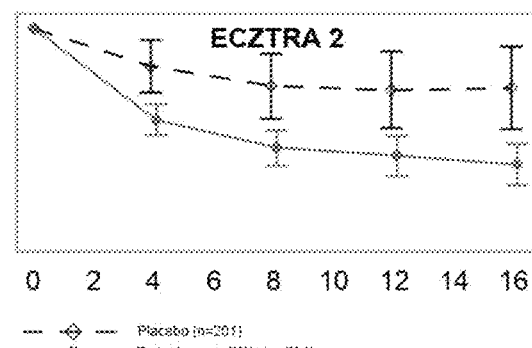
FIG. 13B. Adjusted mean change from baseline in HADS total score by Week for the ECZTRA 2 trials, initial treatment period: FAS.
Figure 13C:
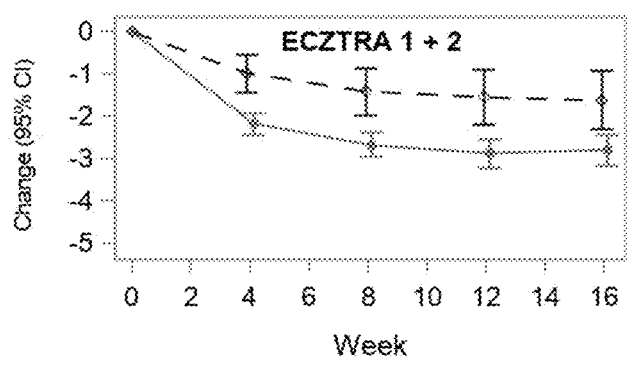
FIG. 13C. Adjusted mean change from baseline in HADS total score by Week for the ECZTRA 3 trials, initial treatment period: FAS.
Figure 13D:
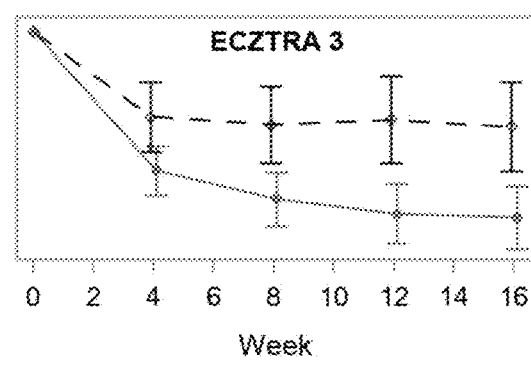
FIG. 13D. Adjusted mean change from baseline in HADS total score by Week for the ECZTRA 1+2 trials, initial treatment period: FAS.

As shown in FIGS. 10A-10B, more patients achieved EASI-50 and EASI-90 with tralokinumab/TCS versus placebo/TCS at week 16.

Conclusions

Tralokinumab/TCS combination therapy is associated with a high proportion of patients achieving and maintaining improvements in AD symptoms and AD-related quality of life after 3 and 6 months of treatment (typical follow up times in clinical practice). Tralokinumab combination therapy therefore provides a measurable benefit to patients at clinically relevant timepoints.

Example 4: Tralokinumab Monotherapy is Effective in Treating Moderate to Severe Atopic Dermatitis Two 52-week trials of tralokinumab monotherapy in moderate-to-severe AD (ECZTRA 1 and ECZTRA 2) were conducted to assess the efficacy of tralokinumab alone.

Methods

Patients were enrolled across Europe (ECZTRA 1: Germany, France and Spain; plus the UK, Italy, Poland and Russia in ECZTRA 2), North America (ECZTRA 1: USA; ECZTRA 2: USA and Canada), Asia (ECZTRA 1: Japan; ECZTRA 2: Korea), and Australia (ECZTRA 2) for two double-blind, randomized, placebo-controlled 52-week trials of tralokinumab monotherapy in moderate-to-severe AD. Inclusion criteria included: diagnosis of AD for >1 year, EASI score of ≥16 at baseline, IGA score of ≥3 at baseline, and an average pruritus NRS score of ≥4 prior at baseline.

Of 802 patients randomized in ECZTRA 1 and 794 patients randomized in ECZTRA 2, 50.7% and 48.7% had severe AD (IGA-4), respectively; mean EASIs were 32.4 and 32.2 at baseline. Although patients were enrolled into ECZTRA 1 and 2 had similar baseline disease characteristics, some baseline measures differed by region. For example, the proportion of patients with severe AD (IGA-4) was 50.7% (ECZTRA 1) and 48.7% (ECZTRA 2) for the overall study populations, while severe AD was higher in Japan (66.1%) and Australia (63.6%) as compared to Europe (52.6%/51.3%), North America (36.4%/43.2%) and Korea (43.6%). Of the patients with severe AD (IGA-4) at baseline, higher median baseline EASI scores were observed in Japan (46.6%) and Australia (47.2%), as compared to Europe (35.6%/41.2%), North America (35.3%/32.6%), and Korea (37.2%). These regional difference may explain the minor differences in therapeutic responses observed from ECZTRA 1 and ECZTRA 2.

Table 11 shows the demographic and clinical characteristics of randomized patients at baseline.

TABLE 11

| | ECZTRA 1 | | ECZTRA 2 | |
| --- | --- | --- | --- | --- |
| Characteristic | Placebo (N = 199) | Tralokinumab every other week (N = 603) | Placebo (N = 201) | Tralokinumab every other week (N = 593) |
| Median age, years (IQR) | 37.0 (26.0-49.0) | 37.0 (27.0-48.0) | 30.0 (23.0-46.0) | 34.0 (25.0-48.0) |
| Male, n (%) | 123 (61.8) | 351 (58.2) | 114 (56.7) | 359 (60.5) |
| Race, n (%) | | | | |
| White | 138 (69.3) | 426 (70.6) | 123 (61.2) | 374 (63.1) |
| Black | 18 (9.0) | 41 (6.8) | 17 (8.5) | 43 (7.3) |
| Asian | 40 (20.1) | 120 (19.9) | 52 (25.9) | 154 (26.0) |
| Other or missing data | 3 (1.5) | 16 (2.6) | 9 (4.5) | 22 (3.7) |
| Median disease duration, years (IQR) | 28.0 (18.0-41.0) | 27.0 (19.0-38.0) | 25.0 (18.0-36.0) | 25.5 (17.0-39.0) |
| Median affected body surface area, % (IQR) | 52.5 (31.0-77.0) | 50.0 (33.0-70.0) | 50.0 (31.0-74.0) | 50.0 (31.0-74.0) |
| Median EASI (IQR) | 30.3 (22.0-41.5) | 28.2 (21.3-40.0) | 29.6 (20.6-41.4) | 28.2 (19.8-40.8) |
| IGA 4, n (%) | 102 (51.3) | 305 (50.6) | 101 (50.2) | 286 (48.2) |
| Median total SCORAD (IQR) | 70.8 (63.8-81.0) | 69.2 (61.5-79.1) | 69.9 (61.9-79.1) | 69.5 (60.5-79.1) |
| Median weekly average of worst daily pruritus NRS (IQR) | 7.9 (6.9-8.7) | 7.9 (6.7-8.9) | 8.1 (7.1-9.0) | 8.0 (7.0-9.0) |
| Median DLQI (IQR) | 16.0 (13.0-22.0) | 17.0 (12.0-22.0) | 18.0 (12.5-24.0) | 18.0 (13.0-23.0) |

The studies comprised an initial 16-week treatment period and a 36-week maintenance treatment period. After a two-week washout period for TCS and other topical treatments, tralokinumab or placebo was given subcutaneously every other week for 16 weeks. Patients were randomized 3:1 and administered subcutaneous tralokinumab 300 mg or placebo every 2 weeks (Q2W) for 16 weeks. Primary endpoints were IGA-0/1 and EASI-75, achieved without the use of rescue medication.

Depending on their randomization scheme, patients received a loading dose of tralokinumab (600 mg) or placebo on day 0.

Patients were instructed to use a stable dose of an emollient applied twice daily or more as needed for 2 weeks before the baseline visit and throughout the trials. Rescue treatment for AD could be provided if medically necessary at the discretion of the investigator, to control intolerable symptoms, and did not prevent transfer to maintenance or open-label treatment. However, patients who received rescue treatment were considered non-responders in the primary analyses (see Statistical analysis below). Patients were to temporarily discontinue treatment if a systemic corticosteroid or nonsteroidal systemic immunosuppressive drug was used as rescue (see the Methods section in the online Supplementary Appendix for more detail); however, patients continued study treatment if rescue was limited to topical medication.

After the 16-week initial treatment period, tralokinumab-treated patients who achieved the pre-specified criteria for clinical response-defined as achievement of IGA 0 (clear) or 1 (almost clear), or 75% improvement in Eczema Area and Severity Index (EASI-75)—were transferred to the maintenance treatment phase and re-randomised 2:2:1 to receive tralokinumab 300 mg every other week or every 4 weeks, or placebo for an additional 36 weeks. Patients who achieved clinical response criteria with placebo continued to receive placebo every other week to maintain blinding of the study. The placebo cohort from week 16 was not randomised in the 36-week maintenance treatment period, and was not included in these analyses. Patients who did not achieve the clinical response criteria at week 16 were transferred to open-label tralokinumab 300 mg every other week with optional use of TCS. In addition, patients were transferred from maintenance treatment to open-label tralokinumab after week 16 if they failed to meet specified clinical response criteria over a 4-week period. All patients had a final safety follow-up 16 weeks after the last dose of study medication, unless transferred to the long-term ECZTEND trial (NCT03587805).

Patients were assessed every other week for clinical efficacy and safety measures, and laboratory measurements were taken every fourth week throughout the trials. Serum samples for determination of presence or absence of anti-drug antibodies (ADA) were collected at Weeks 0, 4, 16, 28, 52, and 66. Samples confirmed positive for ADA in the confirmatory step underwent ADA endpoint titre determination and were analysed for the presence of neutralising antibodies (nAB).

Results

Figure 3:
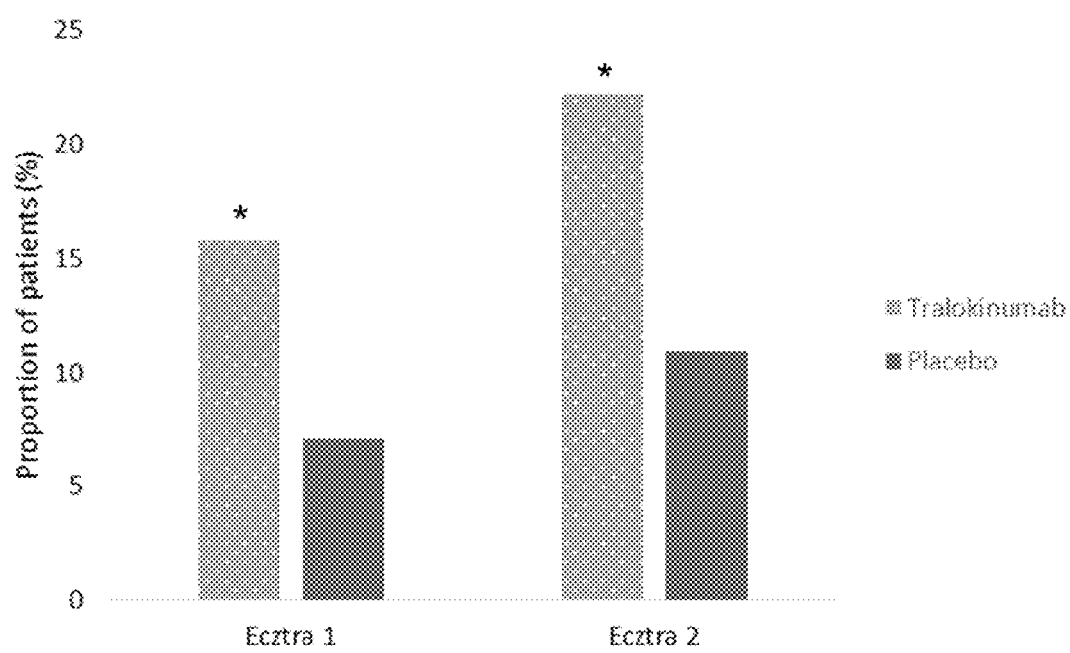
FIG. 3. Proportion of patients (%) achieving IGA-0/1 following 16 weeks of treatment with tralokinumab monotherapy or placebo (control) in two trials, ECZTRA 1 and ECZTRA 2. *=significant difference compared to control (p<0.05).
Figure 4:
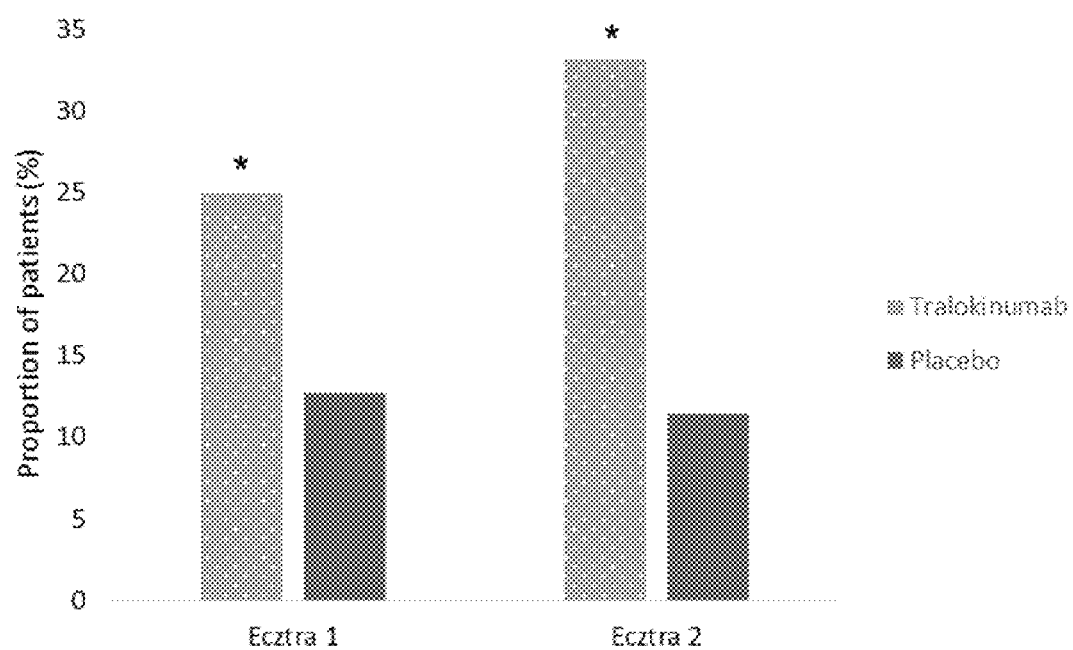
FIG. 4. Proportion of patients (%) achieving EASI-75 following 16 weeks of treatment with tralokinumab monotherapy or placebo (control) in two trials, ECZTRA 1 and ECZTRA 2. *=significant difference compared to control (p<0.05).

Tralokinumab Monotherapy Significantly Improved IGA and EASI Scores after 16 Weeks At week 16, IGA-0/1 responses were reported in significantly more patients treated with tralokinumab compared to the placebo control, in both ECZTRA 1 (15.8% tralokinumab compared to 7.1% placebo; p=0.002) and ECZTRA 2 (22.2% tralokinumab compared to 10.9% placebo; p<0.001) (see FIG. 3). EASI-75 responses were 25.0% for tralokinumab compared to 12.7% for placebo (ECZTRA 1) and 33.2% for tralokinumab compared to 11.4% for placebo (ECZTRA 2) (both p<0.001) (see FIG. 4).

The results of both primary and secondary outcomes at week 16 may be seen in Table 12 below:

TABLE 12

| | ECZTRA 1 | | ECZTRA 2 | |
|---|---|---|---|---|
| Outcome* | Placebo (N = 197) | Tralokinumab every other week (N = 601) | Placebo (N = 201) | Tralokinumab every other week (N = 591) |
| Primary endpoints§ | | | | |
| IGA of 0 or 1 at week 16, n (%)† | 14/197 (7.1) | 95/601 (15.8) | 22/201 (10.9) | 131/591 (22.2) |
| Difference versus placebo (95% CI) | | 8.6 (4.1, 13.1) P = 0.002 | | 11.1 (5.8, 16.4) P < 0.001 |
| EASI-75 at week 16, n (%)† | 25/197 (12.7) | 150/601 (25.0) | 23/201 (11.4) | 196/591 (33.2) |
| Difference versus placebo (95% CI) | | 12.1 (6.5, 17.7) P < 0.001 | | 21.6 (15.8, 27.3) P < 0.001 |
| EASI, LS mean % change from baseline (±SE) | −28.5 (±3.66) | −51.3§ (±1.92) | −22.2 (±3.48) | −56.6§ (±1.79) |
| Secondary endpoints | | | | |
| Adjusted mean change from baseline in SCORAD at week 16 | −14.7 (1.80) | −25.2 (0.94) | −14.0 (1.79) | −28.1 (0.92) |
| Difference versus placebo (95% CI) | | −10.4 (−14.4, −6.5) P < 0.001 | | −14.0 (−18.0, −10.1) P < 0.001 |

TABLE 12-continued

| Outcome* | ECZTRA 1 | | ECZTRA 2 | |
|---|---|---|---|---|
| | Placebo (N = 197) | Tralokinumab every other week (N = 601) | Placebo (N = 201) | Tralokinumab every other week (N = 591) |
| SCORAD, LS mean %-change from baseline (±SE$^c$) | −20.3 (2.72) | −36.7$^§$ (+ 1.42) | −20.6 (2.62) | −40.6$^§$ (1.34) |
| Improvement in worst daily pruritus NRS (weekly average) ≥4 points from baseline to week 16, n/N (%)$^{†,‡}$ | 20/194 (10.3) | 119/594 (20.0) | 19/200 (9.5) | 144/575 (25.0) |
| Difference versus placebo (95% CI) | | 9.7 (4.4, 15.0) P = 0.002 | | 15.6 (10.3, 20.9) P < 0.001 |
| Adjusted mean change from baseline in DLQI at week 16$^□$ | −5.0 (0.59) | −7.1 (0.31) | −4.9 (0.60) | −8.8 (0.30) |
| Difference versus placebo (95% CI) | | −2.1 (−3.4, −0.8) P = 0.002 | | −3.9 (−5.2, −2.6) P < 0.001 |
| Additional secondary endpoints | | | | |
| Adjusted mean change from baseline in worst daily pruritus NRS (weekly average) at week 16$^□$(SE) | −1.7 (0.21) | −2.6 (0.11) | −1.6 (0.21) | −2.9 (0.11) |
| Difference versus placebo (95% CI) | | −0.9 (−1.4, −0.4) P < 0.001 | | −1.3 (−1.7, −0.8) P < 0.001 |
| DLQI reduction ≥4 at week 16, n/N (%)$^†$ | 60/190 (31.6) | 258/578 (44.6) | 54/198 (27.3) | 325/577 (56.3) |
| Difference versus placebo (95% CI) | | 13.0 (5.4, 20.5) P = 0.001 | | 28.9 (21.4, 36.3) P < 0.001 |
| Adjusted mean change from baseline in EASI at week 16$^□$ | −9.0 (1.05) | −15.5 (0.55) | −7.0 (1.06) | −16.9 (0.55) |
| Difference versus placebo (95% CI) | | −6.4 (−8.8, −4.1) P < 0.001 | | −9.9 (−12.2, −7.5) P < 0.001 |
| EASI-50 at week 16, n (%)$^†$ | 42/197 (21.3) | 250/601 (41.6) | 41/201 (20.4) | 295/591 (49.9) |
| Difference versus placebo (95% CI) | | 20.1 (13.3, 26.8) P < 0.001 | | 29.3 (22.5, 36.1) P < 0.001 |
| EASI-90 at week 16, n (%)$^†$ | 8/197 (4.1) | 87/601 (14.5) | 11/201 (5.5) | 108/591 (18.3) |
| Difference versus placebo (95% CI) | | 10.3 (6.4, 14.1) P < 0.001 | | 12.7 (8.3, 17.0) P < 0.001 |
| Other endpoints | | | | |
| Worst daily pruritus NRS (weekly average) ≥3 at week 16, n/N (%)$^{†,§}$ | 28/195 (14.4) | 177/597 (29.6) | 28/200 (14.0) | 199/583 (34.1) |
| Difference versus placebo (95% CI) | | 15.2 (9.2, 21.3) P < 0.001 | | 20.1 (13.9, 26.2) P < 0.001 |
| Adjusted mean change from baseline in SCORAD at week 2 | −5.0 (0.92) | −10.6 (0.53) | −3.9 (0.84) | −10.8 (0.49) |
| Difference versus placebo (95% CI) | | −5.6 (−7.7, −3.5) P < 0.001 | | −6.9 (−8.8, −5.0) P < 0.001 |
| SCORAD 75 at week 16, n (%)$^†$ | 6/197 (3.0) | 53/601 (8.8) | 7/201 (3.5) | 68/591 (11.5) |

TABLE 12-continued

| Outcome* | ECZTRA 1 | | ECZTRA 2 | |
|---|---|---|---|---|
| | Placebo (N = 197) | Tralokinumab every other week (N = 601) | Placebo (N = 201) | Tralokinumab every other week (N = 591) |
| Difference versus placebo (95% CI) | | 5.7 (2.5, 8.9) $P = 0.007$ | | 8.0 (4.4, 11.6) $P < 0.001$ |
| SCORAD 50 at week 16, n (%)† | 23/197 (11.7) | 156/601 (26.0) | 29/201 (14.4) | 198/591 (33.5) |
| Difference versus placebo (95% CI) | | 14.1 (8.6, 19.6) $P < 0.001$ | | 18.9 (12.8, 25.1) $P < 0.001$ |
| Adjusted mean change (SE) from baseline in worst daily pruritus NRS (weekly average) at week 1□ | −0.2 (0.07) | −0.7 (0.04) | 0.3 (0.08) | −0.7 (0.05) |
| Difference versus placebo (95% CI) | | −0.4 (−0.6, −0.3) $P < 0.001$ | | −0.4 (−0.6, −0.2) $P < 0.001$ |
| Adjusted mean change from baseline in DLQI at week 2□ | −2.5 (0.39) | −4.4 (0.22) | −2.2 (0.39) | −4.7 (0.23) |
| Difference versus placebo (95% CI) | | −2.0 (−2.8, −1.1) $P < 0.001$ | | −2.5 (−3.4, −1.7) $P < 0.001$ |

*Treatment comparisons with Cochran-Mantel-Haenszel test, stratified by region and baseline IGA;
†Subjects who received rescue medication considered non-responders. Subjects with missing data at Week 16 imputed as non-responders;
‡Based on patients in FAS with a baseline pruritus NRS weekly average of at least 4;
§Based on patients in FAS with a baseline pruritus NRS weekly average of at least 3;
□Data collected after permanent discontinuation of IMP or initiation of rescue medication not included. Repeated measurements model on post-baseline data: Change in measure = Treatment*Week + (Baseline measure)*Week + Region + Baseline IGA.

Tralokinumab Monotherapy Maintained IGA and EAST Scores after 52 Weeks

In ECZTRA 1 and ECZTRA 2, respectively, 185 and 227 patients were re-randomised after the initial 16-week treatment period 2:2:1 to continue treatment with tralokinumab every other week, reduce the dosing frequency of tralokinumab to every 4 weeks, or switch to placebo every 2 weeks.

The IGA and EASI 75 results may be in Table 13 below:

TABLE 13

| | Outcome | | | | | |
|---|---|---|---|---|---|---|
| | ECZTRA 1 | | | ECZTRA 2 | | |
| | Placebo (N = 35) | Tralokinumab every other week (N = 68) | Tralokinumab every 4 weeks (N = 76) | Placebo (N = 46) | Tralokinumab every other week (N = 91) | Tralokinumab every 4 weeks (N = 89) |
| IGA of 0/1 at week 52, n/N (%)* | 9/19 (47.4) | 20/39 (51.3) | 14/36 (38.9) | 7/28 (25.0) | 32/54 (59.3) | 22/49 (44.9) |
| Difference in percentage versus placebo (95% CI) | | 6.0 (−21.8, 33.7) $P = 0.68$ | −9.5 (−37.1, 18.0) $P = 0.50$ | | 34.1 (13.4, 54.9) $P = 0.004$ | 19.9 (−1.2, 40.9) $P = 0.084$ |
| EASI-75 at week 52, n/N (%)† | 10/30 (33.3) | 28/47 (59.6) | 28/57 (49.1) | 9/42 (21.4) | 43/77 (55.8) | 38/74 (51.4) |
| Difference in percentage versus placebo (95% CI) | | 21.2 (−0.2, 42.6) $P = 0.056$ | 11.7 (−8.7, 32.0) $P = 0.97$ | | 33.7 (17.3, 50.0) $P < 0.001$ | 30.0 (13.7, 46.4) $P = 0.001$ |

*Among patients with IGA of 0/1 at week 16 achieved without rescue medication after initial randomization to tralokinumab;
†Among patients with EASI-75 at week 16 achieved without rescue medication after initial randomization to tralokinumab.
EASI, Eczema Area and Severity Index;
IGA, Investigator's Global Assessment.

At week 52, 51.3% (ECZTRA 1) and 59.3% (ECZTRA 2) of patients maintained IGA-0/1 with tralokinumab Q2W. Q4W responses were similar, with 38.9% (ECZTRA 1) and 44.9% (ECZTRA 2) of patients maintaining IGA-0/1. The results are shown in FIGS. 7A-D. In patients who were re-randomised to placebo, 47.4% and 25.0% maintained response at week 52 in ECZTRA 1 and ECZTRA 2, respectively. There was no statistically significant difference in the proportion of patients maintaining an IGA 0/1 response at week 52 between patients continuing tralokinumab every other week and those who were initially treated with tralokinumab and switched to placebo at week 16 in ECZTRA 1. In ECZTRA 2, the difference in the proportion of patients maintaining IGA 0/1 at week 52 with tralokinumab every other week was significant compared to placebo; however, there was no statistically significant difference in IGA 0/1 response between tralokinumab every 4 weeks and placebo (P=0.084.

In ECZTRA 1 and ECZTRA 2, respectively, the proportion of patients who maintained EASI-75 at week 52, among patients achieving EASI-75 at week 16 on tralokinumab without rescue medication was 59.6% and 55.8% in patients who continued with tralokinumab every other week, 49.1% and 51.4% in patients who were re-randomised to tralokinumab every 4 weeks, and 33.3% and 21.4% in patients who were re-randomised to placebo.

Of the subjects randomised to tralokinumab, who did not achieve IGA 0 or 1 or EASI-75 at week 16 and were transferred to open-label Tralokinumab 300 mg Q2W+ optional TCS, 20.8% in ECZTRA 1 and 19.3% in ECZTRA 2 achieved IGA 0 or 1 at week 52, and 46.1% in ECZTRA 1 and 39.3% in ECZTRA 2 achieved EASI-75 at week 52. The clinical response was mainly driven by continued tralokinumab treatment rather than optional TCS treatment. A higher proportion of subjects with IGA 2 or EASI-50 at week 16 achieved IGA 0 or 1 or EASI-75 at week 52 compared to subjects with IGA 3 or 4 or <EASI-50 at week 16.

In both studies, treatment with tralokinumab resulted in greater EASI-50 and EASI-90 responses than placebo at week 16, and a greater percent change in EASI score at week 16, with a separation between treatment arms (P<0.05) occurring from week 2 onward.

The proportion of patients achieving EASI-50 was greater with tralokinumab compared with placebo at each scheduled assessment in the initial treatment period, with a separation between treatment groups occurring from week 2. EASI-90 was achieved by more patients treated with tralokinumab than those who received placebo from week 4 to week 16, with a separation between treatment groups from week 6 onward. The percentage change from baseline in EASI score was greater with tralokinumab compared with placebo at each assessment including week 16 in both trials, with a separation between treatment groups (P<0.05) occurring from week 2 onward.

Tralokinumab Monotherapy has a Favorable Safety Profile Over 52 Weeks

Adverse events (AEs) were similar between tralokinumab Q2W and placebo over 16 weeks; and the adverse-event profile over 52 weeks was comparable to the initial 16 weeks.

The incidence of AEs was comparable between tralokinumab and placebo in the initial treatment period of both studies. The majority of AEs were non-serious and mild or moderate in severity, with most resolved or resolving by the end of the treatment period, and few patients had AEs leading to permanent discontinuation of the investigational medicinal product (IMP). The most frequent AEs in the initial treatment period were worsening of AD and upper respiratory tract infections (mainly reported as common cold).

There was a low and comparable frequency of serious adverse events (SAEs) in both treatment groups in the initial treatment period of both studies. The majority of patients reporting SAEs recovered from the events. No marked differences in SAEs were observed between the treatment groups within each treatment period and between the treatment periods, and there was no clustering with respect to specific system organ class or event types.

Conjunctivitis—reported as part of standard AE reporting and as an AE of special interest—occurred with greater frequency in patients treated with tralokinumab than in those who received placebo. Most cases of conjunctivitis were mild and resolved by the end of the treatment period; one case led to treatment withdrawal. Tralokinumab was associated with lower rates of eczema herpeticum (0.5% tralokinumab vs 1.0% placebo in ECZTRA 1, and 0.3% tralokinumab vs 2.5% placebo in ECZTRA 2.

Skin infections requiring systemic treatment reported as an AE of special interest occurred more frequently in patients who received placebo than those who were treated with tralokinumab in ECZTRA 2; in ECZTRA 1, the frequencies were similar between the two groups. In ECZTRA 1, the reduction in *Staphylococcus aureus* colonisation on lesional skin, from baseline to week 16, as assessed by qPCR, was more than 10 times greater for tralokinumab-treated patients compared to those who received placebo: median 969 to 22 gene copies/cm$^2$ with tralokinumab compared with 649 to 238 gene copies/cm$^2$ with placebo.

Overall, in the maintenance treatment period, AEs were reported at a lower rate compared with tralokinumab every other week in the initial treatment period and the pattern of events was comparable to that in the initial treatment period. AEs were more frequently reported in the tralokinumab every other week group than in the tralokinumab every 4 weeks group. In total, 4 patients experienced SAEs in ECZTRA 1 (1 who received tralokinumab every other week and 3 who received tralokinumab every 4 weeks) and 3 patients had SAEs in ECZTRA 2, all in the tralokinumab every 4 weeks group. Two and three patients had AEs leading to permanent discontinuation of tralokinumab in ECZTRA 1 and ECZTRA 2, respectively.

A positive broad neutralising antibody (nAB) response was observed for 3 patients treated with tralokinumab in ECZTRA 1, and in 8 patients treated with tralokinumab in ECZTRA 2. Based on examination of tralokinumab concentrations, ADA responses, AEs, and IGA/EASI scores across the trials, it was considered that the presence of nAB did not have an impact on the efficacy and safety of tralokinumab for any of the subjects There were no noteworthy differences between treatment groups in laboratory values, vital signs, or electrocardiograments. More subjects treated with tralokinumab experienced eosinophilia during the initial treatment period but the mean eosinophil levels returned to baseline values during the maintenance period, and the safety profile of subjects with eosinophilia (>1.5×10$^9$L) was comparable to that in the total trial population. Table 14 shows that the overall frequency and severity of adverse effects over 16 weeks.

Summary of AEs and AESIs in the 16 Week Initial Treatment Period

TABLE 14

|  | ECZTRA 1 | | ECZTRA 2 | |
| --- | --- | --- | --- | --- |
|  | Placebo (N = 196) | Tralokinumab every other week (N = 602) | Placebo (N = 200) | Tralokinumab every other week (N = 592) |
| Adverse events | | | | |
| Total number of adverse events | 491 | 1482 | 408 | 997 |
| Total number of serious adverse events | 11 | 24 | 6 | 10 |
| Patients with adverse events | | | | |
| ≥1 adverse event | 151 (77.0) | 460 (76.4) | 132 (66.0) | 364 (61.5) |
| ≥1 serious adverse event | 8 (4.1) | 23 (3.8) | 5 (2.5) | 10 (1.7) |
| Severity | | | | |
| Mild | 111 (56.6) | 385 (64.0) | 93 (46.5) | 288 (48.6) |
| Moderate | 98 (50.0) | 241 (40.0) | 84 (42.0) | 168 (28.4) |
| Severe | 16 (8.2) | 41 (6.8) | 16 (8.0) | 24 (4.1) |
| Leading to permanent discontinuation of IMP | 8 (4.1) | 20 (3.3) | 3 (1.5) | 9 (1.5) |
| Not recovered/not resolved | 35 (17.9) | 106 (17.6) | 25 (12.5) | 61 (10.3) |
| Recovering/resolving | 7 (3.6) | 36 (6.0) | 15 (7.5) | 20 (3.4) |
| Recovered/resolved | 139 (70.9) | 429 (71.3) | 125 (62.5) | 340 (57.4) |
| Recovered/resolved with sequelae | 0 | 6 (1.0) | 2 (1.0) | 9 (1.5) |
| Frequent AEs (≥5% in any treatment group), n (%)* | | | | |
| Atopic dermatitis | 75 (38.3) | 156 (25.9) | 67 (33.5) | 98 (16.6) |
| Viral upper respiratory tract infection | 41 (20.9) | 139 (23.1) | 17 (8.5) | 49 (8.3) |
| Upper respiratory tract infection | 2 (1.0) | 9 (1.5) | 17 (8.5) | 59 (10.0) |
| Conjunctivitis† | 4 (2.0) | 43 (7.1) | 3 (1.5) | 18 (3.0) |
| Skin infection | 3 (1.5) | 6 (1.0) | 11 (5.5) | 12 (2.0) |
| Pruritus | 10 (5.1) | 32 (5.3) | 5 (2.5) | 12 (2.0) |
| Headache | 10 (5.1) | 28 (4.7) | 6 (3.0) | 16 (2.7) |
| AESIs - eye disorders | 7 (3.6) | 62 (10.3) | 6 (3.0) | 33 (5.6) |
| Conjunctivitis† | 7 (3.6) | 60 (10.0) | 5 (2.5) | 31 (5.2) |
| Keratoconjunctivitis | 0 | 1 (0.2) | 0 | 2 (0.3) |
| Keratitis | 0 | 3 (0.5) | 1 (0.5) | 1 (0.2) |
| AESIs - skin infections requiring systemic treatment | 4 (2.0) | 13 (2.2) | 22 (11) | 21 (3.5) |
| AESIs - eczema herpeticum | 2 (1.0) | 3 (0.5) | 5 (2.5) | 2 (0.3) |
| AESIs - malignancies diagnosed after randomization | 0 | 0 | 0 | 1 (0.2) |

*Reporting adverse events at the level of PTs according to MedDRA 20.0 occurring in at least 5% of patients in any randomised group;
†PTs according to MedDRA 20.0 include conjunctivitis, conjunctivitis allergic and conjunctivitis viral Table 15 shows that the overall frequency and severity of adverse effects during the 36-week maintenance period.

| | Event | | | | | |
|---|---|---|---|---|---|---|
| | ECZTRA 1 | | | ECZTRA 2 | | |
| | Placebo (N = 35) | Tralokinumab Every Other Week (N = 68) | Tralokinumab Every Four weeks (N = 76) | Placebo (N = 46) | Tralokinumab Every Other Week (N = 91) | Tralokinumab Every Four weeks (N = 89) |
| Adverse or serious adverse event - no. (%) | | | | | | |
| At least 1 adverse event | 25 (71.4) | 54 (79.4) | 53 (69.7) | 32 (69.6) | 62 (68.1) | 56 (62.9) |
| At least 1 serious adverse event | 0 | 1 (1.5) | 3 (3.9) | 0 | 0 | 3 (3.4) |
| Adverse event leading to withdrawal from trial | 0 | 1 (1.5) | 1 (1.3) | 0 | 2 (2.2) | 1 (1.1) |
| Adverse events (≥5% in any treatment group) - no. (%)* Infections and infestations | | | | | | |
| Viral upper respiratory tract infection | 4 (11.4) | 14 (20.6) | 18 (23.7) | 7 (15.2) | 9 (9.9) | 6 (6.7) |
| Upper respiratory tract infection | 1 (2.9) | 1 (1.5) | 2 (2.6) | 3 (6.5) | 14 (15.4) | 9 (10.1) |
| Bronchitis | 2 (5.7) | 3 (4.4) | 7 (9.2) | 0 | 1 (1.1) | 3 (3.4) |
| Influenza | 1 (2.9) | 4 (5.9) | 3 (3.9) | 1 (2.2) | 2 (2.2) | 1 (1.1) |
| Nasopharyngitis | 2 (5.7) | 0 | 3 (3.9) | 0 | 3 (3.3) | 2 (2.2) |
| Conjunctivitis | 0 | 3 (4.4) | 4 (5.3) | 2 (4.3) | 5 (5.5) | 1 (1.1) |
| Other AEs | | | | | | |
| Atopic dermatitis | 13 (37.1) | 11 (16.2) | 14 (18.4) | 9 (19.6) | 13 (14.3) | 14 (15.7) |
| Injection site reaction | 1 (2.9) | 5 (7.4) | 7 (9.2) | 0 | 4 (4.4) | 4 (4.5) |
| Headache | 3 (8.6) | 6 (8.8) | 2 (2.6) | 0 | 2 (2.2) | 2 (2.2) |
| Asthma | 0 | 4 (5.9) | 1 (1.3) | 3 (6.5) | 2 (2.2) | 3 (3.4) |
| Dry eye | 0 | 0 | 0 | 3 (6.5) | 1 (1.1) | 0 |
| Hypertension | 0 | 1 (1.5) | 2 (2.6) | 3 (6.5) | 1 (1.1) | 1 (1.1) |
| Allergic conjunctivitis | 2 (5.7) | 3 (4.4) | 1 (1.3) | 1 (2.2) | 2 (2.2) | 3 (3.4) |
| Liver function test increased/abnormal | 2 (5.7) | 0 | 0 | 0 | 1 (1.1) | 1 (1.1) |
| Oropharyngeal pain | 2 (5.7) | 1 (1.5) | 0 | 0 | 1 (1.1) | 2 (2.2) |
| Back pain | 0 | 3 (4.4) | 4 (5.3) | 0 | 3 (3.3) | 2 (2.2) |
| Pruritus | 1 (2.9) | 2 (2.9) | 4 (5.3) | 2 (4.3) | 2 (2.2) | 2 (2.2) |

The incidence of eye disorders was collected as adverse events of special interest due to the increased incidence of eye disorders observed in clinical trials of dupilumab. Conjunctivitis occurred in less than 8% of patients receiving tralokinumab in either study in the initial treatment period and in less than 6% in any tralokinumab treatment arm in the maintenance periods. Almost all cases of conjunctivitis were mild/moderate and 1 case led to withdrawal.

Conclusion

Both trials show that tralokinumab monotherapy significantly improved IGA and EASI scores in patients with moderate-to-severe AD after 16 weeks, with a favorable safety profile. Tralokinumab monotherapy maintained efficacy over 52 weeks in responders when the dosing frequency was 2 weeks and, surprisingly, a similar response was also maintained at a dosing frequency of 4 weeks.

Example 5: Tralokinumab Monotherapy Improves Patient Reported Outcomes

As discussed above, AD is a disease with a substantial patient burden, with symptoms including pain, itching, and sleep disturbance. The effect of tralokinumab monotherapy on patient-reported outcomes (PROs) were evaluated in phase 3 trials (ECZTRA 1, NCT03131648; ECZTRA 2, NCT03160885).

Methods

PROs were analysed for patients in the ECZTRA 1 and 2 trials described in Example 4. Assessed PROs included ≥4-point reduction in worst daily pruritus Numerical Rating Scale (NRS); reduction in eczema-related sleep interference; Patient-Oriented Eczema Measure (POEM), SCORAD and change in Dermatology Life Quality Index (DLQI) scores.

The baseline eczema-related sleep interference scores were 6.3 (ECZTRA 1) and 6.9 (ECZTRA 2). The baseline mean POEM score was 22.8 for both ECZTRA 1 and ECZTRA 2. Baseline mean DLQI values were 16.8 (ECZTRA 1) and 17.7 (ECZTRA 2). The baseline worst daily pruritus scores were 7.7 (ECZTRA 1) and 7.9 (ECZTRA 2).

Results

In both studies, there were significant differences between the tralokinumab and placebo groups with regard to all secondary endpoints in example 4.

Results for other endpoints may be seen in Table 16 below.

TABLE 16

| | Monotherapy | | | |
|---|---|---|---|---|
| | ECZTRA 1 week 16 | | ECZTRA 2 week 16 | |
| | Placebo | TRADENAME 300 mg Q2 W | Placebo | TRADENAME 300 mg Q2 W |
| Patients randomised | 199 | 603 | 201 | 593 |
| Eczema-related sleep NRS, LS mean change from baseline (SE)[a)] | −1.9 (0.2) | −2.6[#] (0.1) | −1.5 (0.2) | −2.9[§] (0.1) |
| POEM, LS mean change from baseline (SE)[a)] | −3.0 (0.66) | −7.6[§] (0.35) | −3.7 (0.66) | −8.8[§] (0.33) |
| POEM (≥4-point improvement), responders[b)] | 18.0% (35/194) | 43.0%[§] (253/588) | 22.1% (44/199) | 54.4%[§] (319/586) |

LS: Least squares, SE: Standard error. If needed to control intolerable symptoms of atopic dermatitis, patients were permitted to receive rescue treatment at the discretion of the investigator.
[a)]Data after initiation of rescue medication or permanent discontinuation of treatment was excluded from the analyses.
[b)]Subjects who received rescue treatment or had missing data were treated as non-responders. The percentage is calculated relative to the number of subjects with POEM ≥4 at baseline
*p < 0.05,
p < 0.01,
§p < 0.001.

Figure 8A:
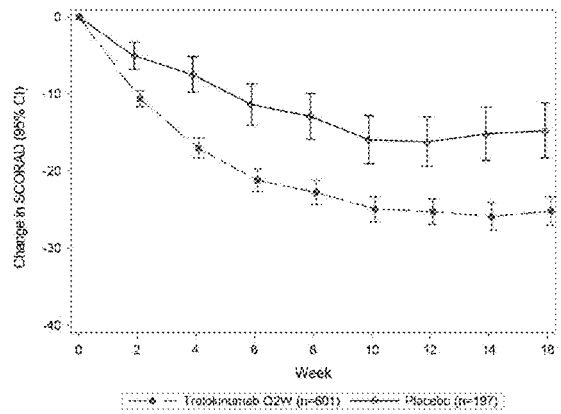
FIG. 8A. Scores for secondary endpoints (SCORAD) at baseline and following 16 weeks treatment with tralokinumab or placebo (control) in ECZTRA 1 trials. SCORAD=Scoring atopic dermatitis.
Figure 8B:
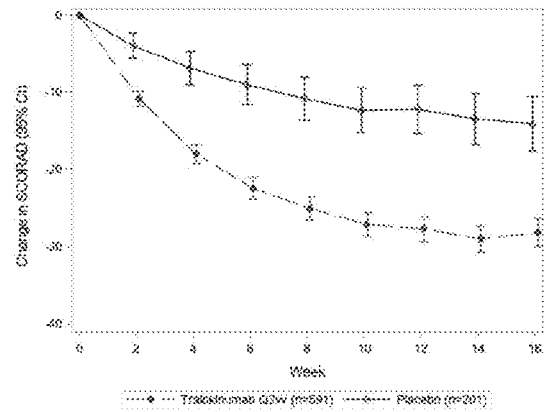
FIG. 8B. Scores for secondary endpoints (SCORAD) at baseline and following 16 weeks treatment with tralokinumab or placebo (control) in ECZTRA 2 trials.

A significantly greater reduction in SCORAD was achieved in the tralokinumab group, compared with the placebo group at week 16 (P<0.001 vs placebo in both trials). The change from baseline in SCORAD was greater with tralokinumab compared with placebo throughout the initial treatment period, and a separation between the treatment groups (P<0.001) was observed from week 2 onward (FIGS. 8A-8B). The change from baseline in SCORAD sleep score was greater with tralokinumab vs PBO at each week, with a separation between treatment groups (p<0.01) from week 2.

Figure 8C:
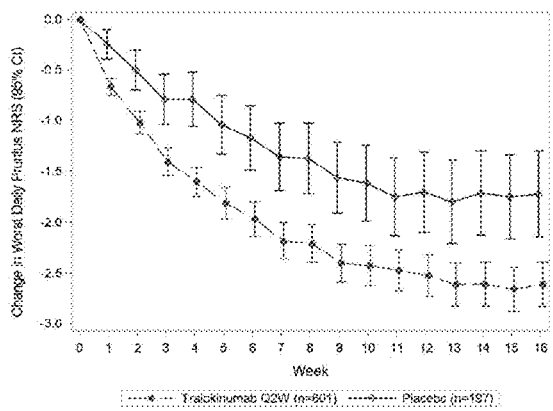
FIG. 8C. Scores for secondary endpoints (pruritus) at baseline and following 16 weeks treatment with tralokinumab or placebo (control) in ECZTRA 1 trials.
Figure 8D:
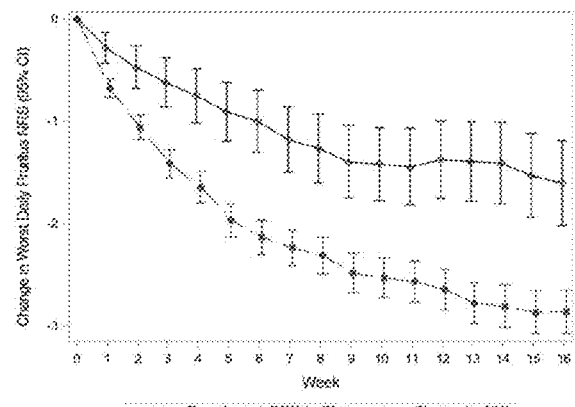
FIG. 8D. Scores for secondary endpoints (pruritus) at baseline and following 16 weeks treatment with tralokinumab or placebo (control) in ECZTRA 2 trials.
Figure 8E:
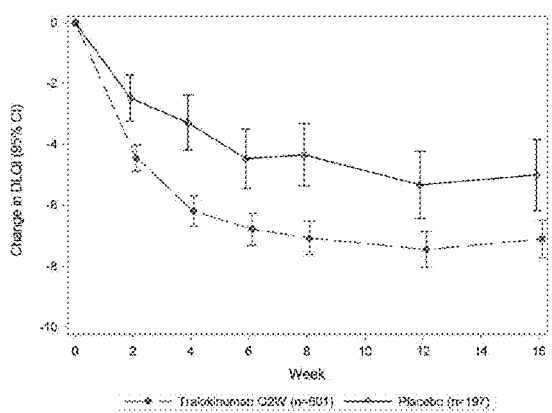
FIG. 8E. Scores for secondary endpoints (DLQI) at baseline and following 16 weeks treatment with tralokinumab or placebo (control) in ECZTRA 1 trials. DLQI=Dermatology Life Quality Index.
Figure 8F:
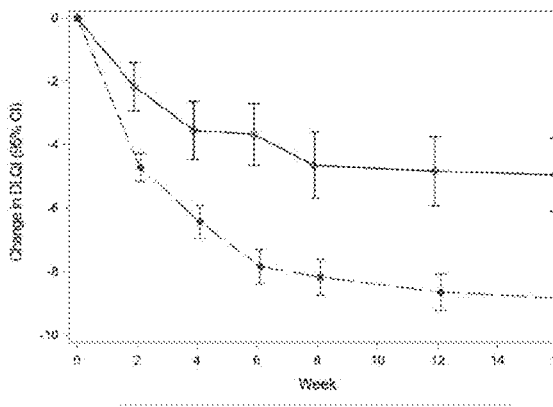
FIG. 8F. Scores for secondary endpoints (DLQI) at baseline and following 16 weeks treatment with tralokinumab or placebo (control) in ECZTRA 2 trials.

A significantly greater proportion of patients achieved a reduction of worst daily pruritus NRS (weekly average) of ≥4 with tralokinumab (20% and 25%) compared with placebo (10.3% and 9.5%) at week 16 in ECZTRA 1 (P=0.002) and ECZTRA 2 (P<0.001), respectively. The reduction in worst daily pruritus NRS (weekly average) was greater with tralokinumab compared with placebo throughout the initial treatment period, with a separation between the treatment groups (P<0.05) observed from week 1 onward (FIGS. 8C-8D). By week 3, the proportion of patients with a ≥4-point reduction in worst daily pruritus from baseline (7.7/7.9) was significantly higher with tralokinumab compared to placebo in ECZTRA 1 (8.1% compared to 1.5%; p<0.001) and ECZTRA 2 (7.5% compared to 3.0%; p=0.021).

Eczema-related sleep NRS (weekly average) improved in both treatment groups in both studies, ECZTRA 1 and 2. The adjusted mean change (standard error [SE]) from baseline at week 16 was greater with tralokinumab vs Placebo: −2.6 (0.12) vs −1.9 (0.23); p=0.007 in ECZTRA 1 and −2.9 (0.12) vs −1.5 (0.22); p<0.001 in ECZTRA 2.

Change from baseline in eczema-related sleep NRS was larger with tralokinumab vs placebo at each week, with a separation between-treatment groups (p<0.001) from week 1.

By week 2 in both trials there was a decreased score in eczema-related sleep interference in tralokinumab-treated patients, which was significantly different from the control groups. In ECZTRA 1 tralokinumab-treatment decreased eczema-related sleep interference by 0.9 compared to a decrease of 0.4 in the control group (p<0.001). Eczema-related sleep interference changes in the ECZTRA 2 trial were −1.1 for tralokinumab compared to −0.4 for control (p<0.001).

SCORAD sleep score improved in both treatment groups in both studies. The adjusted mean change (SE) from baseline at week 16 was greater with tralokinumab vs placebo: −2.6 (0.14) vs −1.8 (0.26); p=0.004 in ECZTRA 1 and −3.0 (0.14) vs −1.8 (0.28); p<0.001 in ECZTRA 2, with separation between groups from week 2.

Figure 14A:
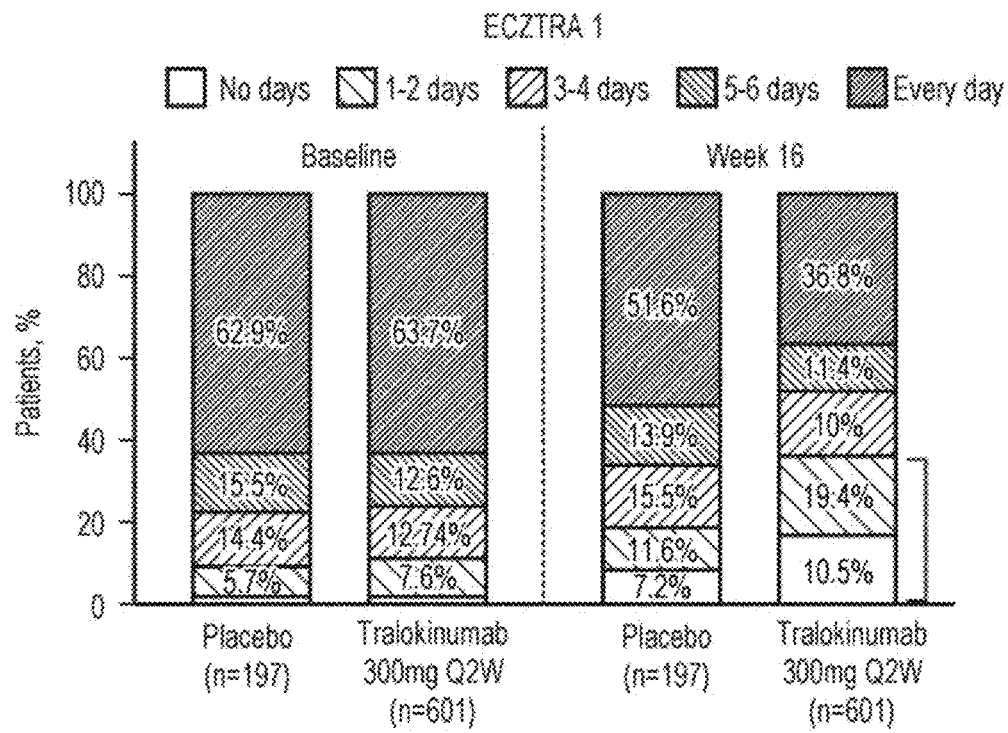
FIG. 14A. Proportion of patients in the ECZTRA1 trials reporting sleep interference no days, 1-2 days, 3-4 days, 5-6 days or every day.
Figure 14B:
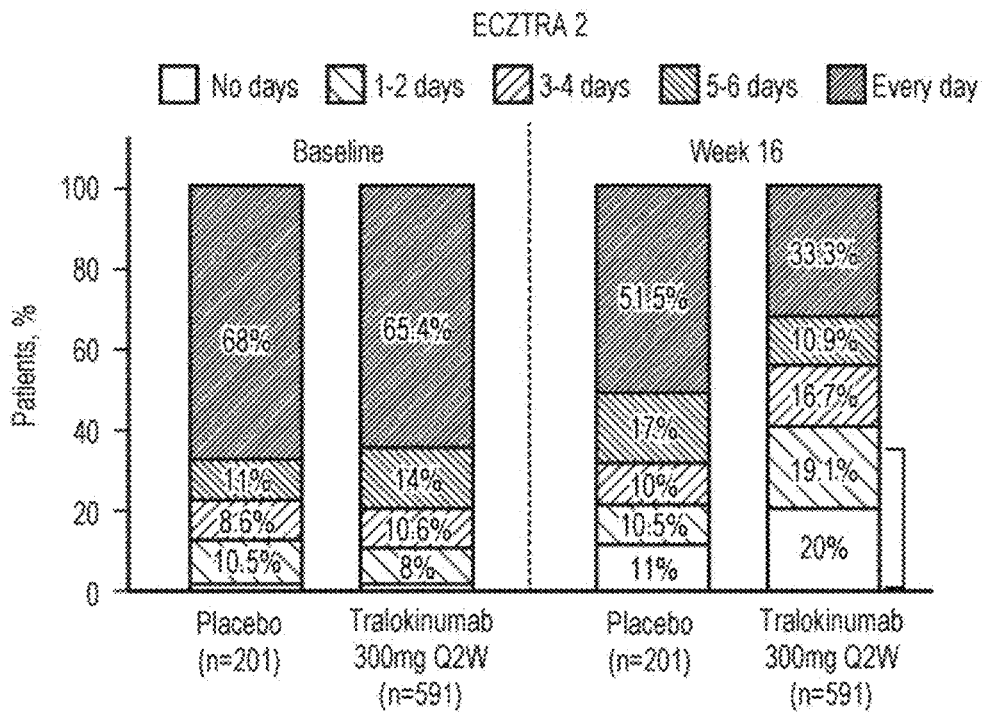
FIG. 14B. Proportion of patients in the ECZTRA2 trials reporting sleep interference no days, 1-2 days, 3-4 days, 5-6 days or every day.

POEM sleep score improved to a greater extent with tralokinumab compared with PBO from week 2 onwards (p<0.001) and the adjusted mean change (SE) from baseline to week 16 was greater with tralokinumab vs PBO: −1.2 (0.07) vs −0.6 (0.13) in ECZTRA 1 and −1.3 (0.07) vs −0.6 (0.13) in ECZTRA 2 (both p<0.001). A greater proportion of tralokinumab treated patients (35.9-39.1%) reported "No day" or "1-2 days" of sleep interference at week 16 vs placebo (see FIGS. 14A-14B).

Change from baseline in DLQI was greater with tralokinumab than with placebo in ECZTRA 1 (−7.1 vs −5.0; P=0.02) and ECZTRA 2 (−8.8 vs −4.9; P<0.001) at week 16, and at each scheduled assessment throughout the initial treatment period, with a separation between treatment arms (P<0.05) from week 2 onwards.

By week 2 in both trials there was a decreased score in POEM and DLQI in tralokinumab treated patients, which was significantly different from the placebo:

DLQI was decreased by 4.4 for tralokinumab compared to 2.5 for control (p<0.001) in ECZTRA 1, and decreased by 4.7 for tralokinumab compared to 2.2 for control (p<0.001) in ECZTRA 2. Mean improvements from baseline for DLQI reached the minimal clinical important difference (MCID) in addition to statistical significance.

Mean POEM was significantly reduced from baseline relative to placebo in ECZTRA 1 (−4.0 for tralokinumab compared to −1.3 for control; p<0.001) and ECZTRA 2 (−4.6 for tralokinumab compared to −1.6 for control; p<0.001). Mean improvements from baseline for POEM reached the minimal clinical important difference (MCID) in addition to statistical significance.

Figure 8G:
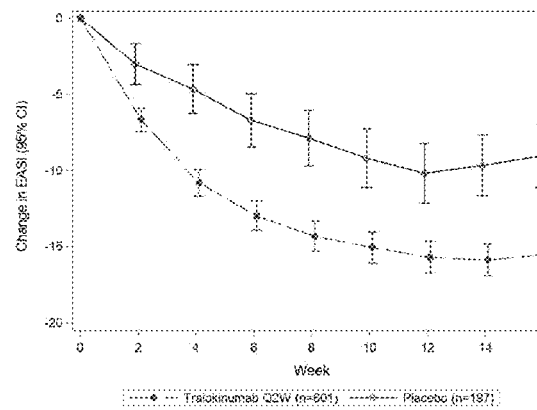
FIG. 8G. Scores for secondary endpoints (EASI) at baseline and following 16 weeks treatment with tralokinumab or placebo (control) in ECZTRA 1 trials. EASI=Eczema Area and Severity Index.
Figure 8H:
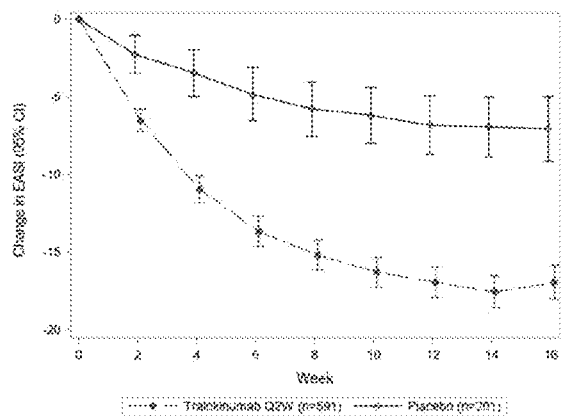
FIG. 8H. Scores for secondary endpoints (EASI) at baseline and following 16 weeks treatment with tralokinumab or placebo (control) in ECZTRA 2 trials.
Figure 8I:
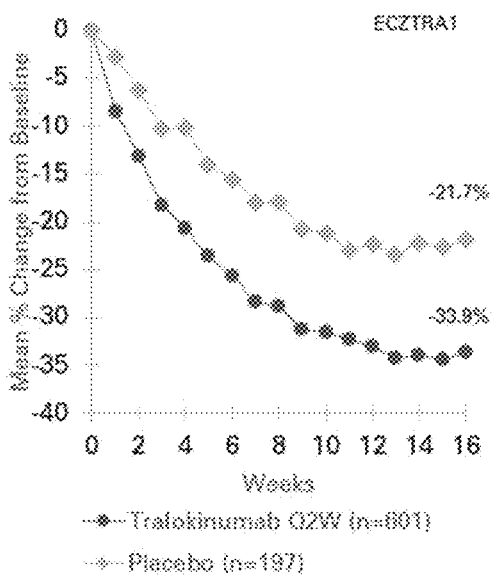
FIG. 8I. Scores for secondary endpoints (pruritus) at baseline and following 16 weeks treatment with tralokinumab or placebo (control) in ECZTRA 1 trials.
Figure 8J:
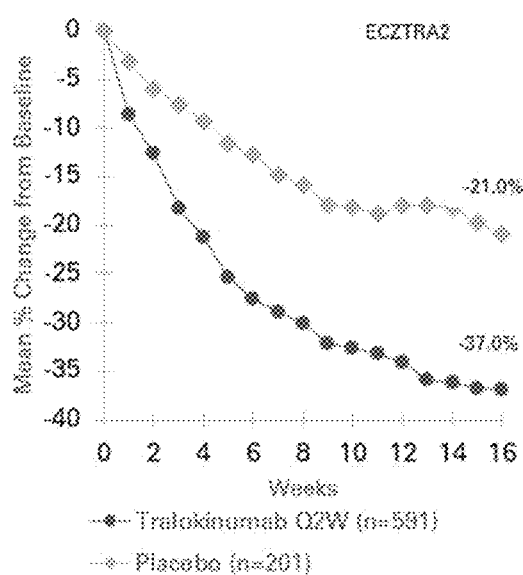
FIG. 8J. Scores for secondary endpoints (pruritus) at baseline and following 16 weeks treatment with tralokinumab or placebo (control) in ECZTRA 2 trials.
Figure 9:
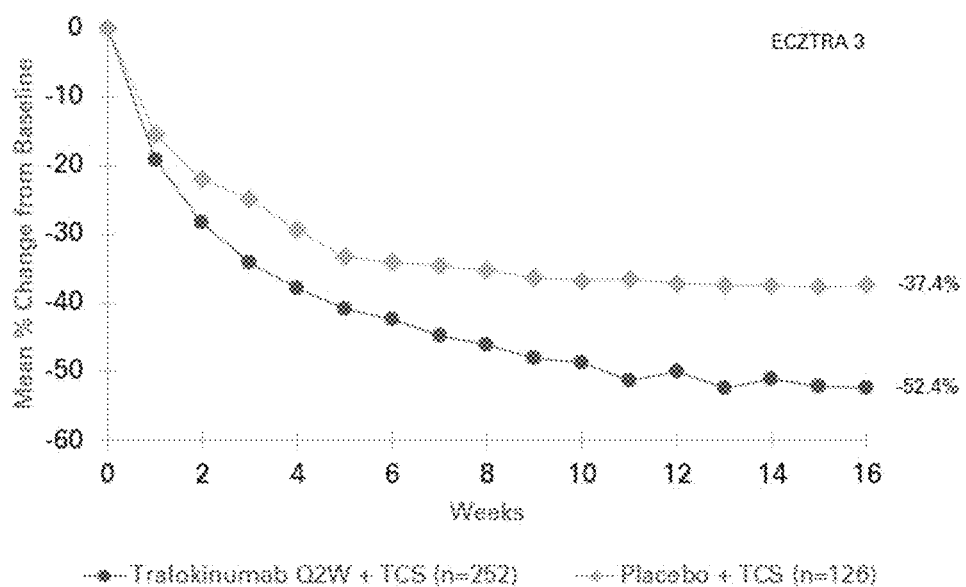
FIG. 9. Mean percent change from baseline in worst Daily Pruritus NRS (weekly average from week 0-16).

FIGS. 8A-8J, 11A-11C and 12A-12C shows data for secondary endpoints up to 16 weeks. Improvements in SCORAD, pruritus, DLQI, ERSI and POEM were observed early in the studies (see FIGS. 8A-8J, 11A-11C and 12A-12C). Improvement in EASI started soon after the start of treatment and was greater with tralokinumab than with placebo in both studies (FIGS. 8G-8H).

Conclusions

Tralokinumab monotherapy results in early significant improvements in PROs, as observed in the two trials. In particular, patients experience early benefit from tralokinumab monotherapy after initiation of treatment with significant improvement after only 2 weeks.

Example 6: Conjunctivitis in Tralokinumab-Treated Adult Patients with Moderate-to-Severe Atopic Dermatitis: Pooled Results from Five Clinical Trials Materials and Methods Patients treated with tralokinumab 300 mg or placebo (PBO) every 2 weeks were pooled from five trials: Ph 3 ECZTRA 1/2 (tralokinumab monotherapy) and ECZTRA 3 (tralokinumab in combination with topical corticosteroids), Ph 2 ECZTRA 5 (vaccine response in tralokinumab-treated patients with AD) and Ph 2b (efficacy and safety evaluation of tralokinumab) trials. Adverse events (AEs) were summarised for the initial treatment period (16 weeks for ECZTRA and 12 weeks for Ph 2b). Conjunctivitis was defined as an AE of special interest (AESI); events were captured from the AE form (ECZTRA) or by Medical Dictionary for Regulatory Activities search (Ph 2b). Cochran-Mantel-Haenszel weights were applied to calculate adjusted AE incidences to take into account different randomisation rates between tralokinumab and PBO.

Results

Adult patients treated with tralokinumab (n=1605) or PBO (n=680) were included in the analysis. During the initial treatment period, a conjunctivitis AESI (preferred terms conjunctivitis, conjunctivitis allergic, conjunctivitis bacterial and conjunctivitis viral) occurred in 126 (7.5%) pts treated with tralokinumab vs 21 (3.2%) with PBO. Overall, 145 and 23 events of conjunctivitis occurred in the tralokinumab and PBO groups, respectively, the majority were mild (68% vs 65%) or moderate (30% vs 35%) in severity; ophthalmologists confirmed 30% of conjunctivitis events across the tralokinumab (39 events) and PBO (6 events) groups. A similar percentage of events in the tralokinumab and PBO groups resolved (78.6% vs 73.9%) or were resolving (2.8% vs 4.3%) during the initial treatment period, respectively; no events were serious and two events led to permanent discontinuation of tralokinumab. A higher baseline of AD severity and previous history of allergic conjunctivitis were associated with increased conjunctivitis incidence. Median time to first event was similar for both groups (50.0 days vs 51.5 days); however, duration of conjunctivitis was longer in the tralokinumab (21.0 days vs 14.5 days) group. The majority of patients received treatment for their conjunctivitis (81% of tralokinumab pts vs 63% of PBO pts). Common treatments included ophthalmic antiallergics (28% vs 42%), anti-infectives (30% vs 11%), corticosteroids (22% vs 11%) and combined corticosteroids and anti-infectives (13.5% vs 15.8%).

Conclusion

The overall incidence of conjunctivitis, identified as an AESI in the initial treatment period of the AD pool, was higher for tralokinumab than for PBO, but the majority of cases were mild or moderate in severity. The majority of the conjunctivitis events were concomitantly treated and resolved or were resolving during the trials.

Example 7: Clinical Responses to Tralokinumab in Patients with Atopic Dermatitis Who Initially Achieved Sub-Optimal Responses and Continued Treatment Materials and methods: Patients who did not achieve clinical response, IGA 0/1 or EASI-75, in the ECZTRA 1 and 2 trials at week 16 were transferred to open-label tralokinumab 300 mg q2w plus optional TCS for an additional 36 weeks. This post hoc analysis of pooled data from both studies assessed clinical responses during open-label treatment in patients who initially achieved sub-optimal responses to tralokinumab after 16 weeks.

Results: In the pooled analysis, 686 of 1196 (57.4%) tralokinumab-treated patients (360 and 326 from ECZTRA 1 and 2, respectively) were transferred to open-label treatment at week 16. The proportion of patients achieving IGA 0/1 or EASI-75 with open-label tralokinumab plus optional TCS continued to increase, and 20.1% and 42.9% of these patients achieved IGA 0/1 and EASI-75, respectively, at week 52. More than half of the responder proportions at week 52 were achieved within 8 weeks of starting open-label treatment; 11.4% and 31.9% achieved IGA 0/1 and EASI-75 by week 24. An alternative analysis assessed patients (49.1%) who used concomitant anti-inflammatory treatment (including TCS) to be non-responders; the response rates in patients who did not use concomitant anti-inflammatory treatment were 13.9% and 25.7% for IGA 0/1 and EASI-75, respectively. When considering the level of AD disease activity at week 16, in patients who had EASI-50 to -74 at week 16, 53.2% achieved EASI-75 at week 52, and in the subgroup of patients with IGA 2 at week 16, 36.5% achieved IGA 0/1 at week 52. In patients who had EASI 25-50% at week 16, 40.7% achieved EASI-75 at week 52 and in patients having IGA 3 at week 16, 17.1% achieved IGA 0/1 at week 52.

In patients with EASI <25 at week 16, 29.3% achieved EASI-75 at week 52, and in patients with IGA 4 at week 16, 7.6% achieved IGA 0/1 at week 52.

Discussion: These data show that the majority of patients with initial sub-optimal responses to tralokinumab subsequently achieved EASI-75 with continued treatment and that responses correlated with AD disease activity achieved by week 16. In addition, clinical responses with continued treatment did not appear to be driven by the addition of optional TCS.

Example 8: Impact of Targeting IL-13 on *Staphylococcus aureus* Colonisation

Material & Methods: In the ECZTRA 1 phase III trial, patients with moderate-to-severe AD were randomised 3:1 to subcutaneous tralokinumab 300 mg or placebo (PBO) every 2 weeks for an initial 16 weeks. The change in skin colonisation by *S. aureus* at week 16 in patients was an exploratory endpoint. Absolute abundance of *S. aureus* on lesional skin was assessed by rotation of sterile swabs on the skin, followed by rtPCR of extracted DNA. Association of *S. aureus* colonisation with disease severity and select biomarkers was assessed. The ratio between treatment groups in relative reduction of *S. aureus* colonisation from baseline to week 16 was assessed by a t-test of changes in log-transformed values.

Results: 802 patients were randomised 603:199 to tralokinumab: PBO; 50.7% had severe AD (IGA-4) at baseline; mean EASI score was 32.4. *S. aureus* colonisation correlated with disease severity (EASI score) at baseline and week 16. *S. aureus* colonisation further correlated significantly with gene expression of biomarkers, including IL-13, IL-22 and hBD2, at baseline and week 16. Median *S. aureus* abundance was reduced more from baseline to week 16 in patients receiving tralokinumab (n=555; from 969 to 22 gene copies/cm$^2$) vs PBO (n=184; from 649 to 238 gene copies/cm$^2$), with a 10-fold greater reduction for tralokinumab vs PBO treated patients (ratio −0.09; p<0.0001). Use of rescue medication did not impact the results.

In patients not using rescue medication (64.2% of tralokinumab and 53.8% of placebo patients did not use rescue medication), there was a significant reduction in tralokinumab vs placebo treated patients (ratio=0.12; p<0.0001).

Figure 15:
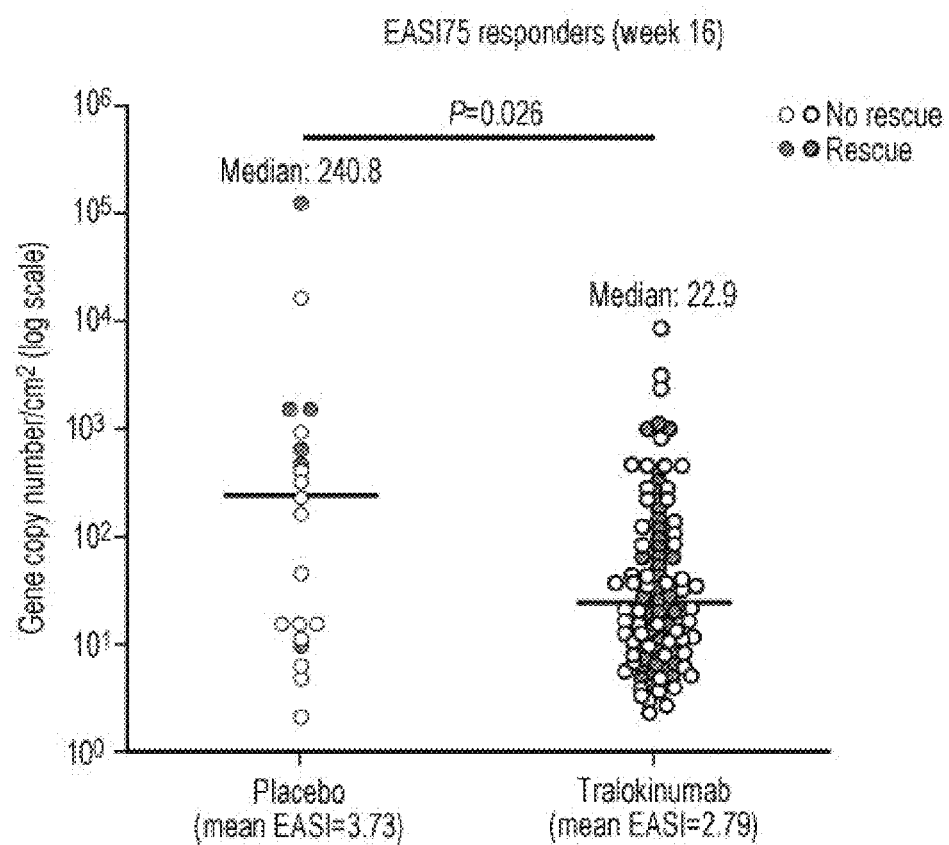
FIG. 15. Comparison of *S. aureus* colonisation in EASI-75 responders from tralokinumab and placebo groups.

When comparing EASI-75 responders from tralokinumab and placebo groups there was a lower median *S. aureus* colonisation at week 16 in tralokinumab treated patients than in placebo EASI-75 responders, see FIG. 15.

There was a significant reduction from baseline to week 16 in median count for tralokinumab vs placebo (−96.6%, p<0.0001 vs +34.2%, ns).

Conclusions: Treatment with tralokinumab was associated with significant reduction in *S. aureus* colonisation in lesional skin compared with PBO in adult patients with moderate-to-severe AD. This suggests that reduction of *S. aureus* colonisation by neutralisation of IL-13 contributes to the efficacy of tralokinumab in improving the AD hallmarks and breaking the cycle of itching, scratching, skin barrier dysfunction, and immune-mediated inflammation.

Example 9: Impact of Targeting IL-13 on Anxiety and Depression

Materials and methods: Patients in the ECZTRA 1-3 phase III trials were assessed for anxiety and depression using the Hospital Anxiety and Depression Scale (HADS).

Results: HADS results are summarised for ECZTRA 1-3 and the monotherapy pool in Table 17 below (initial treatment period: FAS).

Furthermore, for all pivotal phase 3 trials the HADS mean total score was reduced more from baseline to Week 16 in the tralokinumab group compared to placebo (p=0.38 for ECZTRA 1, p=0.001 for ECZTRA 2 and 3) (see Table 17).

For all pivotal phase 3 trials, a higher mean change from baseline in the HADS total score was observed in the tralokinumab group compared to placebo from Week 4 and onwards (FIGS. 13A-13D). The same pattern was observed when considering the 2 individual components of the HADS total score, i.e. the HADS anxiety score and the HADS depression score.

In ECZTRA 5, the mean change from baseline to Week 16 in the total HADS score was higher with tralokinumab compared to placebo with an adjusted mean change of −2.4 in the tralokinumab group and −0.6 in the placebo group leading to a treatment difference of −1.8 (p=0.033).

Conclusions: Treatment with tralokinumab was associated with significant reduction in anxiety and depression, as measured by HADS, compared with PBO in adult patients with moderate-to-severe AD.

Example 10: Impact of Targeting IL-13 on Health-Related Quality of Life

Short Form (36) Health Survey (SF-36)

Material & Methods: Short Form (36) Health Survey (SF-36) was assessed for patients in the ECZTRA 1 and 2 phase III trials described above.

Results: For both trials, there was an improvement in both the physical and mental component summary scores of SF-36 in both treatment groups through the initial treatment period.

TABLE 17

| | ECZTRA 1 | | ECZTRA 2 | | ECZTRA 1 + 2 | | ECZTRA 3 | |
|---|---|---|---|---|---|---|---|---|
| | Tralo Q2W (N = 601) | Placebo (N = 197) | Tralo Q2W (N = 591) | Placebo (N = 201) | Tralo Q2W (N = 1192) | Placebo (N = 398) | Tralo Q2W + TCS (N = 252) | Placebo + TCS (N = 126) |
| HADS anxiety and HADS depression scores <8 at Week 16 in subjects with baseline HADS anxiety or HADS depression subscale scores of ≥8[a] | | | | | | | | |
| n | 289 | 103 | 292 | 93 | 581 | 196 | 102 | 54 |
| Resp., % | 21.8% | 18.4% | 38.4% | 16.1% | 30.1% | 17.3% | 53.9% | 29.6% |
| Diff. (95% CI) | 3.0% (−5.8, 11.8) | | 21.2% (11.8, 30.5) | | 11.7% (5.3, 18.2) | | 24.8% (9.3, 40.4) | |
| p-value | 0.52 | | <0.001 | | 0.001 | | 0.003 | |
| Change from baseline to Week 16 in HADS total score[b] | | | | | | | | |
| n | 333 | 95 | 417 | 97 | 750 | 192 | 226 | 104 |
| Adj. mean change (SE) | −2.3 (0.26) | −1.8 (0.48) | −3.3 (0.26) | −1.4 (0.50) | −2.8 (0.18) | −1.6 (0.35) | −4.4 (0.37) | −2.2 (0.54) |
| Diff. (95% CI) | −0.5 (−1.5, 0.6) | | −1.9 (−3.0, −0.7) | | −1.2 (−1.9, −0.4) | | −2.2 (−3.4, −0.9) | |
| p-value | 0.38 | | 0.001 | | 0.003 | | 0.001 | |

Composite estimand: subjects who received rescue medication considered non-responders.
Subjects with missing data at Week 16 imputed as non-responders.
Mantel-Haenszel analysis of risk difference stratified by region and baseline IGA (and trial ID for ECZTRA 1 + 2).
P-value based on Cochran-Mantel-Haenszel test, stratified by region and baseline IGA (and trial ID for ECZTRA 1 + 2).
Hypothetical estimand: data collected after permanent discontinuation of IMP or initiation of rescue medication not included.
In case of no post-baseline assessments before initiation of rescue medication, the Week 4 change will be imputed as 0.
Repeated measurements analysis.

There was a higher proportion of responders with HADS anxiety and HADS depression scores <8 at Week 16 among subjects with a baseline HADS anxiety or HADS depression subscale scores of ≥8 in the tralokinumab group compared to the placebo group across all trials (p=0.52 for ECZTRA 1, p<0.001 for ECZTRA 2, p=0.003 for ECZTRA 3). The treatment difference between tralokinumab and placebo was similar in ECZTRA 2 (21.2%) and ECZTRA 3 (24.8%), whereas it was modest in ECZTRA 1 (3.0%) (see Table 17). source not found.).

In ECZTRA 1, the mean physical component summary score increased from 44.5 at baseline to 51.3 at Week 16 in the tralokinumab group and from 44.7 to 50.2 in the placebo group. The mean mental component summary score increased from 43.6 at baseline to 48.2 at Week 16 in the tralokinumab group and from 42.4 to 46.0 in the placebo group.

In ECZTRA 2, the mean physical component summary score increased from 44.3 at baseline to 51.5 at Week 16 in the tralokinumab group and from 43.4 to 48.6 in the placebo group. The mean mental component summary score increased from 43.6 at baseline to 48.4 at Week 16 in the tralokinumab group and from 43.2 to 44.8 in the placebo group.

For both trials, the change from baseline in both the physical and mental component summary scores was larger in the tralokinumab group compared with the placebo group at Week 16 is shown in Table 18 below.

TABLE 18

|  | ECZTRA 1 | | ECZTRA 2 | |
| --- | --- | --- | --- | --- |
|  | Tralokinumab Q2W (N = 601) | Placebo (N = 197) | Tralokinumab Q2W (N = 591) | Placebo (N = 201) |
| n | 333 | 94 | 417 | 97 |
| Change from baseline to Week 16 in SF-36 Physical Component Summary Score | | | | |
| Adj. mean change (SE) | 4.5 (0.30) | 2.9 (0.56) | 5.8 (0.29) | 3.2 (0.57) |
| Diff. | 1.6 | | 2.6 | |
| (95% CI) | (0.3, 2.8) | | (1.4, 3.9) | |
| p-value | 0.013 | | <0.001 | |
| Change from baseline to Week 16 in SF-36 Mental Component Summary Score | | | | |
| Adj. mean change (SE) | 2.5 (0.42) | 0.3 (0.78) | 3.5 (0.38) | 0.5 (0.76) |
| Diff. | 2.3 | | 3.0 | |
| (95% CI) | (0.5, 4.0) | | (1.3, 4.7) | |
| p-value | 0.010 | | <0.001 | |

Change from baseline to Week 16 in SF-36, initial treatment period: FAS. Hypothetical estimand: data collected after permanent discontinuation of Tralokinumab or initiation of rescue medication not included. In case of no post-baseline assessments before initiation of rescue medication, the Week 2 change will be imputed as 0. Repeated measurements analysis.

In EZCTRA 1, the adjusted mean change in the SF-36 Physical Component Summary Score was 4.5 in the tralokinumab group compared to 2.9 in the placebo group leading to a treatment difference of 1.6 (p=0.013). The adjusted mean change in the SF-36 Mental Component Summary Score was 2.5 for tralokinumab and 0.3 for placebo leading to a treatment difference of 2.3 (p=0.010).

In ECTZRA 2, the adjusted mean change in the SF-36 Physical Component Summary Score was 5.8 in the tralokinumab group compared to 3.2 in the placebo group leading to a treatment difference of 2.6 (p<0.001). The adjusted mean change in the SF-36 Mental Component Summary Score was 3.5 for tralokinumab and 0.5 for placebo leading to a treatment difference of 3.0 (p<0.001).

Conclusions: Treatment with tralokinumab was associated with significant improvement in SF-36 Physical and Mental Component Summary Scores compared with PBO in adult patients with moderate-to-severe AD.

EuroQoL 5-Dimension Health Questionnaire 5 Level (EQ-5D-5L)

Material & Methods: EuroQOL 5-Dimension Health Questionnaire 5 Level (EQ-5D-5L) was assessed for patients in the ECZTRA 1-3 phase III trials.

Results: For all the trials, the subjects' perception of their health improved in both treatment groups through the initial treatment period based on both parts of EQ-5D-5L (i.e. the EQ-5D-5L index score and the EQ-5D-5L VAS).

In ECZTRA 1, the mean EQ-5D-5L index score increased from 0.553 at baseline to 0.787 at Week 16 in the tralokinumab group and from 0.571 to 0.739 in the placebo group. The mean EQ-5D-5L VAS score increased from 53.8 at baseline to 72.7 at Week 16 in the tralokinumab group and from 54.7 to 69.4 in the placebo group.

In ECZTRA 2, the mean EQ-5D-5L index score increased from 0.544 at baseline to 0.779 at Week 16 in the tralokinumab group and from 0.543 to 0.683 in the placebo group. The mean EQ-5D-5L VAS score increased from 58.0 at baseline to 74.4 at Week 16 in the tralokinumab group and from 55.7 to 68.0 in the placebo group.

In ECZTRA 3, the mean EQ-5D-5L index score increased from 0.561 at baseline to 0.839 at Week 16 in the tralokinumab+TCS group and from 0.589 to 0.766 in the placebo+TCS group. The mean EQ-5D-5L VAS score increased from 59.1 at baseline to 76.1 at Week 16 in the tralokinumab+TCS group and from 59.4 to 72.8 in the placebo+TCS group.

The change from baseline for both sections of the EQ-5D-5L are summarised for ECZTRA 1-3 in Table 19 below.

TABLE 19

|  | ECZTRA 1 | | ECZTRA 2 | | ECZTRA 3 | |
| --- | --- | --- | --- | --- | --- | --- |
|  | Tralo Q2W (N = 601) | Placebo (N = 197) | Tralo Q2W (N = 591) | Placebo (N = 201) | Tralo Q2W + TCS (N = 252) | Placebo + TCS (N = 126) |
| Change from baseline to Week 16 in EQ-5D-5L index score | | | | | | |
| n | 333 | 95 | 418 | 197 | 226 | 104 |
| Adj. mean change (SE) | 0.154 (0.010) | 0.092 (0.019) | 0.187 (0.010) | 0.085 (0.019) | 0.263 (0.01) | 0.176 (0.02) |
| Diff. (95% CI) | 0.062 (0.020, 0.105) | | 0.102 (0.060, 0.145) | | 0.087 (0.047, 0.127) | |
| p-value | 0.004 | | <0.001 | | <0.001 | |
| Change from baseline to Week 16 in EQ-5D-5L VAS | | | | | | |
| n | 333 | 95 | 418 | 197 | 226 | 104 |
| Adj. mean change (SE) | 11.0 (0.92) | 6.3 (1.70) | 12.8 (0.74) | 15.8 (1.48) | 16.3 (1.16) | 13.0 (1.69) |
| Diff. (95% CI) | 4.7 (0.9, 8.5) | | 7.0 (3.8, 10.3) | | 3.2 (−0.8, 7.3) | |
| p-value | 0.016 | | <0.001 | | 0.12 | |

Endpoints related to EQ-5D-5L for the pivotal phase 3 trials, initial treatment period:
FAS. Hypothetical estimand: data collected after permanent discontinuation of IMP or initiation of rescue medication not included.
In case of no post-baseline assessments before initiation of rescue medication, the Week 4 change will be imputed as 0.
Repeated measurements analysis.

Across all trials, the subjects' perception of their health improved, based on the EQ-5D-5L index score. The change from baseline to Week 16 in the EQ-5D-5L index score was higher in the tralokinumab group compared to the placebo group across all trials with similar treatment differences between trials (p=0.004 for ECZTRA 1, p<0.001 for ECZTRA 2 and 3). For all trials, differences were observed from first assessment at Week 4 and onwards.

Furthermore, the subjects' perception of their health improved, based on the EQ-5D-5L VAS across all trials. The change from baseline to Week 16 in the EQ-SD-5L VAS was higher in the tralokinumab group compared to the placebo group across all trials with a higher treatment difference in ECZTRA 2 compared to ECZTRA 1 and ECZTRA 3 (p=0.016 for ECZTRA 1, p<0.001 for ECZTRA 2, p=0.12 for ECZTRA 3). For all pivotal trials, differences were observed from Week 4 and onwards).

In ECZTRA 5, the mean change from baseline to Week 16 in the EQ-5D-5L index score was higher with tralokinumab compared to placebo with an adjusted mean change of 0.130 in the tralokinumab group and 0.097 in the placebo group leading to a treatment difference of 0.034 (p=0.19). The mean change in EQ-5D-5L VAS was 8.3 in the tralokinumab group and 0.6 in the placebo group leading to a treatment difference of 7.6 (p=0.004).

Conclusions: Treatment with tralokinumab was associated with significant improvement in the subjects' perception of their health as measured by EQ-5D-5L compared with PBO in adult patients with moderate-to-severe AD.

LIST OF ABBREVIATIONS

AD, atopic dermatitis
AE, adverse event
AESI, adverse event of special interest
BSA, body surface area involvement
CI, confidence interval
DLQI, Dermatology Life Quality Index
EASI, Eczema Area and Severity Index
EASI-50, at least 50% reduction in Eczema Area and Severity Index score
EASI-75, at least 75% reduction in Eczema Area and Severity Index score
EASI-90, at least 90% reduction in Eczema Area and Severity Index score
EQ-5D-5L, EuroQoL 5-Dimension Health Questionnaire 5 Level
FAS, full analysis set
HADS=Hospital Anxiety and Depression Scale
IGA, Investigator's Global Assessment
IGA-0/1, Investigators' Global Assessment score of 0 (clear) or 1 (almost clear)
IMP, investigational medicinal product
IQR, interquartile range
MedDRA, Medical Dictionary for Regulatory Activities
NRS, Numeric Rating Scale
PT, preferred term
PYE, patient-years of exposure
Q2W, every other week, i.e. every 2 weeks
Q4W, every 4 weeks
R, rate (number of AEs divided by PYE multiplied by 100)
SAEs, serious adverse events
SCORAD, SCORing Atopic Dermatitis
SE, standard error
SF-36. Short Form (36) Health Survey
TCS, topical corticosteroids.

The invention claimed is:

1. A method of treating atopic dermatitis (AD) in a subject in need thereof, wherein the method comprises the steps of: (a) administering a first dose of about 300 mg of an IL-13 binding protein to the subject; and (b) administering one or more secondary dose(s) of about 300 mg of the IL-13 binding protein to the subject, wherein each secondary dose is administered to the subject about 4 weeks after the immediately preceding dose, wherein prior to step (a) the method further comprises a step of administering a first prior dose of the IL-13 binding protein followed by one or more prior dose(s) of the IL-13 binding protein to the subject, such that each of the one or more prior dose(s) of the IL-13 binding protein is administered to the subject about 2 weeks after the immediately preceding prior dose, and wherein the IL-13 binding protein is an anti-IL-13 antibody, or an IL-13 binding fragment thereof, comprising a heavy chain variable region (HCVR) and a light chain variable region (LCVR), wherein:
- (i) the heavy chain variable region comprises:
  - a heavy chain complementarity determining region 1 (HCDR1) comprising the amino acid sequence of SEQ ID NO:1; a heavy chain complementarity determining region 2 (HCDR2) comprising the amino acid sequence of SEQ ID NO: 2; and a heavy chain complementarity determining region 3 (HCDR3) comprising the amino acid sequence of SEQ ID NO:3; and
- (ii) the light chain variable region comprises:
  - a light chain complementarity determining region 1 (LCDR1) comprising the amino acid sequence of SEQ ID NO:4; a light chain complementarity determining region 2 (LCDR2) comprising the amino acid sequence of SEQ ID NO:5; and a light chain complementarity determining region 3 (LCDR3) comprising the amino acid sequence of SEQ ID NO:6.

2. The method of claim 1, wherein the AD is moderate-to-severe or severe AD.

3. The method of claim 1, wherein step (b) is continued for a duration selected from the group consisting of at least 8 weeks, at least 12 weeks, at least 3 months, at least 16 weeks, at least 20 weeks, at least 24 weeks, at least 6 months, at least 28 weeks, at least 32 weeks, at least 36 weeks, at least a year, and at least 52 weeks.

4. The method of claim 1, wherein the method comprises the steps of: (a) subcutaneously administering the first dose of the IL-13 binding protein to the subject; and (b) subcutaneously administering the one or more secondary dose(s) of the IL-13 binding protein to the subject.

5. The method of claim 1, wherein prior to step (a) the method comprises administering the prior dose(s) of the IL-13 binding protein to the subject for about 2 weeks, about 4 weeks, about 6 weeks, about 8 weeks, about 12 weeks, about 16 weeks or about 20 weeks.

6. The method of claim 1, wherein the method comprises the steps of:
- (i) administering the prior dose(s) of the IL-13 binding protein to the subject for from 2 weeks to 36 weeks; and
- (ii) administering the one or more secondary dose(s) of the IL-13 binding protein to the subject for at least 8 weeks,
wherein each of the one or more prior dose(s) and each of the one or more secondary dose(s) is about 300 mg of IL-13 binding protein.

7. The method of claim 1, wherein following step (b) the method further comprises a step of: (c) administering one or more tertiary dose(s) of the IL-13 binding protein to the subject.

8. The method according to claim 7, wherein each tertiary dose of the IL-13 binding protein is administered from 1 week to 6 weeks after the immediately preceding dose.

9. The method according to claim 8, wherein each of the one or more tertiary dose(s) of the IL-13 binding protein is administered to the subject 2 weeks after the immediately preceding dose.

10. The method of claim 1, wherein the method comprises the steps of:
- (i) administering the prior dose(s) of the IL-13 binding protein to the subject for around 8 weeks to 16 weeks; and
- (ii) administering the one or more secondary dose(s) of the IL-13 binding protein to the subject for at least 12 weeks, wherein the first dose of said one or more prior dose(s) is around 600 mg of IL-13 binding protein and each prior dose, the first dose, and each secondary dose administered after the first of said one or more prior dose(s) is around 300 mg of IL-13 binding protein.

11. The method of claim 1, wherein the method comprises the steps of:
- (i) administering the prior dose(s) of the IL-13 binding protein to the subject for around 12 weeks to 16 weeks; and
- (ii) administering the one or more secondary dose(s) of the IL-13 binding protein to the subject for at least 16 weeks,
wherein each dose is around 300 mg of IL-13 binding protein.

12. The method of claim 1, wherein the method comprises the steps of:
- (i) administering the prior dose(s) of the IL-13 binding protein to the subject for around 12 weeks to 16 weeks; and
- (ii) administering the one or more secondary dose(s) of the IL-13 binding protein to the subject for at least 16 weeks, wherein the first dose of said one or more prior doses is around 600 mg of IL-13 binding protein and each prior dose, the first dose, and each secondary dose administered after the first of said one or more prior dose(s) is around 300 mg of IL-13 binding protein.

13. The method of claim 1, wherein each dose of IL-13 binding protein is administered in one or two injections.

14. The method of claim 1, wherein each dose of the IL-13 binding protein is administered as a pharmaceutical composition comprising 50 mM sodium acetate buffer, 85 mM sodium chloride, 0.01% (w/v) polysorbate 80, wherein the pharmaceutical composition has a pH of 5.5.

15. The method of claim 1, wherein the IL-13 binding protein is a monoclonal anti-IL-13 antibody, or an IL-13-binding fragment thereof.

16. The method of claim 1, wherein the IL-13 binding protein is a human anti-IL-13 antibody, or an IL-13-binding fragment thereof.

17. The method of claim 1, wherein the IL-13 antibody is an IgG4 antibody.

18. The method of claim 1, wherein the IL-13-binding fragment is selected from a Fab, Fab', F(ab')2, Fd, Fv, single-chain Fv (scFv), or disulfide-linked Fvs.

19. The method of claim 1, wherein the anti-IL-13 antibody, or the IL-13-binding fragment thereof, further comprises:
- (i) an amino acid sequence that is at least 80%, at least 85%, at least 90%, at least 95%, at least 96%, at least 97%, at least 98%, or at least 99% identical to a heavy chain variable region sequence of SEQ ID NO: 8; and/or
- (ii) an amino acid sequence that is at least 80%, at least 85%, at least 90%, at least 95%, at least 96%, at least 97%, at least 98%, or at least 99% identical to a light chain variable region sequence of SEQ ID NO: 10.

20. The method of claim 1, wherein the anti-IL-13 antibody, or the IL-13-binding fragment thereof, comprises a heavy chain variable region sequence of SEQ ID NO: 8 and a light chain variable region sequence of SEQ ID NO: 10.

21. The method of claim 1, wherein the anti-IL-13 antibody, or the IL-13-binding fragment thereof, comprises: (i) an amino acid sequence that is at least 80%, at least 85%, at least 90%, at least 95%, at least 96%, at least 97%, at least 98%, or at least 99% identical to the heavy chain sequence of SEQ ID NO: 11; and/or (ii) an amino acid sequence that is at least 80%, at least 85%, at least 90%, at least 95%, at least 96%, at least 97%, at least 98%, or at least 99% identical to the light chain sequence of SEQ ID NO: 12.

22. The method of claim 1, wherein the anti-IL-13 antibody, or the IL-13-binding fragment thereof, comprises a heavy chain of SEQ ID NO: 11 and a light chain sequence of SEQ ID NO: 12.

23. The method of claim 1, wherein the IL-13 binding protein is administered as a monotherapy.

24. The method of claim 1, wherein the IL-13 binding protein is administered in combination with a second therapeutic agent selected from the group consisting of a topical corticosteroid, a topical calcineurin inhibitor, an anti-histamine, an emollient, or an anti-bacterial therapeutic.

25. The method of claim 1, wherein the method achieves:
(i) ≥50% improvement of Eczema Area and Severity Index (EASI-50) compared to baseline;
(ii) at least a 2 point reduction of Investigator's Global Assessment (IGA) score compared to baseline;
(iii) at least a 4 point reduction in Patient-Oriented Eczema Measure (POEM) score compared to baseline;
(iv) at least a 1 point reduction in Worst Daily Pruritus Numerical Rating Scale (NRS) compared to baseline;
(v) at least a 0.4 point reduction in eczema-related sleep interference compared to baseline;
(vi) at least a 1-point reduction in Hospital Anxiety and Depression Scale (HADS) score compared to baseline;
(vii) at least a 4-point increase in Short Form (36) Health Survey (SF-36) Physical Component Summary Score and/or at least a 2-point increase in SF-36 Mental Component Summary Score compared to baseline;
(viii) at least a 4-point reduction in Dermatology Life Quality Index (DLQI) score compared to baseline; and/or
(ix) at least a 1-point reduction in Patient Global Impression of Bother (PGI-B) score compared to baseline,
wherein baseline is an initial measurement of the relevant AD-associated parameter or patient-related outcome taken before initiation of treatment by the method.

26. The method of claim 1, wherein administering the one or more prior dose(s) is continued until the subject achieves an IGA score of 0 or 1 and/or a 75% improvement of Eczema Area Severity Index (EASI-75) over baseline in the subject.

27. The method of claim 1, wherein the subject has experienced conjunctivitis when treated with (i) the IL-13 binding protein in combination with a topical corticosteroid, (ii) an anti-IL4Rα antibody, or (iii) an antibody that inhibits IL4 and/or IL13 signaling.

28. The method of claim 1, wherein the method comprises the steps of:
(i) administering the one or more prior dose(s) of the IL-13 binding protein to the subject until the subject achieves an IGA score of 0 or 1; and
(ii) administering the one or more secondary dose(s) of the IL-13 binding protein to the subject for at least 8 weeks,
wherein each of the one or more prior dose(s) and each of the one or more secondary dose(s) is about 300 mg of IL-13 binding protein.

29. The method of claim 1, wherein the method comprises the steps of:
(i) administering the one or more prior dose(s) of the IL-13 binding protein to the subject until the subject achieves an IGA score of 0 or 1; and
(ii) administering one or more secondary dose(s) of the IL-13 binding protein to the subject for at least 8 weeks, wherein the first dose of said one or more prior doses is around 600 mg of IL-13 binding protein and each prior dose, the first dose, and each secondary dose administered after the first of said one or more prior dose(s) is around 300 mg of IL-13 binding protein.

30. The method of claim 1, wherein prior to step (a) the method comprises administering the prior dose(s) of the IL-13 binding protein to the subject for about 16 weeks.

31. The method of claim 1, wherein the method comprises administering the prior dose(s) of the IL-13 binding protein to the subject for around 16 weeks; wherein the first dose of said one or more prior doses is around 600 mg of IL-13 binding protein and each prior dose, the first dose, and each secondary dose administered after the first of said one or more prior dose(s) is around 300 mg of IL-13 binding protein.

32. The method of claim 1, wherein the anti-IL-13 antibody is tralokinumab.

33. A method of treating a skin infection in a subject with moderate-to-severe or severe AD, wherein the method comprises the steps of: (a) administering a first dose of about 300 mg of an IL-13 binding protein to the subject; and (b) administering one or more secondary dose(s) of about 300 mg of the IL-13 binding protein to the subject, wherein each secondary dose is administered to the subject about 4 weeks after the immediately preceding dose, wherein the IL-13 binding protein is an anti-IL-13 antibody, or an IL-13 binding fragment thereof, comprising a heavy chain variable region (HCVR) and a light chain variable region (LCVR), wherein:
(i) the heavy chain variable region comprises:
a heavy chain complementarity determining region 1 (HCDR1) comprising the amino acid sequence of SEQ ID NO:1; a heavy chain complementarity determining region 2 (HCDR2) comprising the amino acid sequence of SEQ ID NO: 2; and a heavy chain complementarity determining region 3 (HCDR3) comprising the amino acid sequence of SEQ ID NO:3; and
(ii) the light chain variable region comprises:
a light chain complementarity determining region 1 (LCDR1) comprising the amino acid sequence of SEQ ID NO:4; a light chain complementarity determining region 2 (LCDR2) comprising the amino acid sequence of SEQ ID NO:5; and a light chain complementarity determining region 3 (LCDR3) comprising the amino acid sequence of SEQ ID NO:6.

34. A method of treating pruritus in a subject with moderate-to-severe or severe AD, wherein the method comprises the steps of: (a) administering a first dose of about 300 mg of an IL-13 binding protein to the subject; and (b) administering one or more secondary dose(s) of about 300 mg of the IL-13 binding protein to the subject, wherein each secondary dose is administered to the subject about 4 weeks after the immediately preceding dose, wherein the IL-13 binding protein is an anti-IL-13 antibody, or an IL-13 binding fragment thereof, comprising a heavy chain variable region (HCVR) and a light chain variable region (LCVR), wherein:
(i) the heavy chain variable region comprises:
a heavy chain complementarity determining region 1 (HCDR1) comprising the amino acid sequence of SEQ ID NO:1; a heavy chain complementarity determining region 2 (HCDR2) comprising the amino acid sequence of SEQ ID NO: 2; and a heavy chain complementarity determining region 3 (HCDR3) comprising the amino acid sequence of SEQ ID NO:3; and (ii) the light chain variable region comprises:
a light chain complementarity determining region 1 (LCDR1) comprising the amino acid sequence of SEQ ID NO:4; a light chain complementarity determining region 2 (LCDR2) comprising the amino acid sequence of SEQ ID NO:5; and a light chain complementarity determining region 3 (LCDR3) comprising the amino acid sequence of SEQ ID NO:6.

35. A method of treating eczema-related sleep interference in a subject with moderate-to-severe or severe AD, wherein the method comprises the steps of: (a) administering a first dose of about 300 mg of an IL-13 binding protein to the subject; and (b) administering one or more secondary dose(s) of about 300 mg of the IL-13 binding protein to the subject, wherein each secondary dose is administered to the subject about 4 weeks after the immediately preceding dose, wherein the IL-13 binding protein is an anti-IL-13 antibody, or an IL-13 binding fragment thereof, comprising a heavy chain variable region (HCVR) and a light chain variable region (LCVR), wherein:

(i) the heavy chain variable region comprises:
a heavy chain complementarity determining region 1 (HCDR1) comprising the amino acid sequence of SEQ ID NO:1; a heavy chain complementarity determining region 2 (HCDR2) comprising the amino acid sequence of SEQ ID NO: 2; and a heavy chain complementarity determining region 3 (HCDR3) comprising the amino acid sequence of SEQ ID NO:3; and (ii) the light chain variable region comprises:
a light chain complementarity determining region 1 (LCDR1) comprising the amino acid sequence of SEQ ID NO:4; a light chain complementarity determining region 2 (LCDR2) comprising the amino acid sequence of SEQ ID NO:5; and a light chain complementarity determining region 3 (LCDR3) comprising the amino acid sequence of SEQ ID NO:6.

36. A method of treating anxiety and/or depression in a subject with moderate-to-severe or severe AD, wherein the method comprises the steps of: (a) administering a first dose of about 300 mg of an IL-13 binding protein to the subject; and (b) administering one or more secondary dose(s) of about 300 mg of the IL-13 binding protein to the subject, wherein each secondary dose is administered to the subject about 4 weeks after the immediately preceding dose, wherein the IL-13 binding protein is an anti-IL-13 antibody, or an IL-13 binding fragment thereof, comprising a heavy chain variable region (HCVR) and a light chain variable region (LCVR), wherein:

(i) the heavy chain variable region comprises:
a heavy chain complementarity determining region 1 (HCDR1) comprising the amino acid sequence of SEQ ID NO: 1; a heavy chain complementarity determining region 2 (HCDR2) comprising the amino acid sequence of SEQ ID NO: 2; and a heavy chain complementarity determining region 3 (HCDR3) comprising the amino acid sequence of SEQ ID NO:3; and (ii) the light chain variable region comprises:
a light chain complementarity determining region 1 (LCDR1) comprising the amino acid sequence of SEQ ID NO:4; a light chain complementarity determining region 2 (LCDR2) comprising the amino acid sequence of SEQ ID NO:5; and a light chain complementarity determining region 3 (LCDR3) comprising the amino acid sequence of SEQ ID NO:6.

37. A method of improving health status and/or quality of life in a subject with moderate-to-severe or severe AD, wherein the method comprises the steps of: (a) administering a first dose of about 300 mg of an IL-13 binding protein to the subject; and (b) administering one or more secondary dose(s) of about 300 mg of the IL-13 binding protein to the subject, wherein each secondary dose is administered to the subject about 4 weeks after the immediately preceding dose, wherein the IL-13 binding protein is an anti-IL-13 antibody, or an IL-13 binding fragment thereof, comprising a heavy chain variable region (HCVR) and a light chain variable region (LCVR), wherein:

(i) the heavy chain variable region comprises:
a heavy chain complementarity determining region 1 (HCDR1) comprising the amino acid sequence of SEQ ID NO:1; a heavy chain complementarity determining region 2 (HCDR2) comprising the amino acid sequence of SEQ ID NO: 2; and a heavy chain complementarity determining region 3 (HCDR3) comprising the amino acid sequence of SEQ ID NO:3; and (ii) the light chain variable region comprises:
a light chain complementarity determining region 1 (LCDR1) comprising the amino acid sequence of SEQ ID NO:4; a light chain complementarity determining region 2 (LCDR2) comprising the amino acid sequence of SEQ ID NO:5; and a light chain complementarity determining region 3 (LCDR3) comprising the amino acid sequence of SEQ ID NO:6; and wherein an improvement in the health status and/or quality of life of the subject is determined by an increase in the subject's Short Form (36) Health Survey (SF-36) score, Dermatology Life Quality Index (DLQI) score and/or Patient Global Impression of Bother (PGI-B) score.

* * * * *